(12) United States Patent
Corrigan et al.

(10) Patent No.: US 10,538,049 B2
(45) Date of Patent: Jan. 21, 2020

(54) SHAPE-FORMABLE APPARATUS COMPRISING LOCKING SHEETS

(71) Applicant: 3M INNOVATIVE PROPERTIES COMPANY, St. Paul, MN (US)

(72) Inventors: Thomas R. Corrigan, St. Paul, MN (US); Marc A. Egeland, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 197 days.

(21) Appl. No.: 15/535,297

(22) PCT Filed: Dec. 14, 2015

(86) PCT No.: PCT/US2015/065494
§ 371 (c)(1),
(2) Date: Jun. 12, 2017

(87) PCT Pub. No.: WO2016/100182
PCT Pub. Date: Jun. 23, 2016

(65) Prior Publication Data
US 2017/0360590 A1 Dec. 21, 2017

Related U.S. Application Data

(60) Provisional application No. 62/094,240, filed on Dec. 19, 2014.

(51) Int. Cl.
*B32B 1/02* (2006.01)
*B65D 75/12* (2006.01)
(Continued)

(52) U.S. Cl.
CPC ............... *B32B 1/02* (2013.01); *A61B 17/02* (2013.01); *A61F 5/05833* (2013.01);
(Continued)

(58) Field of Classification Search
CPC ...... B65D 65/38; B65D 65/40; B65D 65/403; B65D 65/406; B65D 75/002;
(Continued)

(56) References Cited

U.S. PATENT DOCUMENTS 2,958,593 A 11/1960 Hoover
3,408,705 A 11/1968 Kayser
(Continued)

FOREIGN PATENT DOCUMENTS

DE 102008059288 10/2012
EP 0267640 5/1988
(Continued)

OTHER PUBLICATIONS

Liu, "Applications of non-circular cross-section chemical fibers"; Chemical Fibers International; vol. 61; No. 4; 2011; pp. 210-212.
(Continued)

*Primary Examiner* — Walter Aughenbaugh
(74) *Attorney, Agent, or Firm* — Yufeng Dong; X. Christina Huang

(57) ABSTRACT

A shape-formable apparatus comprising locking sheets. The apparatus can have a first state in which the apparatus is formable, and a second state in which the apparatus has the desired shape and is substantially less formable than in the first state. The apparatus can further include an envelope defining a chamber, a port positioned to fluidly couple the chamber with ambience, and at least two locking sheets positioned in the chamber in an at least partially overlapping configuration. Each locking sheet comprises a major surface, and at least a portion of each locking sheet can be patterned to include solid regions and open regions, the solid regions being movable with respect to one another within the major surface.

19 Claims, 20 Drawing Sheets

(51) Int. Cl.

| | | |
|---|---|---|
| *B65D 65/40* | (2006.01) | |
| *B65D 65/38* | (2006.01) | |
| *B65D 75/00* | (2006.01) | |
| *B65B 11/50* | (2006.01) | |
| *B65B 17/02* | (2006.01) | |
| *A61F 5/058* | (2006.01) | |
| *A61B 17/02* | (2006.01) | |
| *B65D 81/127* | (2006.01) | |
| *F16M 13/00* | (2006.01) | |
| *B65D 81/20* | (2006.01) | |
| *A61B 90/00* | (2016.01) | |
| *A61B 17/00* | (2006.01) | |

(52) U.S. Cl.
CPC ............. *B65B 11/50* (2013.01); *B65B 17/02* (2013.01); *B65B 17/025* (2013.01); *B65D 65/38* (2013.01); *B65D 65/40* (2013.01); *B65D 65/403* (2013.01); *B65D 65/406* (2013.01); *B65D 75/002* (2013.01); *B65D 75/006* (2013.01); *B65D 75/12* (2013.01); *B65D 81/127* (2013.01); *F16M 13/00* (2013.01); *A61B 2017/00004* (2013.01); *A61B 2017/00566* (2013.01); *A61B 2017/00858* (2013.01); *A61B 2017/00862* (2013.01); *A61B 2017/00889* (2013.01); *A61B 2017/00946* (2013.01); *A61B 2017/00955* (2013.01); *A61B 2017/0212* (2013.01); *A61B 2090/0801* (2016.02); *B65D 81/2023* (2013.01); *B65D 81/2038* (2013.01)

(58) Field of Classification Search
CPC .. B65D 75/006; B65D 75/12; B65D 81/2023; B65D 81/2038; B32B 1/02; B65B 17/02; B65B 17/025; B65B 11/50
See application file for complete search history.

(56) References Cited

U.S. PATENT DOCUMENTS

| | | |
|---|---|---|
| 3,745,998 A | 7/1973 | Rose |
| 4,227,350 A | 10/1980 | Fitzer |
| 4,657,003 A | 4/1987 | Wirtz |
| 4,885,811 A | 12/1989 | Hayes |
| 4,991,362 A | 2/1991 | Heyer |
| 5,025,596 A | 6/1991 | Heyer |
| 5,348,259 A | 9/1994 | Blanco |
| 5,685,935 A | 11/1997 | Heyer |
| 5,718,669 A | 2/1998 | Marble |
| 6,251,065 B1 | 6/2001 | Kochamba |
| 6,276,365 B1 | 8/2001 | Stelzenmuller |
| 6,308,353 B1 | 10/2001 | Van Steenburg |
| 6,607,479 B1 | 8/2003 | Kochamba |
| 6,783,491 B2 | 8/2004 | Saadat |
| 6,796,940 B2 | 9/2004 | Bonadio |
| 6,890,292 B2 | 5/2005 | Kochamba |
| 6,902,523 B2 | 6/2005 | Kochamba |
| 6,936,002 B2 | 8/2005 | Kochamba |
| 7,237,555 B2 | 7/2007 | Kochamba |
| 7,309,321 B2 | 12/2007 | Farley |
| 7,550,189 B1 | 6/2009 | McKnight |
| 7,594,915 B2 | 9/2009 | Kochamba |
| 7,892,630 B1 | 2/2011 | McKnight |
| 7,901,524 B1 | 3/2011 | McKnight et al. |
| 8,246,575 B2 | 8/2012 | Viola |
| 2005/0137513 A1 | 6/2005 | Rugfelt |
| 2005/0151015 A1 | 7/2005 | Cagle |
| 2007/0244476 A1 | 10/2007 | Kochamba |
| 2007/0244534 A1 | 10/2007 | Kochamba |
| 2009/0101156 A1 | 4/2009 | Rugfelt |
| 2009/0187163 A1 | 7/2009 | Uihlein |
| 2010/0054903 A1 | 3/2010 | Jones |
| 2012/0038180 A1 | 2/2012 | Steltz |
| 2012/0088959 A1 | 4/2012 | Deasey |
| 2012/0179097 A1 | 7/2012 | Cully |
| 2012/0280421 A1 | 11/2012 | Keating |
| 2012/0310126 A1 | 12/2012 | Bureau |

FOREIGN PATENT DOCUMENTS

| | | |
|---|---|---|
| EP | 0196990 | 2/1991 |
| EP | 2796114 | 10/2014 |
| WO | WO 2011-079865 | 7/2011 |
| WO | WO 2012-093992 | 7/2012 |
| WO | WO 2013-113332 | 8/2013 |
| WO | WO 2016-100170 | 6/2016 |
| WO | WO 2016-100174 | 6/2016 |
| WO | WO 2016-100177 | 6/2016 |
| WO | WO 2016-100182 | 6/2016 |

OTHER PUBLICATIONS

Ou, "jamSheets: Thin Interfaces with Tunable Stiffness Enabled by Layer Jamming"; Association for Computing Machinery (ACM); 978-1-4503-2635; 2014; p. 65-72; 8 pgs.
Brochure entitled "Varstiff © by tecnalia—Setting up a marketing company for smart textiles"; 2 pgs; (date unknown but believed to be prior to the date of the filing of the present application).
International Search report for PCT International Application No. PCT/US2015/065494 dated Apr. 19, 2016, 4pages.

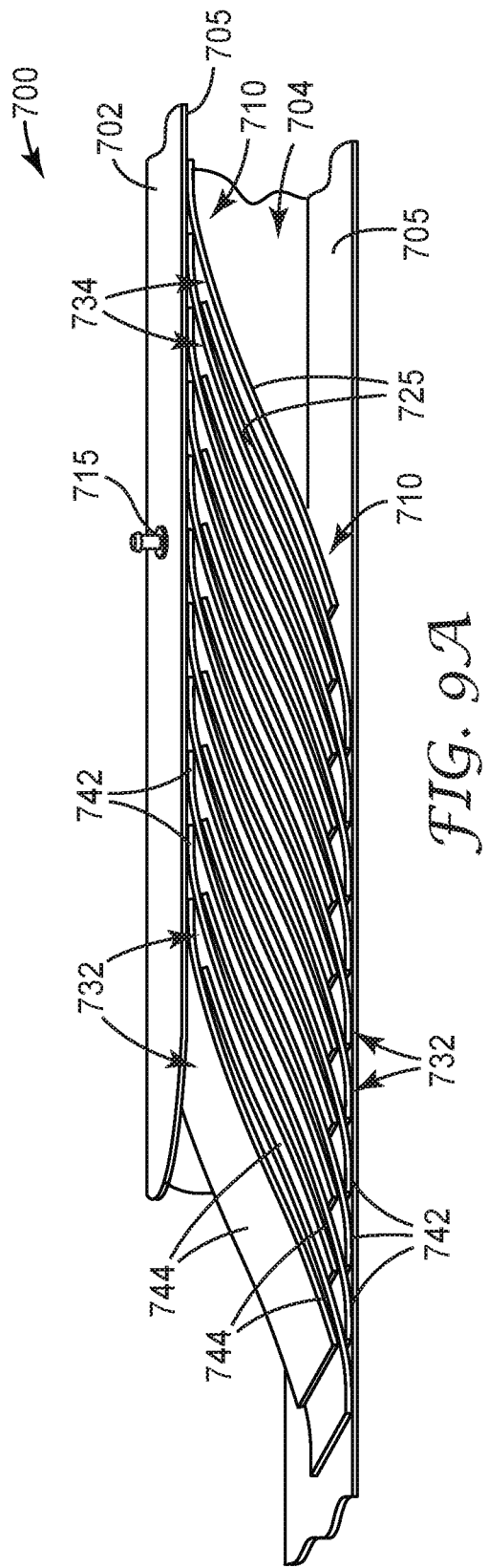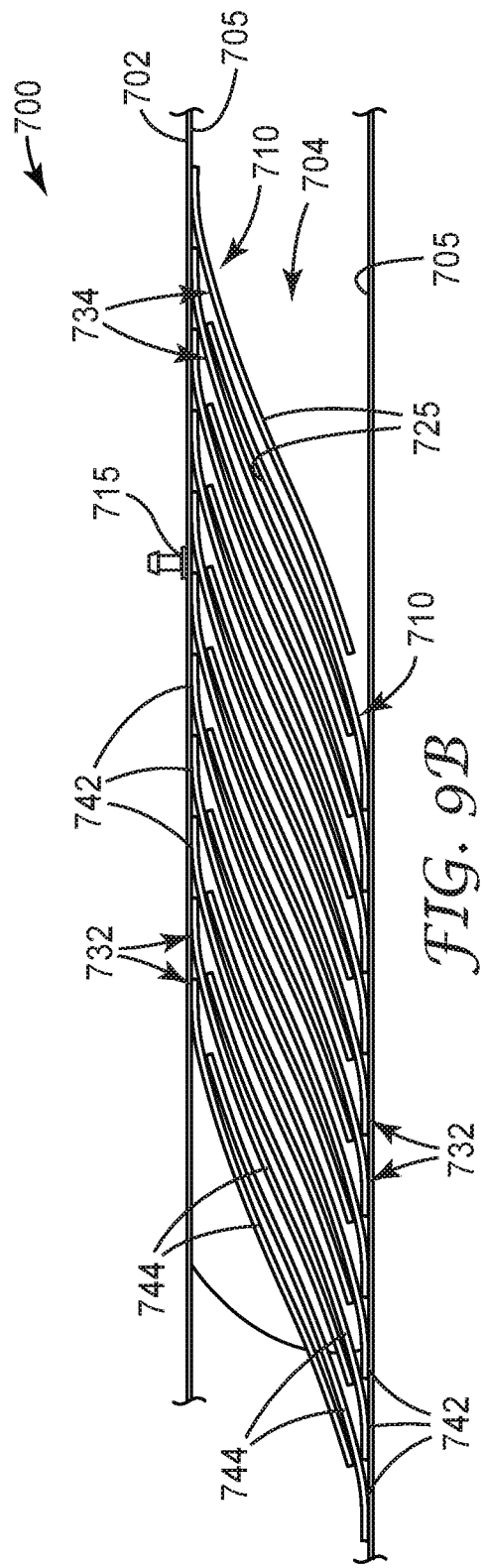

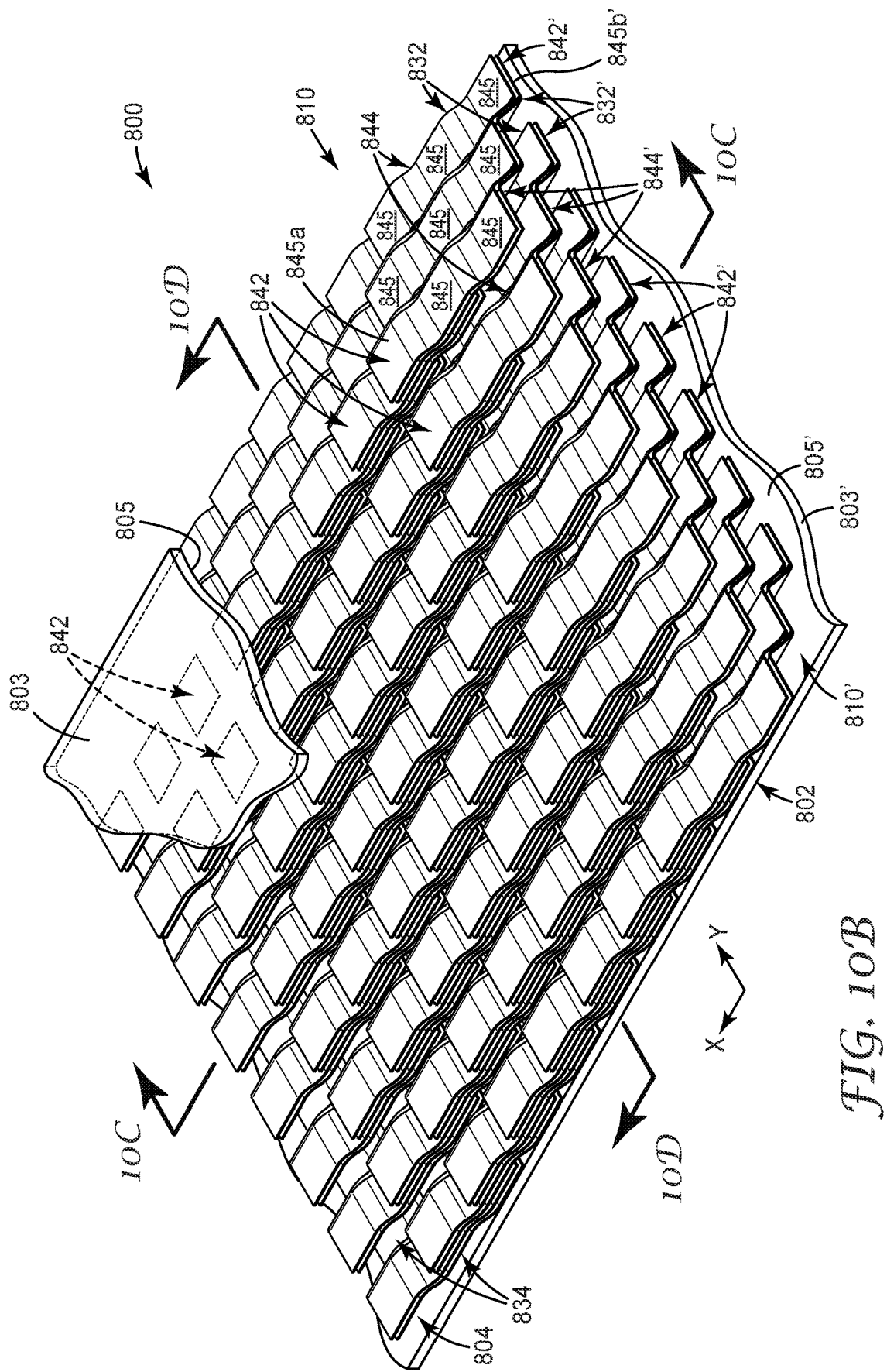

SHAPE-FORMABLE APPARATUS COMPRISING LOCKING SHEETS

CROSS REFERENCE TO RELATED APPLICATIONS

This is a national stage filing under 35 U.S.C. 371 of PCT/US2015/065494, filed on Dec. 14, 2015, which claims priority to U.S. Provisional Application No. 62/094240, filed on Dec. 19, 2014, the disclosure of which are incorporated by reference in their entirety herein.

FIELD

The present disclosure generally relates to shape-formable apparatuses that are configured to be formed into a desired shape and then held in the desired shape, and particularly, to shape-formable apparatuses comprising a plurality of locking sheets.

BACKGROUND

A variety of applications could benefit from a material or device having a stiffness that can change from a first (flexible) state, in which the material is shape-formable to a desired shape, to a second (more rigid) state, in which the desired shape can be held or fixed.

Some existing shape-formable devices employ discrete particles (i.e., bulk media) in a gas impermeable envelope that normally move freely with respect to one another, but "jam" together and resist relative motion when the internal pressure of the envelope is reduced below ambient pressure. This jamming of bulk media has been proposed for a variety of products, from a medical restraint for babies (U.S. Pat. No. 4,885,811) to limb demobilization (U.S. Pat. No. 4,657,003), to the stabilization of patients during surgery (U.S. Pat. No. 6,308,353), to robotic end effectors (U.S. Publication No. 2010/0054903). One significant disadvantage of bulk media jamming is the significant volume required for a bulk media-filled device. The bulk media does not lend itself well to thin, sheet-like, applications.

Other existing devices or systems employ bending stiffness variation in a thin form factor. By putting sheets of material in an envelope and removing air from the envelope (e.g., as in U.S. Publication No. 2012/0310126 and Ou et al., "jamSheets: Thin Interfaces with Tunable Stiffness Enabled by Layer Jamming," TEI '14 Proceedings of the 8th International Conference on Tangible, Embedded and Embodied Interaction, pages 65-72, Association for Computing Machinery (ACM), February 2014), a relatively thin article can be achieved with a variable bending stiffness. They achieve a low bending stiffness in an unjammed state, despite having a high Young's Modulus (or tensile modulus), by allowing multiple thin layers of material to slide over each other. However, because these individual layers each have a high overall Young's Modulus, even in an unjammed state, and they are substantially continuous in one or more axes within the plane, they cannot be easily extended within the plane, or major surface, of the thin article. Because the individual layers lack this extensibility, the conformability of the layers is also limited. Thus, these layers can only take on complex shapes by generating wrinkles, and not by smoothly and continuously assuming arbitrary shapes. The bending stiffness of these systems can increase under vacuum, because the multiple layers jam together and behave more like a single thick layer of the high Young's Modulus material.

SUMMARY

The present disclosure is generally directed to shape-formable apparatuses comprising an envelope that defines a chamber, and at least two locking sheets positioned in the chamber that can jam together to resist relative movement when the pressure in the chamber is reduced below ambient pressure. The locking sheets are each patterned into solid and open regions in such a way that the solid regions can move relative to one another in a major surface of the locking sheet, allowing the locking sheets to extend within the major surface, and thereby increase the conformability (i.e., in two or more axes) of the locking sheet. The solid regions can be discrete and separated from adjacent solid regions, and/or the solid regions can be connected to adjacent solid regions (i.e., continuous), for example, through a path or bridge (e.g., a long and/or tortuous path) that allows for relative motion between the solid regions within a major surface of the sheet. When the chamber is under vacuum, the locking sheets can jam together to increase the rigidity or stiffness (e.g., one or more of bending stiffness (e.g., effective bending modulus), tensile stiffness (e.g., effective tensile modulus), and indentation stiffness (e.g., effective indentation modulus)) of the apparatus.

Some aspects of the present disclosure provide a shape-formable apparatus having a first state in which the apparatus is formable, such that the apparatus can be formed into a desired shape; and a second state in which the apparatus has the desired shape and is substantially less formable than in the first state. The apparatus can further include an envelope defining a chamber, the envelope formed of a gas-impermeable material, and a port positioned to fluidly couple the chamber with ambience. The apparatus can further include at least two locking sheets positioned in the chamber in an at least partially overlapping configuration, wherein each locking sheet comprises a major surface, and wherein at least a portion of each locking sheet is patterned to include solid regions and open regions, the solid regions being movable with respect to one another within the major surface.

Other features and aspects of the present disclosure will become apparent by consideration of the detailed description and accompanying drawings.

BRIEF DESCRIPTION OF THE DRAWINGS

FIG. 9A is a partial perspective view of a shape-formable apparatus according to another embodiment of the present disclosure, employing locking sheets comprising overlapping discrete solid regions.

FIG. 9B is a schematic partial cross-sectional view of the shape-formable apparatus of FIG. 9A.

FIG. 10B is a partial perspective view of a shape-formable apparatus according to another embodiment of the present disclosure, the apparatus employing discrete solid regions of FIG. 10A that overlap along two axes.

DETAILED DESCRIPTION

Figure 1:
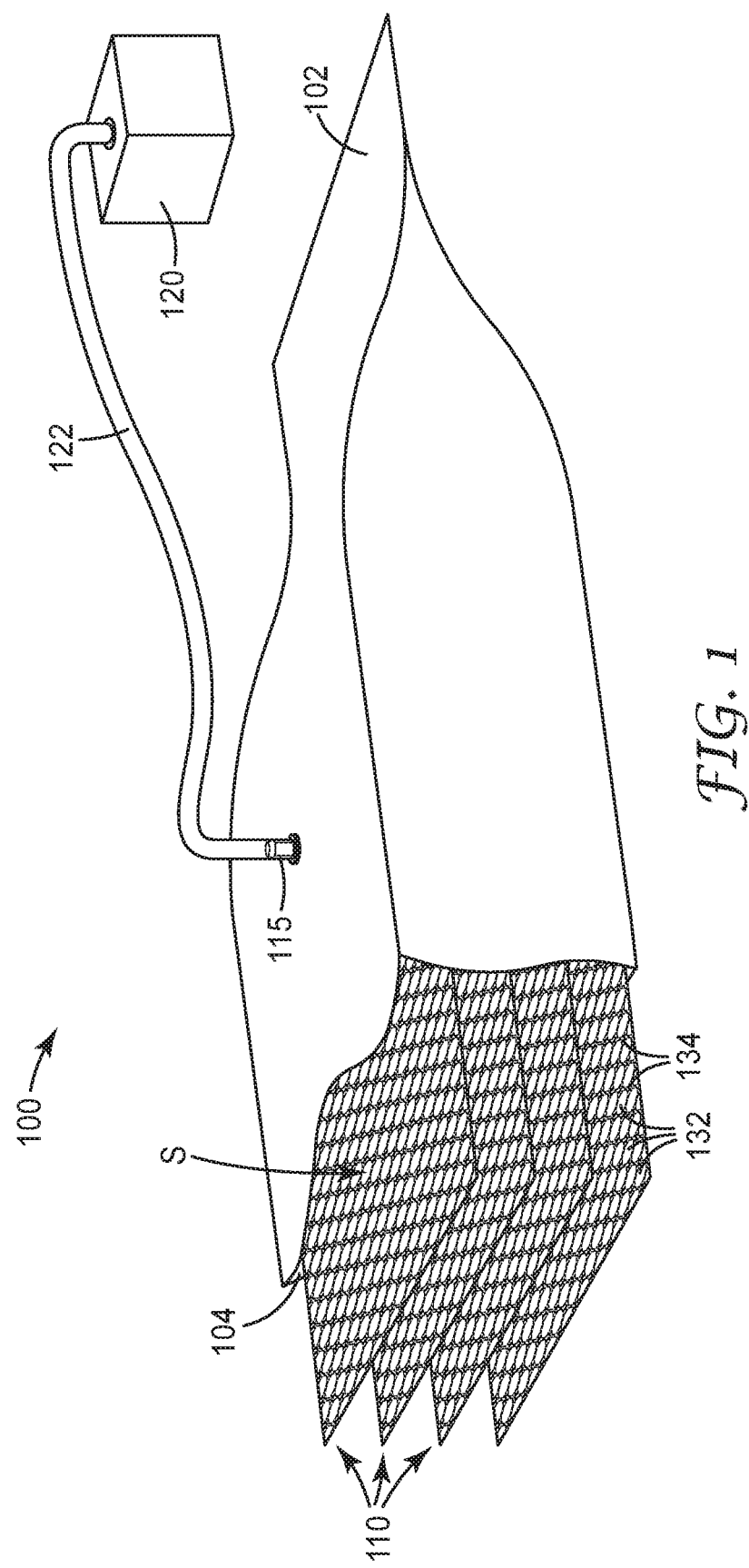
FIG. 1 is a cutaway perspective view of a shape-formable apparatus according to one embodiment of the present disclosure, employing locking sheets comprising continuous solid regions.

The present disclosure generally relates to a shape-formable apparatus comprising an envelope that defines an internal chamber, and at least two overlapping locking sheets positioned in the chamber. Each locking sheet can be patterned into solid regions and open regions (i.e., gaps or spaces between solid regions), such that at least some of the solid regions can move relative to one another within a major surface of the sheet. The apparatus has a first state in which the apparatus is formable and is able to be changed into a desired three-dimensional shape. The apparatus is further configured to be changed from the first state into a second state in which the three-dimensional shape of the apparatus is substantially fixed or rigid (or at least substantially less formable or more rigid than in the first state), such that the shape can be maintained for a desired purpose. The apparatus can be changed from the first state to the second state by evacuating the chamber to reduce the pressure in the chamber to below ambient pressure and to remove gas (e.g., substantially all of the gas) from the chamber. The apparatus can be changed from the second state to the first state by releasing the reduced pressure in the chamber and allowing it to return to ambient pressure. The apparatus can include an opening or a port that provides fluid communication between the chamber and ambience, such that a vacuum source can be coupled to the port via a connector (e.g., tubing).

The shape-formable apparatuses of the present disclosure can be used for a variety of applications that can benefit from a material or article that can be changed from a formable state, in which it can be formed into a desired shape, to a rigid or non-formable state, in which the desired shape can be essentially locked for as long as desired. Examples of such applications, include, but are not limited to, surgical access retraction, tissue or organ retraction, patient positioning (e.g., to maintain a patient in a desired position during treatment, therapy, surgery, etc.), packaging (e.g., to hold, separate and/or protect objects during shipping), home and office storage, organization, and/or display (e.g., modular shelving, drawer separators, etc.), immobilization (e.g., casts to immobilize limbs or joints), other suitable applications, or combinations thereof.

Methods of using shape-formable apparatuses, e.g., for tissue manipulation, are described in U.S. Application Nos. 62/094,279, filed Dec. 19, 2014, and 62/094,336, filed Dec. 19, 2014, which are each incorporated herein by reference in their entirety. In addition, other shape-formable apparatuses are described in U.S. Application No. 62/094,299, filed Dec. 19, 2014, which is incorporated herein by reference in its entirety.

As described above, unlike some existing shape-formable devices, the shape-formable apparatuses of the present disclosure take up substantially less three-dimensional space, or volume, due to their substantially sheet-like or plate-like configuration. Some existing shape-formable devices are filled with beads or other particulate or "bulk" matter or media. The sheet-like apparatuses of the present disclosure can overcome several disadvantages present with existing "bulk" or non-sheet-like devices, including, but not limited to: (i) bulk apparatuses require significant three-dimensional size or space to conform to desired shapes (e.g., to cover or form around an object), with a nominal spherical form factor and relatively large cross-sectional areas; (ii) bulk apparatuses can only apply low forces to an object; (iii) bulk apparatuses are strongest in compressive forces; and (iv) bulk apparatuses do not easily conform to a desired object or take a desired three-dimensional shape without exerting significant force on the object.

Definitions

The term "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the term "coupled" and variations thereof are used broadly and encompass both direct and indirect couplings.

The terms "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

A "low friction" surface can generally be used to refer to a surface having a low kinetic coefficient of friction. In some embodiments, a low friction surface can include a kinetic coefficient of friction of no greater than about 1, in some embodiments, no greater than about 0.5, and in some embodiments, no greater than about 0.25, when measured on a flat film, sliding against another piece of the same material in accordance with ASTM D1894-08 Static and Kinetic Coefficients of Friction of Plastic Film and Sheeting.

A "high friction" surface can generally be used to refer to a surface having a high kinetic coefficient of friction, e.g., when describing a locking sheet alone or relative movement between locking sheets when the apparatus is in the first state. This friction can be achieved through properties of the surface material, or through physical structuring of the surface (e.g. 3M™ Gripping Material, available from 3M Company, St. Paul, Minn.; www.3 m.com/gripping). In some embodiments, a high friction surface can include a kinetic coefficient of friction of at least about 1, in some embodiments, at least about 3, and in some embodiments, at least about 10, when measured on a flat film, sliding against another piece of the same material in accordance with ASTM D1894-08 Static and Kinetic Coefficients of Friction of Plastic Film and Sheeting.

The phrases "sheet," "sheet-like," "sheet-like configuration," "plate," "plate-like," "plate-like configuration," or variations thereof, are used to describe an article having a thickness that is small relative to its length and width. The length and width of such articles can define a "major surface" of the article, but this major surface, as well as the article, need not be flat or planar. For example, the above phrases can be used to describe an article having a first ratio ($R_1$) of thickness (e.g., in a Z direction that is orthogonal to a major surface of the article at any point along the major surface) to a first surface dimension of the major surface (e.g., width or length), and a second ratio ($R_2$) of thickness to a second surface dimension of the major surface, where the first ratio ($R_1$) and the second ratio ($R_2$) are both less than 0.1. In some embodiments, the first ratio ($R_1$) and the second ratio ($R_2$) can be less than 0.01; in some embodiments, less than 0.001; and in some embodiments, less than 0.0001. Note that the two surface dimensions need not be the same, and the first ratio ($R_1$) and the second ratio ($R_2$) need not be the same, in order for both the first ratio ($R_1$) and the second ratio ($R_2$) to fall within the desired range. In addition, none of the first surface dimension, the second surface dimension, the thickness, the first ratio ($R_1$), and the second ratio ($R_2$) need to be constant in order for both the first ratio ($R_1$) and the second ratio ($R_2$) to fall within the desired range.

The phrase "major surface" is used to refer to a collective surface of an article (e.g., an outer surface of the article), even if the article is formed of smaller objects or portions. The smaller objects and portions can collectively define a major surface of the article. While such a major surface can be planar in some instances, the major surface need not be flat or planar, and in some cases, can be curved or otherwise complex. The phrase "major surface" is described in greater detail below with respect to the locking sheets 110 of FIGS. 1, 4 and 5.

The phrase "substantially parallel" is used to refer to at least two sheets or sheet-like articles having a major surface, where the major surface of the sheets or articles are oriented parallel with respect to one another at any point along their respective major surfaces, but allowing for a slight deviation from parallel. For example, if two sheets have major surfaces that lie in an X-Y plane and are spaced a distance apart in a Z direction that is orthogonal, or normal, to the X-Y plane, the two sheets can be considered substantially parallel even if one or both of the sheets has a major surface that is oriented slightly out of an orthogonal relationship with the Z direction at a given point, or area, along the major surface. In some embodiments, the two sheets can be substantially parallel if one or both of the sheets has a major surface that extends in the Z direction by an amount (i.e., has a Z dimension because the major surface is tilted with respect to the Z direction) that is no greater than 10% of its dimensions in the X-Y plane; in some embodiments, no greater than 5%; in some embodiments, no greater than 2%; and in some embodiments, no greater than 1%. Note that two sheets can still be substantially parallel even if the sheets are not flat or planar. For example, two curved sheets can be substantially parallel if the two sheets are curved to the same degree and in the same way so that the orientation of the major surfaces of the two sheets, relative to a normal direction at any point, or area, along the major surface, still falls within the above ranges.

The terms "polymer" and "polymeric material" refer to both materials prepared from one monomer such as a homopolymer or to materials prepared from two or more monomers such as a copolymer, terpolymer, or the like. The terms "copolymer" and "copolymeric material" refer to a polymeric material prepared from at least two monomers.

The terms "room temperature" and "ambient temperature" are used interchangeably to mean a temperature in the range of 20° C. to 25° C.

The term "effective tensile modulus" (ETM), which is described in greater detail below, refers to the slope of the line in a plot of tensile force per unit width versus strain (extension divided by original length), as tested according to the procedure described below in the Examples section.

The term "effective bending modulus" (EBM), which is described in greater detail below, refers to the slope of the line in a plot of tensile force per unit width versus a dimensionless approximation of deflection angle when a sample is pulled on to induce bending according to the procedure described below in the Examples section.

The term "effective indentation modulus" (EIM) refers to the slope of the line in a plot of the applied force versus deflection distance when a sample is tested according to the procedure described below in the Examples section called Effective Indentation Modulus.

FIG. 1 illustrates a shape-formable apparatus 100 according to one embodiment of the present disclosure. The apparatus 100 is generally sheet-like or plate-like, or has a sheet-like or plate-like configuration, as opposed to a three-dimensionally bulky configuration.

As shown in FIG. 1, the apparatus 100 can include an envelope (or shell, or pouch) 102 that defines an internal chamber 104; at least two adjacent locking sheets 110 positioned in the chamber 104 in an at least partially overlapping and substantially parallel configuration; and a port, or opening, 115 in the envelope 102 that is positioned to fluidly couple the chamber 104 with ambience, and through which the chamber 104 can be evacuated, e.g., by being coupled to a vacuum source 120.

For clarity purposes, the top and bottom sides of the envelope 102 are illustrated in FIG. 1 as being substantially spaced apart (i.e., with a sidewall joining them). Similarly, the locking sheets 110 are illustrated as being substantially spaced apart from one another. However, it should be understood that this illustration is used merely to better and more clearly show how the locking sheets 110 can stack with respect to one another and can be positioned in the chamber 104. In reality, the apparatus 100 can appear much flatter, having a sheet-like or plate-like configuration.

The apparatus 100 can be configured to be formed into, and held in, a desired shape. That is, the apparatus 100 can have a first state in which the apparatus 100 is formable (as further described below), such that the apparatus 100 can be formed into a desired three-dimensional shape (e.g., exhibiting a non-zero Gaussian curvature, as described below).

The apparatus 100 can also have a second state in which the apparatus 100 has the desired shape and is substantially rigid, or at least substantially more rigid than in the first state, and in which the desired shape is held or locked (i.e., substantially non-formable).

As a result, the apparatus 100 is formable, deformable, conformable, and/or manipulatable in the first state, and substantially not formable, deformable, conformable, and/or manipulatable in the second state. Terms such as formable, deformable, conformable, and/or manipulatable can be used when describing the ability of the apparatus 100 to take any desired shape in the first state, the opposite being true when the apparatus 100 is in the second state.

In order to take on any desired three-dimensional shape and be "formable" according to the present disclosure (in the first state), the apparatus 100 exhibits both flexibility (or bendability) and extensibility. For example, a solid sheet of high tensile modulus (e.g., Young's modulus) material would not be considered to be "formable," according to the present disclosure, because while it may be bent, it cannot be extended under similar amounts of force (e.g., under reasonable amounts of force, such as forces that can be applied by hand). Generally, an apparatus can exhibit formability when the scale of forces (whether manual or otherwise) required to achieve bending are comparable to the forces required for extension. For example, if it is desirable for about 10-50 lb (45-224 N) of force to cause bending of the apparatus, then it should take about 10-50 lb (45-224 N) of force to cause extension of the apparatus. A typical sample of material (modeled simplistically as a rectangular beam of thickness t, width w, and length L, simply supported at two ends) would bend to a maximum deflection of $$\delta_{bend} = \frac{FL^3}{4Ewt^3}$$

(where L is the length of the beam, and E is the Young's Modulus). That same sample of material would extend by $$\delta_{ext} = \frac{FL}{Ewt}.$$

The only way to have $\delta_{bend} \sim \delta_{ext}$ for this solid material is if L~2t, which is not a sheet or "sheet-like" according to the present disclosure.

For simplicity, the first state can be described as a state in which the apparatus 100 is formable or in which the shape (e.g., the three-dimensional shape) of the apparatus 100 is changeable or unlocked; and the second state can be described as a state in which the apparatus 100 is "rigid," or in which the shape (e.g., the three-dimensional shape) of the apparatus 100 is fixed or locked.

The apparatus 100 can be changed into the second state by using the vacuum source 120 to evacuate the chamber 104 (i.e., to remove gas from the chamber 104). After the apparatus 100 has been formed into its desired shape and changed from the first state to the second state, the port 115 (or a connector 122, described below) can be sealed and/or disconnected from the vacuum source 120, and the apparatus 100 can remain in the second state in the desired shape.

Figure 2A:
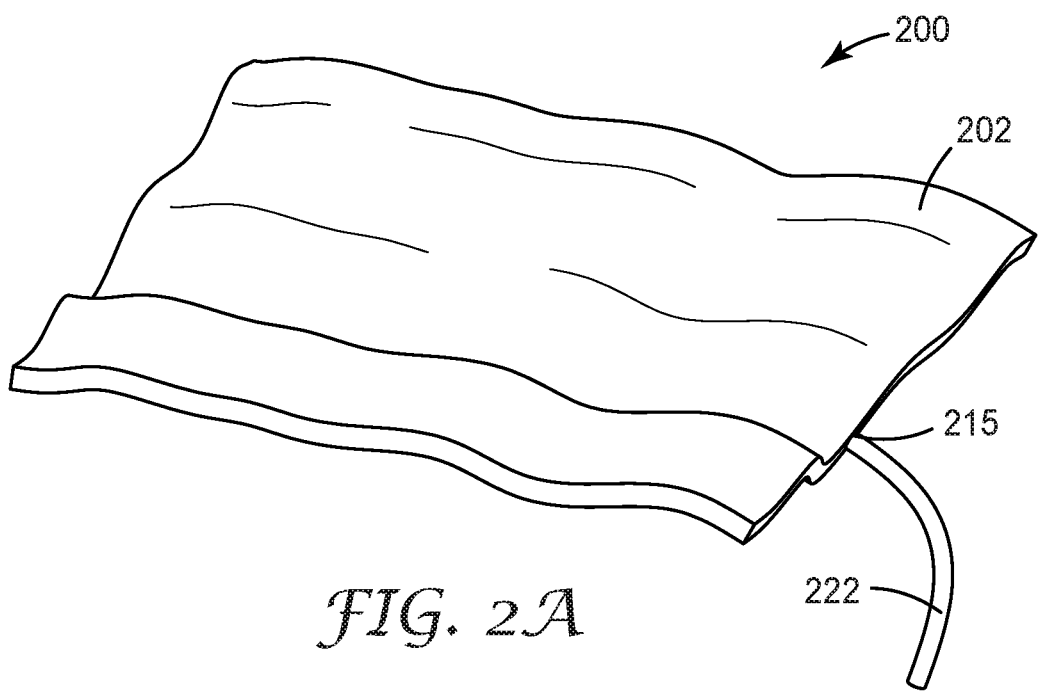
FIG. 2A is a perspective view of a shape-formable apparatus according to another embodiment of the present disclosure, shown in a first state.
Figure 2B:
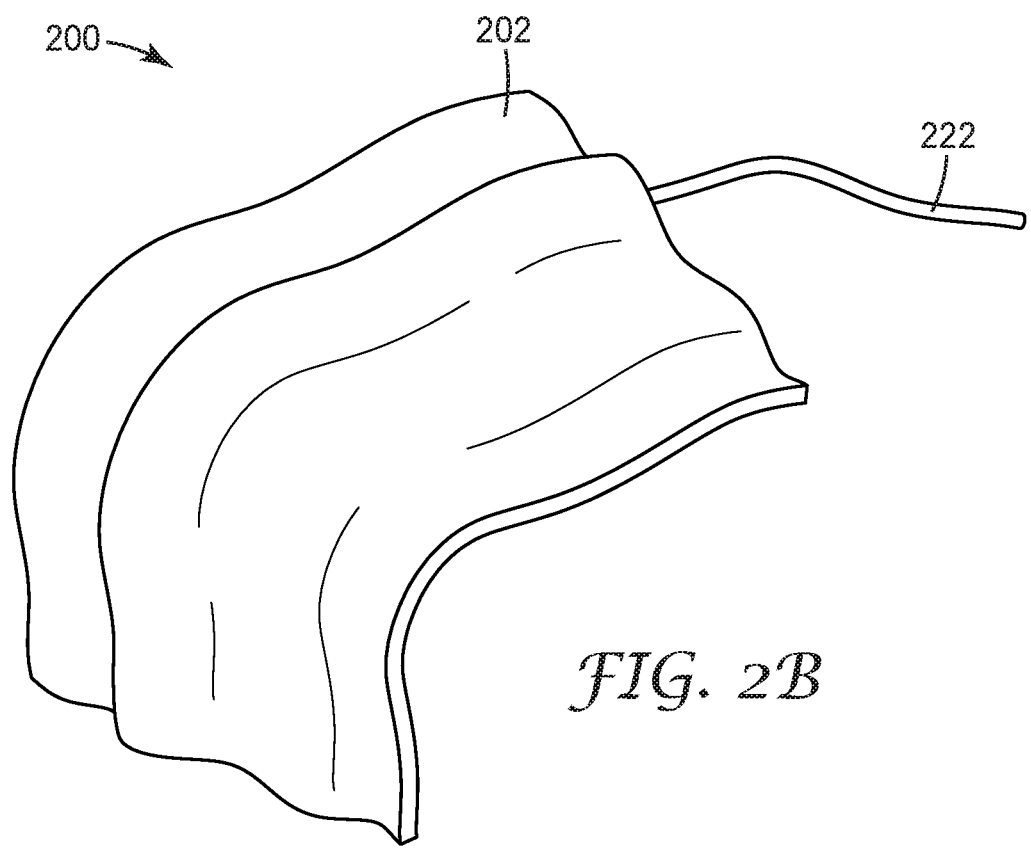
FIG. 2B is a perspective view of the shape-formable apparatus of FIG. 2A, shown in a second state.

FIGS. 2A-2B illustrate a shape-formable apparatus 200 according to another embodiment of the present disclosure, the apparatus 200 being sheet-like. Locking sheets (not shown) of the present disclosure are contained within a chamber defined by an envelope 202. The chamber (not shown) can be evacuated via an opening 215 and a connector 222, e.g., by connecting the connector 222 to a vacuum source (not shown). FIG. 2A shows the apparatus 200 in a first state in which the chamber inside, and defined by, the envelope 202 is not evacuated (i.e., is not reduced significantly below ambient pressure). The apparatus 200 can be formed into a desired shape (i.e., three-dimensional shape) while in the first state. FIG. 2B shows the apparatus 200 after it has been formed into a desired shape and changed from the first state to the second state to "lock" (i.e., reversibly lock) the apparatus 200 in the desired shape. The connector 222 is shown in FIGS. 2A and 2B as being integrally formed with the envelope 202, such that the connector 202 is still coupled to the envelope 202 in the second state (FIG. 2B), but this need not be the case.

Figure 3A:
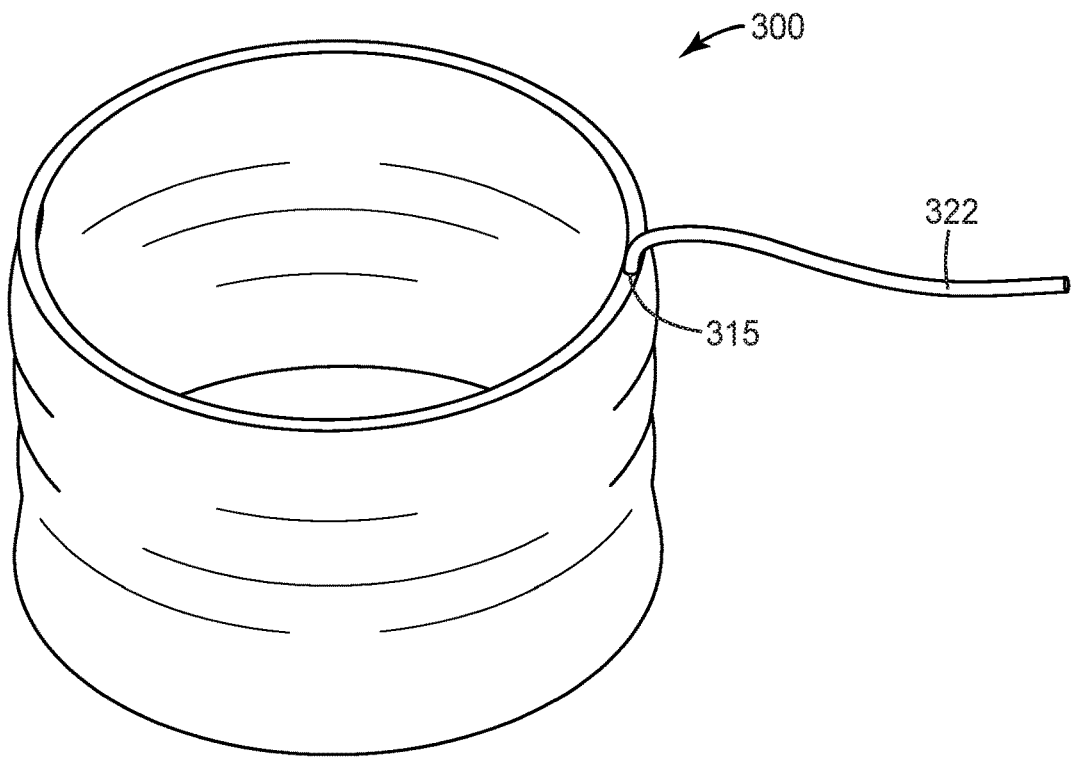
FIG. 3A is a perspective view of a shape-formable apparatus according to another embodiment of the present disclosure, shown in a first state.
Figure 3B:
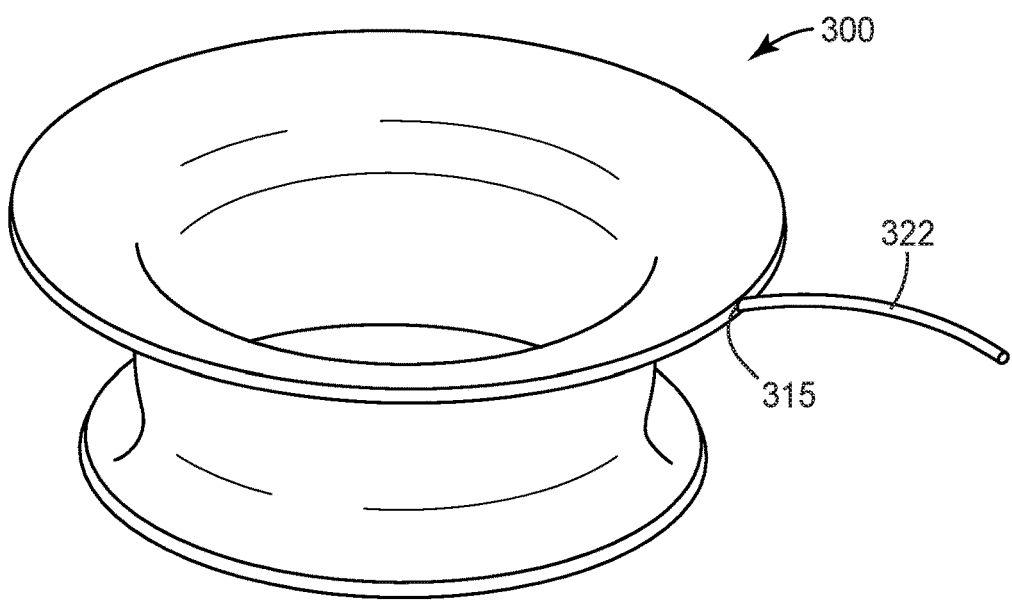
FIG. 3B is a perspective view of the shape-formable apparatus of FIG. 3A, shown in a second state.

Similarly, FIGS. 3A-3B illustrate a shape-formable apparatus 300 according to another embodiment of the present disclosure, the apparatus 300 still being sheet-like, but having a tubular configuration. Locking sheets (not shown) of the present disclosure are contained within a chamber defined by an envelope 302 and can be oriented substantially parallel with the tubular surfaces of the envelope 302. The locking sheets can also be tubular, or one or more locking sheets can be positioned about the tube (e.g., end to end or with ends overlapping). A single long locking sheet can also be wound around itself multiple times to create many layers in a tubular shape. The envelope 302 can be evacuated via an opening 315 and a connector 322, e.g., by connecting the connector 322 to a vacuum source (not shown). FIG. 3A shows the apparatus 300 in a first state in which the chamber inside, and defined by, the envelope 302 is not evacuated (i.e., is not reduced significantly below ambient pressure). The apparatus 300 can be formed into a desired shape (i.e., three-dimensional shape) while in the first state. FIG. 3B shows the apparatus 300 after it has been formed into a desired shape and changed from the first state to the second state to "lock" the apparatus 300 in the desired shape. The connector 322 is shown in FIGS. 3A and 3B as being integrally formed with the envelope 302, such that the connector 302 is still coupled to the envelope 302 in the second state (FIG. 3B), but this need not be the case.

The configurations of the apparatuses 200 and 300 of FIGS. 2A-2B and 3A-3B, respectively, are shown by way of example only. Any of the additional details described herein with respect to other embodiments of shape-formable apparatuses of the present disclosure can also be applied to the apparatuses 200 and 300, and vice versa.

While not shown in FIGS. 2A-3B, in some embodiments, apparatuses of the present disclosure can have an at least slightly reduced volume when in the second state, as compared to the first state. That is, in some embodiments, apparatuses of the present disclosure in the second state can be at least partially collapsed, relative to the first state. In sheet-like apparatuses of the present disclosure, the collapse may occur predominantly in the direction of the thickness of the apparatus (i.e., the Z direction), which is already small in the first state, relative to the surface dimensions (i.e., the dimensions defining a major surface of the apparatus).

The envelope 102 is generally formed of a gas-impermeable material. The envelope 102, or a portion thereof (e.g., at least a portion of an outer surface thereof), can be formed of a variety of materials, depending on the desired use of the apparatus 100. Examples of suitable envelope materials include, but are not limited to, composite materials, polymeric materials (e.g., elastomeric, thermoplastic, thermoset, biodegradable, or combinations thereof), or combinations thereof. In some embodiments, the envelope 102, or a portion thereof (e.g., at least a portion of an outer surface thereof), can be formed of an impermeable (e.g., liquid and gas-impermeable), non-absorbent, microporous, and/or non-porous material that is resistant to harboring bacteria and other soil. As a result, the envelope 102, or the respective portion thereof, can be easily cleaned and/or disinfected. In addition, in some embodiments, the envelope 102, or a portion thereof, can include an antimicrobial layer or coating to inhibit microbes from collecting and/or growing on the envelope 102. In some embodiments, the envelope 102 can be formed of materials that are compatible with common disinfectants and cleaners, such as oxidizers (e.g., bleach, hydrogen peroxide, dilute peracetic acid, and the like), quaternary ammonium disinfectants (e.g. dimethyldidecylammonium bromide), phenolic compounds (e.g. triclosan), cleaning surfactants (e.g. sodium dodecyl sulfate), as well as solvents (e.g. glycol ethers such as hexyl Cellosolve or hexylCarbitol).

In some embodiments, the envelope 102 can be formed of an elastomeric material that is highly extensible and conformable, such that the overall extensibility or conformability of the apparatus 100 is not limited by the envelope 102. Said another way, the extensibility and the conformability of the envelope 102 is at least that of one locking sheet 110, or at least that of the plurality of locking sheets 110. More specifically, in some embodiments, the envelope 102 can have a tensile modulus (e.g., Young's modulus, or an effective tensile modulus as set forth in the Examples), a bending modulus (e.g., an effective bending modulus, as set forth in the Examples), and/or an indentation modulus (e.g., an effective indentation modulus, as set forth in the Examples) that is less than one locking sheet 110, or less than the plurality of locking sheets 110.

In some embodiments, the envelope 102 can exhibit an Effective Tensile Modulus (e.g., as tested according to the test method described in the Examples section) of no greater than 5 N/mm; in some embodiments, no greater than 3 N/mm; in some embodiments, no greater than 1.5 N/mm; in some embodiments, no greater than 1 N/mm; in some embodiments, no greater than 0.5 N/mm; and in some embodiments, no greater than 0.1 N/mm. The envelope used in the Examples below was tested by itself according to the method described in the 'Test Procedures' section of the Examples, and was found to have an Effective Tensile Modulus of 1.21 N/mm.

Examples of elastomeric materials can include silicones, polydimethylsiloxane (PDMS), liquid silicone rubber, poly (styrene-butadiene-styrene), other suitable thermoplastic elastomers, and combinations thereof.

Examples of thermoplastic materials can include one or more of polyolefins (e.g., polyethylene (high density polyethylene (HDPE), medium density polyethylene (MDPE), low density polyethylene (LDPE), linear low density polyethylene (LLDPE)), metallocene polyethylene, and the like, and combinations thereof), polypropylene (e.g., atactic and syndiotactic polypropylene)), polyamides (e.g. nylon), polyurethane, polyacetal (such as Delrin), polyacrylates, and polyesters (such as polyethylene terephthalate (PET), polyethylene terephthalate glycol (PETG), and aliphatic polyesters such as polylactic acid), fluoroplastics (such as THV from 3M company, St. Paul, Minn.), and combinations thereof.

Examples of thermoset materials can include one or more of polyurethanes, silicones, epoxies, melamine, phenol-formaldehyde resin, and combinations thereof.

Examples of biodegradable polymers can include one or more of polylactic acid (PLA), polyglycolic acid (PGA), poly(caprolactone), copolymers of lactide and glycolide, poly(ethylene succinate), polyhydroxybutyrate, and combinations thereof.

In embodiments employing a polymeric envelope 102, the envelope 102 can be formed by a variety of methods, including relatively facile manufacturing methods, such as extrusion, molding, or combinations thereof.

In some embodiments, one or more surfaces of the envelope 102 (e.g., an outer surface thereof), or a portion thereof, can include a low friction surface, which can be achieved by the material composition and/or texture of the respective surface or by treating the surface (e.g., with a coating, or by coupling a low-friction layer to a desired portion of the envelope 102, etc.).

In some embodiments, the apparatus 100 can be in the first state when the internal pressure within the chamber 104 is equal to ambient pressure (e.g., about 101 kPa at sea level), or is within +/−5% of ambient pressure. However, the chamber 104 can be at least partially evacuated (e.g., by coupling the port 115 to the vacuum source 120 and evacuating the chamber 104, i.e., removing gas from the chamber 104) to change the apparatus 100 to the second state, in which the internal pressure within the chamber 104 is reduced below ambient pressure (e.g., greater than 5% below ambient pressure).

The vacuum source 120 is only shown schematically in FIG. 1, but it should be understood that a variety of suitable vacuum sources can be coupled to the apparatus 100. For example, the vacuum source 120 can include, but is not limited to, one or more of a mechanical pump, a manual pump such as a syringe-plunger combination, other suitable vacuum sources that can reduce the pressure in the chamber 104, or a combination thereof.

The vacuum source 120 is shown by way of example only as being coupled to the port 115 of the apparatus 100 by a connector 122. The connector 122 is illustrated as tubing by way of example. In some embodiments, one or both of the connector 122 and the vacuum source 120 can be considered to form a portion of the apparatus 100 (e.g., the envelope 102 can be integrally formed with or include the connector 122); however, in some embodiments, the apparatus 100 can be considered to be coupled to one or both of the connector 122 and the vacuum source 120.

The locking sheets 110 are illustrated in FIG. 1 as forming a stack of locking sheets 110. The stack is shown as including four locking sheets 110 for simplicity and by way of example only. However, it should be understood that as few as two locking sheets and as many as structurally possible can be employed in apparatuses of the present disclosure. While the locking sheets 110 of FIG. 1 are shown as discrete sheets in a stack, it should be understood that "at least two locking sheets" generally means at least two overlapping sections or portions of locking sheets, and the overlapping sections or portions need not actually be discrete sheets, but rather, could be sections or portions of one long locking sheet that are layered over one another, e.g., by zig-zagging the long sheet, by coiling the sheet, or by otherwise arranging the long sheet such that it includes at least two overlapping portions or sections. For simplicity, this will be described as "at least two locking sheets" herein and in the appended claims.

The number of locking sheets 110 can be selected to be a number that provides sufficient formability of the apparatus 100 in the first state, while also providing sufficient rigidity in the second state for a given application. In some embodiments, the number of locking sheets 110 employed can depend on the material makeup and the thickness of each locking sheet 110.

The locking sheets 110 of the present disclosure can be formed of a variety of materials, depending on the desired application or use of the apparatus 100. Examples of suitable locking sheet materials include, but are not limited to, paper; a metal, which can be annealed for enhanced malleability (e.g., steel, aluminum); a polymeric material (e.g., ABS, or Delrin), a composite material (e.g., carbon fiber); other similar suitable materials, and combinations thereof.

In some embodiments, the locking sheets 110 can all be formed of the same material; however, the locking sheets 110 employed in one apparatus 100 need not all be formed of the same materials. In some embodiments, some of the locking sheets 110 are formed of the same materials, while other locking sheets 110 are formed of one or more different materials. In some embodiments, the locking sheets 110 can be arranged (e.g., stacked) in the chamber 104 according to material makeup, such as in an alternating configuration. For example, in some embodiments, a locking sheet 110 formed of a first material can be positioned adjacent a locking sheet 110 of a second material, which can be positioned adjacent a locking sheet 110 of the first material, and so on. However, in some embodiments, locking sheets 110 of different materials can be arranged in other configurations, or even randomly, in the chamber 104.

In some embodiments, the locking sheets 110 can all have the same thickness (i.e., in a Z direction that is orthogonal to the major surface of the locking sheet 110); however, in some embodiments, the locking sheets 110 employed in one apparatus 100 need not all have the same thicknesses. In some embodiments, some of the locking sheets 110 can have the same thickness, while other locking sheets 110 have one or more different thicknesses. In some embodiments, the locking sheets 110 can be arranged (e.g., stacked) in the chamber 104 according to thickness, for example, in order of increasing thickness, decreasing thickness, alternating thickness, another suitable configuration, or a combination thereof. However, in some embodiments, the locking sheets 110 having different thicknesses can be arranged randomly in the chamber 104.

In addition, in some embodiments, one or more locking sheets 110 can have a varying thickness, such that the thickness is not constant throughout the locking sheet 110.

In some embodiments, the locking sheets 110 can be formed by a variety of methods, including but not limited to, extrusion, molding, laser cutting, water jetting, machining, stereolithography or other 3D printing, laser ablation, photolithography, chemical etching, rotary die cutting, stamping, other suitable negative or positive processing techniques, or combinations thereof.

When the apparatus 100 is in the first state, the locking sheets 110 can be formable, and can slide relative to one another, i.e., such that the major surfaces of adjacent locking sheets 110 slide past one another (e.g., in X and Y directions), and can also move relative to one another in a Z direction that is orthogonal to any point along the major surfaces of the locking sheets 110. However, when the apparatus 100 is in the second state (i.e., when the chamber 104 is evacuated), the locking sheets 110 can be substantially immovable or "locked" relative to one another, in the surface (e.g., X and Y) and Z directions, such that the apparatus 100 is "substantially/essentially immovable" or "substantially/essentially locked."

A "substantially/essentially immovable" or "substantially/essentially locked" apparatus 100 can also be referred to as "substantially rigid," "substantially more rigid than in the first state," or "substantially less formable than in the first state," and, in some embodiments, can be characterized by comparing a material property (e.g., a measure of stiffness, such as tensile modulus) of the apparatus 100 when the apparatus 100 is in the second (locked) state with the same material property of the apparatus 100 when the apparatus 100 is in the first (unlocked) state, as described in greater detail below.

As further shown in FIG. 1, at least a portion of each locking sheet 110 can be patterned or segmented into solid regions 132 and open regions 134 (i.e., gaps or free spaces between solid regions 132), such that at least some of the solid regions 132 are movable with respect to one another within a major surface S of the locking sheet 110. For simplicity and clarity of illustration, the locking sheets 110 of FIG. 1 are shown as having a solid outline; however, it should be understood that more likely, the edges of the locking sheets 110 will not be continuously solid and instead will be made up of the solid regions 132 and the open regions 134, and possibly incomplete portions of solid regions 132. For simplicity and clarity purposes, one locking sheet 110 will now be described in greater detail; however, it should be understood that the additional details described below can be applied to any locking sheet 110 of the apparatus 100.

Figure 4:
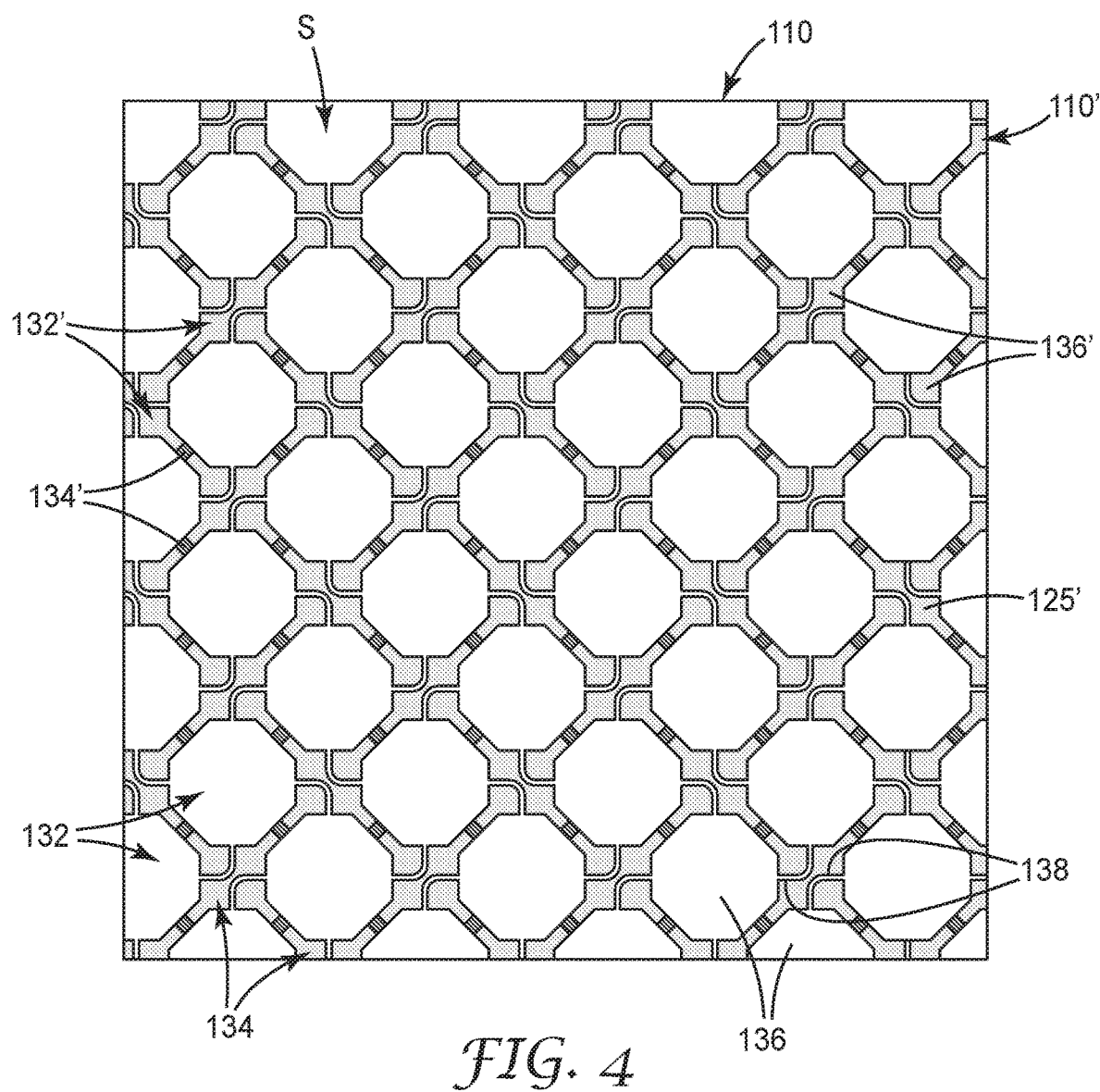
FIG. 4 is a top plan view of two locking sheets of FIG. 1, shown in a staggered configuration.

By way of example only, the top (or bottom) surfaces of the individual solid regions 132 of the first locking sheet 110 of FIG. 4 collectively define one or more major surfaces of the locking sheet 110. One exemplary major surface S is shown in FIGS. 1 and 4 and is shown as being substantially planar for simplicity, but as the locking sheet 110 is formed into a desired shape (e.g., by being formed over an object, or conforming to a complex surface), the major surface S can take on any complex shape. Such a complex shape can be possible, because the solid regions 132 are movable relative to one another within the major surface S. That is, the shape of the major surface S can change (e.g., due to the relative movement of the solid regions 132 defining the major surface S), and can be very complex. However, no matter what shape the major surface S has, the solid regions 132 can be movable relative to one another within the major surface S. Such movement can include bending relative to one another (e.g., deflecting in and out of the major surface S, but also redefining the major surface S in doing so), such that the resulting locking sheet 110 is bendable, and also moving toward and away from one another, such that the resulting locking sheet 110 is extensible. This combination of flexibility (bendability) and extensibility creates a formable locking sheet 110.

While it is understood that the solid regions 132 also have a thickness in a Z direction that is orthogonal to the major surface S, there will be a major surface (e.g., the major surface S) that is collectively defined by the solid regions 132, and the solid regions 132 will be movable within that major surface. The solid regions 132 may also be movable relative to one another into and out of that major surface, or relative to one another in the Z direction. However, a key distinguishing property of the locking sheets of the present disclosure are that they are patterned into solid regions and open regions in such a way that the solid regions are at least movable relative to one another within a major surface of the locking sheet 110.

The relative movement of solid regions 132 both in and out of a major surface of the locking sheet 110 allow the sheet to form into any spatial surface. For example, the locking sheet 110 could be smoothly formed around a sphere or even the contours of a human face without wrinkling. This is possible because the solid regions 132 can both bend and extend within the major surface relative to each other. The ability of a locking sheet 110 (or plurality of locking sheets 110) to morph into any desired spatial surface topology may be limited by the size and flexibility/extensibility of the solid regions 132, which defines a sort of spatial resolution of the locking sheet 110 that can be adjusted to suit the application.

Particularly, the solid regions 132 can move within the major surface relative to one another from a first position to a second position, and more particularly, can move relative to one another from a first position to a second position that can be maintained without any plastic deformation of the material forming the locking sheet 110. This is in contrast to a sheet of material in which openings have been cut such that material has simply been removed to form the sheet, or a sheet of material formed of woven pieces or strands of material. In such sheets, the openings may provide space for the solid portions to slightly move or wiggle relative to one another, but not from a first position to a second position that can be maintained without plastic deformation. For example, if the solid portions of such sheets are moved such that the stress applied extends the material within its elastic limit, the material will return to its first position as soon as the stress is removed; and if the material is moved such that the stress applied extends the material beyond its elastic limit, plastic deformation will occur. That is, if a sheet of material included only continuous strips or strands of material in one or more directions, the sheet's material properties in those one or more directions would be equal to the material properties of the material making up the continuous strips or strands. On the contrary, the locking sheets 110 of the present disclosure are formed of a material, but include different overall material properties than the properties of the material itself, and particularly, in any direction in which the material property is tested.

In some embodiments, relative motion of solid regions within a major surface can be characterized or quantified by material property ratios that compare a given material property for the material making up the solid regions 132 to an overall material property for the locking sheet 110 that results from the patterning or segmenting of the sheet into solid regions 132 and open regions 134. That is, a solid piece of material (e.g., steel, paper, etc.) will behave substantially differently from a locking sheet 110 of the present disclosure (i.e., having solid regions 132 and open regions 134) that is formed of that same material.

For example, the locking sheet 110 can be formed of a material having a first effective tensile modulus ($E_o$), and the solid regions 132 and open regions 134 can be arranged such that the locking sheet 110 has an overall effective tensile modulus ($E_l$; e.g., when tested in any or all surface directions within a major surface of the locking sheet 110), and the ratio of $E_o/E_l$ is at least 2; in some embodiments, at least 3; in some embodiments, at least 4; in some embodiments, at least 5; in some embodiments, at least 10; in some embodiments, at least 20; in some embodiments, at least 50; in some embodiments, at least 100; in some embodiments, at least 1000; and in some embodiments, at least 10,000. In some embodiments, the ratio of $E_o/E_l$ can be no greater than 100,000; in some embodiments, no greater than 50,000; and in some embodiments, no greater than 25,000.

In some embodiments, the overall effective tensile modulus $E_l$ can vary over the major surface of the locking sheet 110, so that the effective tensile modulus $E_l$ over a first area or portion of the locking sheet 110 may not be the same as it is over a second area or portion, but the ratio of $E_o/E_l$ at the first area is at least 2, and the ratio of $E_o/E_l$ at the second area is at least 2. That is, even if the overall stiffness of the locking sheet 110 varies over the sheet, the ratio of $E_o/E_l$ at any given location, portion or area of the locking area is still at least 2.

In some embodiments, the locking sheet 110 can be formed of a material having a first effective tensile modulus ($E_o$), and the solid regions 132 and open regions 134 can be arranged such that the apparatus 100 as a whole has an overall effective tensile modulus ($E_a$) while in the first or unlocked state, and the ratio of $E_o/E_a$ is at least 2; in some embodiments, at least 3; in some embodiments, at least 4; in some embodiments, at least 5; in some embodiments, at least 10; in some embodiments, at least 20; in some embodiments, at least 50; in some embodiments, at least 100; in some embodiments, at least 1000; and in some embodiments, at least 10,000. In some embodiments, the ratio of $E_o/E_a$ can be no greater than 100,000; in some embodiments, no greater than 50,000; and in some embodiments, no greater than 25,000.

In some embodiments, the overall effective tensile modulus $E_a$ of the apparatus 100 in the first (unlocked) state can vary across the apparatus 100, so that the overall effective tensile modulus $E_a$ over a first area or portion of the apparatus 100 may not be the same as it is over a second area or portion, but the ratio of $E_o/E_a$ at the first area is at least 2, and the ratio of $E_o/E_a$ at the second area is at least 2. That is, even if the overall stiffness of the apparatus 100 varies over the sheet, the ratio of $E_o/E_a$ at any given location, portion or area of the locking area is still at least 2.

In some embodiments, the locking sheet 110 can be formed of a material having a strain at yield ($\varepsilon_o$) (i.e., the strain at the elastic limit or at the onset of plastic deformation, as defined or determined by standard methods for a particular material in question), and the solid regions 132 and the open regions 134 can be arranged such that the locking sheet 110 formed that material can be operated beyond that strain limit and still not encounter plastic deformation. For example, in some embodiments, the material forming the solid regions 132 of the locking sheet 110 has a strain at yield ($\varepsilon_o$), the solid regions 132 and the open regions 134 are arranged such that the locking sheet 110 is configured to experience a strain ($\varepsilon_l$) without yielding of any material when the apparatus is in the first state, and wherein the strain ratio of $\varepsilon_l/\varepsilon_o$ is at least 1; in some embodiments, at least 2; in some embodiments, at least 3; in some embodiments, at least 5; in some embodiments, at least 10; in some embodiments, at least 50; in some embodiments, at least 100; in some embodiments, at least 1000; in some embodiments, at least 10,000; in some embodiments, at least 50,000; and in some embodiments, at least 100,000.

In some embodiments, at least partly due to the relative motion of the solid regions 132 within a major surface of the locking sheet 110, the apparatus 100 and/or the locking sheet 110 can exhibit three-dimensional conformability when in the first state. Conformability can be defined as the ability of the apparatus 100 to be formed over (i.e., substantially conform to) a three-dimensional object (e.g., a sphere or a more complex three-dimensional object) with little to no wrinkling (e.g., gathering) of the apparatus 100.

For example, in some embodiments, the apparatus 100 and/or the locking sheet 110 can substantially conform to a complex surface having a non-zero Gaussian curvature in the first state, such that the apparatus 100 and/or the locking sheet 110 can exhibit simultaneous curvature about two orthogonal axes, e.g., that requires a change in area in the plane of deformation. For example, a solid piece of paper cannot substantially conform to a surface having non-zero Gaussian curvature (i.e., the paper would gather and form wrinkles in doing so). However, a piece of paper that has been segmented or patterned to include solid regions and open regions in such a way that the solid regions are movable with respect to one another in a major surface of the piece of paper (e.g., a patterned or segmented piece of paper that exhibits a ratio of $E_o/E_I$ of at least 10 (e.g., in any direction)) can substantially conform to a complex surface having a non-zero Gaussian curvature.

A complex surface having a non-zero Gaussian curvature is just one example of a complex surface to which the apparatus 100 and/or the locking sheet 110 can substantially conform in the first state. It should be understood that due to the formability (i.e., combination of flexibility (bendability) and extensibility) of the apparatus 100 and/or the locking sheet 110, the apparatus 100 and/or the locking sheet 110 can substantially conform to other complex non-Gaussian surfaces as well.

In some embodiments, a stiffness ratio (as described below, or any of the below-described modulus ratios) of the first and second states can be used to define and distinguish the first "formable" state of the apparatus 100 and the second "rigid" state of the apparatus 100.

In some embodiments, the first and second states of the apparatus 100 can be characterized and/or distinguished by a stiffness ratio ($S_L/S_{UL}$). The stiffness ratio ($S_L/S_{UL}$) can be the ratio of a second (or locked) stiffness, $S_L$, (e.g., one or more of tensile modulus, bending modulus, indentation modulus, or another suitable modulus) of the apparatus 100 when the apparatus 100 is in the second state to a first (or unlocked) stiffness, $S_{UL}$, of the apparatus 100 when the apparatus 100 is in the first state.

In some embodiments, the stiffness ratio ($S_L/S_{UL}$) can be at least 2, in some embodiments, at least 3, in some embodiments, at least 4, in some embodiments, at least 5, in some embodiments, at least 8, in some embodiments, at least 10, in some embodiments, at least 15, in some embodiments, at least 20, in some embodiments, at least 40, and in some embodiments, at least 50.

As a result, in some embodiments, the apparatus 100 can be described as having a first state and a second state, as described above, where the stiffness ratio ($S_L/S_{UL}$) of the stiffness of the apparatus 100 in the second state to the stiffness of the apparatus 100 in the first state is at least 2, in some embodiments, at least 3, and so on. Said another way, the second state can be characterized as a state in which the apparatus 100 has a stiffness that is at least 2 times the stiffness of the apparatus 100 in the first state, in some embodiments, at least 3 times the stiffness of the apparatus 100 in the first state, and so on. Said yet another way, the first state can be characterized as a state in which the apparatus 100 has a stiffness that is no greater than ½ the stiffness of the apparatus 100 in the second state; in some embodiments, no greater than ⅓ the stiffness of the apparatus 100 in the second state, and so on.

In some embodiments, the first and second states of the apparatus 100 can be characterized and/or distinguished by a specific modulus ratio. For example, in some embodiments, the first state can be characterized by a first (unlocked) effective tensile modulus ($E_{UL}$), and the second state can be characterized by a second (locked) effective tensile modulus ($E_L$), and the ratio ($E_L/E_{UL}$) of the second modulus to the first modulus can be at least 2, in some embodiments, at least 3, in some embodiments, at least 4, in some embodiments, at least 5, in some embodiments, at least 8, in some embodiments, at least 10, in some embodiments, at least 15, in some embodiments, at least 20, in some embodiments, at least 40, and in some embodiments, at least 50.

The term "Effective Tensile Modulus" (ETM) refers to the slope of the line in a plot of tensile force per unit width versus strain (extension divided by length) as tested according to the procedure described later in the Examples section called Effective Tensile Modulus. This modulus is similar to Young's Modulus, but adapted to the testing of thin sheet-like materials by replacing the stress axis with force per unit width of the sheet material, where the width is measured normal to the direction of the applied tensile force. The strain is measured in the conventional sense by dividing the increased extension of the sample by its original length (i.e. ΔL/L). This Effective Tensile Modulus is useful for measuring the apparatus 100 and locking sheets 110 of the present disclosure because the cross-sectional area of those objects can be difficult to measure (particularly, the locking sheets 110 that are patterned into solid regions 132 and open regions 134).

The term "Effective Bending Modulus" (EBM) refers to the slope of the line in a plot of tensile force per unit width versus a dimensionless approximation of deflection angle when a sample is pulled on to induce bending according to the procedure described below in the Examples section called Effective Bending Modulus. This modulus is adapted to the testing of thin sheet-like materials by using force per unit width of the sheet material, where the width is measured normal to the direction of the applied bending force. The resulting bend angle is approximated by dividing the distance that the end of the sheet moves under the applied load by the length of the sheet, from the clamp to the applied load. Similar to the Effective Tensile Modules, this modulus is useful for measuring the apparatus 100 and locking sheets 110 because the cross-sectional area of those objects can be difficult to measure (particularly, the locking sheets 110 that are patterned into solid regions 132 and open regions 134). This EBM is also useful because patterned locking sheets 110 can lack the strength to support themselves across supports to be measured for bending in a more traditional procedure.

The term "Effective Indentation Modulus" (EIM) refers to the slope of the line in a plot of the applied force versus deflection distance when a sample is tested according to the procedure described below in the Examples section called Effective Indentation Modulus. The diameter of the ring used during the procedure should be specified since it will affect the readings. If the same diameter ring is used, then this is an effective procedure for comparing various sheets of material. This test measures to some extent the ability of a sheet to bend and also to extend. It therefore has a correlation with the conformability of the sheet. However, the test does not differentiate between materials that wrinkle instead of deforming their shape in a substantially continuous manner.

In some embodiments, the first state of the apparatus 100 can be characterized by the apparatus 100 having an effective tensile modulus (as defined herein) of less than 20 N/mm in some embodiments, less than 10 N/mm in some embodiments, less than 5 N/mm in some embodiments, and in some embodiments less than 1 N/mm.

As mentioned above, in some embodiments, the solid regions 132 in the locking sheet 110 can be continuous, i.e., connected to one or more adjacent solid regions 132; and in some embodiments, the solid regions 132 can be discrete or separated from adjacent solid regions 132 in a major surface of the locking sheet 110. In some embodiments, the apparatus 100 can include all continuous locking sheets 110 (i.e., employing continuous solid regions 132) or all discontinuous locking sheets 110 (i.e., employing discrete solid regions 132). In some embodiments, the apparatus 100 can include a combination of continuous and discrete solid region locking sheets 110. That is, in some embodiments, at least one locking sheet 110 in the apparatus 100 can include continuous solid regions 132, and at least one locking sheet 110 in the apparatus 100 can include discrete solid regions 132.

In some embodiments, the plurality of locking sheets 110 in the apparatus 100 can all have the same pattern, as shown in FIG. 1, can all have a different pattern, or a combination thereof. Any arrangement of patterns is possible. For example, in some embodiments, the locking sheets 110 of different patterns can be arranged in an alternating fashion (e.g., A, B, A, B, etc.), can be arranged in a block pattern (e.g., A, A, B, B, etc.), or a combination thereof (e.g., A, A, B, B, A, A, etc.). Still, in some embodiments, locking sheets 110 of different patterns can be arranged (i.e., stacked) randomly.

In some embodiments employing at least two locking sheets 110 of the same pattern, two identically-patterned locking sheets 110 can be arranged to substantially align with one another, such that the solid regions 132 in one locking sheet 110 substantially overlap and align with the solid regions 132 in an adjacent (i.e., above or below) locking sheet 110, as shown in FIG. 1.

However, in some embodiments, as shown in FIG. 4, two identically-patterned locking sheets 110 can be staggered with respect to one another, such that solid regions 132 in a first locking sheet 110 overlap open regions 134' in a second locking sheet 110', and open regions 134 in the first locking sheet 110 overlap solid regions 132' in the second locking sheet 110'. In FIG. 4, the top, first locking sheet 110 is shown in white, and the bottom, second locking sheet 110' has solid regions 132' shown in light gray and open regions 134' shown in darker gray. More specifically, in some embodiments employing continuous solid regions 132, as shown in FIGS. 1 and 4, the solid regions 132 can include islands and one or more connections, or bridges, positioned to connect each island to an adjacent island.

As shown in FIG. 4, the first locking sheet 110 includes islands 136 having an octagonal shape, and each island 136 is connected to one or more adjacent islands 136 by one or more bridges 138, respectively. The islands 136 are arranged in a square-packed arrangement, such that the pattern of the locking sheet 110 includes a repeat unit, or unit cell, comprising one central octagonal island 136 that is connected to four adjacent islands 136 by four bridges 138, respectively, that are equally-spaced about the island 136, such that every other octagonal edge of each island 136 is connected to a bridge 138. By way of example, each bridge 138 includes a 90-degree bend, and each bridge 138 coming from the same island 136 bends in the same direction (i.e., clockwise or counter-clockwise), such that the open regions 134 include a substantially square space between four adjacent islands 136 that includes two bridges 138, and such that the pattern of the first locking sheet 110 includes 4-fold rotational symmetry about the center of each island 136.

Furthermore, due to the dense packing of the islands 136, the pattern includes staggered horizontal rows of islands 136, staggered vertical rows of islands 136, and diagonal rows of islands 136. Each island 136 has bridges 138 bending in the same direction (i.e., clockwise or counter-clockwise) as that of any island 136 in the same horizontal row, but in the opposite direction as that of any island 136 in an adjacent horizontal row. Similarly, each island 136 has bridges 138 bending in the same direction (i.e., clockwise or counter-clockwise) as that of any island 136 in the same vertical row, but in the opposite direction as that of any island 136 in an adjacent vertical row. However, each island 136 has bridges 138 bending in the opposite direction as that of an adjacent island 136 in the same diagonal row (in any direction).

The second locking sheet 110' the same pattern as the first locking sheet 110, i.e., also includes islands 136' and bridges, but the bridges in the second locking sheet 110' are not visible in FIG. 4, because the islands 136 in the first locking sheet 110 are positioned to overlap the bridges of the second locking sheet 110'. In addition, each island 136 in the first locking sheet 110 also partially overlaps four islands 136' in the second locking sheet 110'.

The specific pattern of the locking sheets 110, 110' of FIG. 4 is shown by way of example only, and particularly, to illustrate how adjacent locking sheets 110 (e.g., employing the same pattern) in the apparatus 100 can be staggered so that solid regions 132 in one locking sheet 110 can overlap open regions 134' in an adjacent locking sheet 110.

Examples of discontinuous locking sheets (i.e., employing discrete solid regions) are illustrated in FIGS. 7-10D and described below. Additional examples of continuous locking sheets (i.e., employing continuous solid regions) are illustrated in FIGS. 11-25 and described below.

In addition, or alternatively, in some embodiments, adjacent locking sheets 110 in the apparatus 100 (e.g., whether having the same or different patterns) can be rotated with respect to one another about a z-axis that is substantially orthogonal with respect to, or normal to, each locking sheet 110. That is, in some embodiments, even if the locking sheets 110 include the same pattern, one or more locking sheets 110 can be rotated with respect to one another, such that the patterns do not directly and identically overlap one another. For example, in some embodiments, a first locking sheet 110 can be rotated about the z-axis at an angle of 90 degrees with respect to a second locking sheet 110. In some embodiments, e.g., if more than two locking sheets 110 are employed, the locking sheets 110 can be arranged such that the pattern rotation alternates with each sheet, such that a first and a third sheet may exactly overlap (i.e., are not rotated with respect to one another), while a second and a fourth sheet exactly overlap one another, but are rotated at an angle with respect to the first and the third sheets. In other embodiments, each locking sheet 110 can be rotated at an angle with respect to each adjacent locking sheet 110. For example, a second locking sheet 110 can be rotated at an angle of 90 degrees with respect to a first locking sheet 110, a third locking sheet 110 can be rotated an angle of 90 degrees with respect to the second locking sheet 110, and so on.

In some embodiments, one locking sheet 110 can include more than one pattern of solid regions 132 and open regions 134. That is, in some embodiments, the pattern within a given locking sheet 110 need not be constant. For example, the pattern near the periphery of a locking sheet 110 can be different from the pattern near the center of the locking sheet 110, or the pattern can change, or even be random, throughout a given locking sheet 110.

In some embodiments, one or more locking sheets 110 can be fixed (e.g., pinned or glued) to the envelope 102 and/or one or more other locking sheets 110 in one or more points or locations. In such embodiments, the locking sheet(s) 110 can be coupled to the envelope 102 and/or other locking sheet(s) 110 by any of the coupling means described below with respect to coupling discrete solid regions 532 of FIG. 7 to an envelope 502.

That is, in some embodiments, at least one locking sheet 110 in the apparatus 100 can include a varying pattern of solid regions 132 and open regions 134. Such variations in a pattern can themselves follow a pattern, can be a block pattern (e.g., one pattern on one half of the locking sheet 110 and a different pattern on the other half), can be random, or a combination thereof.

In some embodiments, the locking sheets 110, or a portion thereof (e.g., a surface 125, 125' (see FIGS. 4 and 5) oriented to face another locking sheet 110), can include a high friction surface, which can be achieved by the material composition and/or texture of the respective surface or by treating the surface (e.g., with a coating, by coupling a high-friction layer to a desired portion of the locking sheet 110, etc.). Such high friction surfaces can facilitate jamming together of the locking sheets 110 as the apparatus 100 is changed to the second state. As a result, such high friction surfaces can enhance the stiffness (e.g., any of the above-described types of stiffness) of the apparatus 100 in the second state.

In some embodiments, high friction surfaces can be an inherent result of a manufacturing process. For example, paper can itself have a sufficiently high friction surface for two locking sheets 110 made of paper to inter-engage under vacuum. In other embodiments, high friction surfaces can be formed by one or more of embossing, knurling, any suitable microreplication process, abrading, sand-blasting, molding, stamping, vapor deposition, other suitable means of forming a high friction surface, or combinations thereof.

Figure 5:
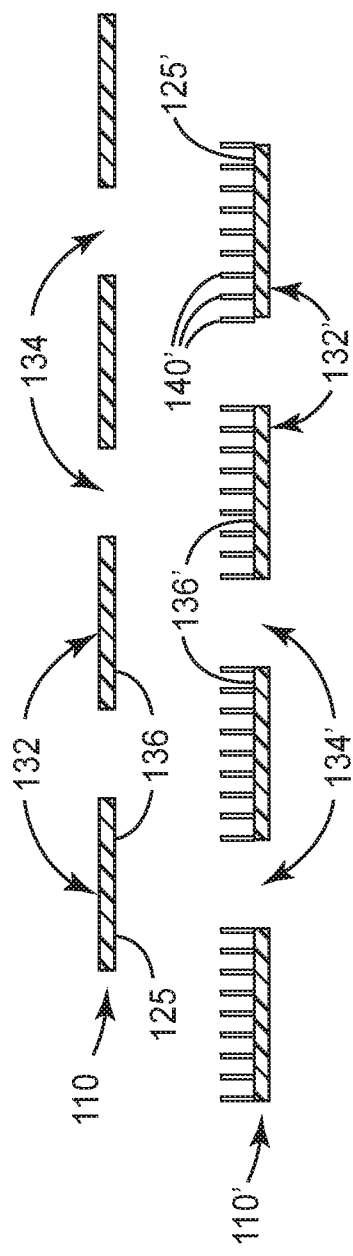
FIG. 5 is a side cross-sectional view of the two locking sheets of FIG. 4, with the lower locking sheet shown as including a high friction surface.

FIG. 5 shows a side cross-sectional view of a portion of the two staggered, overlapping locking sheets 110, 110' of FIG. 4. In FIG. 5, the foreground solid regions 132, 132' that include islands 136, 136' and foreground open regions 134, 134' are shown, but the bridges 138 and background islands 136, 136' are removed from each locking sheet 110, 110' for clarity.

As shown in FIG. 5, each locking sheet 110, 110' includes a surface 125, 125' configured to face the other locking sheet 110', 110. However, the surface 125' of the second locking sheet 110' is shown as including a high friction surface, and particularly, a high friction surface 125' that is structured to include engagement features 140' that extend in the Z direction toward the first locking sheet 110 (or have a Z dimension in the direction of the first locking sheet 110). By way of example only, the engagement features 140' are shown as being equally-spaced posts. One example of a suitable structured high friction surface that can be employed on locking sheets of the present disclosure is a textured or structured material available under the trade designation, "3M™ Gripping Material" from 3M Company, St. Paul, Minn.

The entire surface 125' need not include the high friction surface features, but rather, in some embodiments, only a portion of the surface 125' is a high friction surface. In the embodiment shown in FIG. 5, each island 136' of the second locking sheet 110 is shown by way of example only as including posts or pegs. In some embodiments, these posts can be distributed over the entire area of each island 136', and in some embodiments, the posts can be distributed over a portion of the area of some or all of the islands 136'.

The posts are illustrated by way of example only as being tall, thin, pin-like, cylindrical posts; however, it should be understood that a variety of structure shapes can be employed in structured high friction surfaces of the present disclosure, including, but not limited to, posts of other cross-sectional shapes (e.g., square, triangular, polygonal, etc.), square pyramids, triangular pyramids, other suitable shapes, or combinations thereof.

Although not shown in FIG. 5, in some embodiments, the first locking sheet 110 can include openings or recesses that are dimensioned to receive (i.e., inter-engage with) the engagement features 140' of the second locking sheet 110'. Alternatively, or additionally, the surface 125 of the first locking sheet 110 can also include engagement features that extend in the Z direction toward the second locking sheet 110' and that can inter-engage, or interlock, with the structures 140' of the second locking sheet 110'. In such embodiments, the engagement features on the first locking sheet 110 need not be the same as those on the second locking sheet 110', as long as the engagement features can still inter-engage with the structures 140'. Because the first and second locking sheets 110, 110' can each include one or more posts or extensions, one or more recesses or openings, or a combination thereof, the first locking sheet 110 can generally be described as having a surface 125 including a plurality of first engagement features, and the second locking sheet 110' can be described as having a plurality of second engagement features that are configured to engage the plurality of first engagement features.

It should be understood that the staggered configuration of FIG. 5 is shown by way of example only, and that high friction surfaces (e.g., including inter-engaging engagement features) can be employed in non-staggered (e.g., aligned) locking sheets as well.

In some embodiments, particularly, in staggered configurations, the open regions 134 in the first locking sheet 110 can be dimensioned to inter-engage with the engagement features 140' of the second locking sheet 110', such that the open regions 134 of the first locking sheet 110 can function as the plurality of first engagement features. In other embodiments, locking sheets 110, 110' can be patterned such that the solid regions 132, 132' in the first and second locking sheets 110, 110' can tilt or rotate even slightly out of the major surface of their respective locking sheet 110 as the solid regions 132 move relative to one another in the major surface of the respective locking sheet 110, i.e., when the apparatus 100 is formed into a desired shape. In such embodiments, the tilted or rotated solid regions 132, 132' in the first or second locking sheet 110 or 110' can inter-engage with the solid regions 132', 132 and/or the open regions 134', 134 in the other locking sheet 110' or 110, respectively.

While structures on adjacent locking sheets 110 can be described as inter-engaging, it should be understood that such inter-engaging structures are generally reversibly inter-engaged, so that the apparatus 100 can be changed from the first state to the second state, and returned to the first state again, as desired. This can provide for the formability of the apparatus 100 not being lost after the first time the apparatus 100 is changed to the second state.

FIGS. 6A-10D illustrate various shape-formable apparatuses of the present disclosure, wherein like numerals represent like elements. The shape-formable apparatuses of FIGS. 6A-10D share many of the same elements, features, and functions as the apparatus 100 described above with respect to FIGS. 1, 4 and 5. Reference is made to the description above accompanying FIGS. 1-5 for a more complete description of the features and elements (and alternatives to such features and elements) of the embodiments illustrated in FIGS. 6A-10D. Any of the features described above with respect to FIGS. 1, 4 and/or 5 can be applied to any of the embodiments of FIGS. 6A-10D, and vice versa.

Figure 6A:
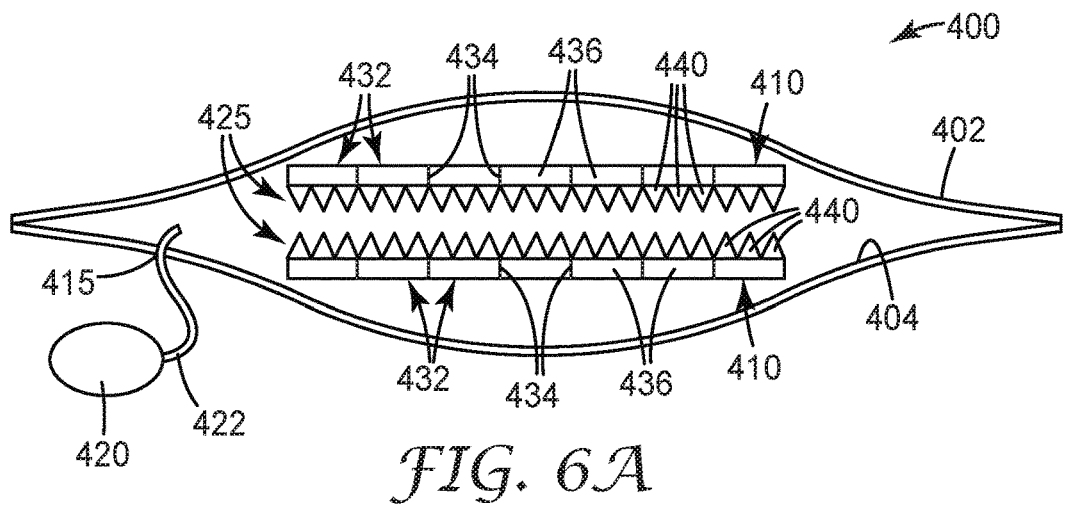
FIGS. 6A-6C are schematic cross-sectional views of a shape-formable apparatus according to another embodiment of the present disclosure, employing locking sheets comprising continuous solid regions and high friction surfaces, illustrating a method according to one embodiment of the present disclosure of using the shape-formable apparatus.
Figure 6B:
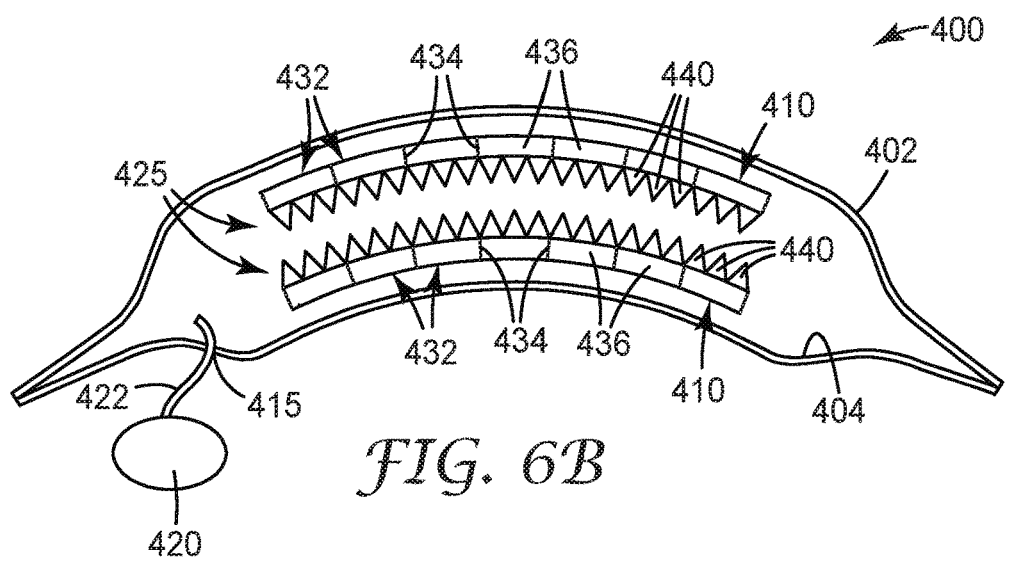
Figure 6C:
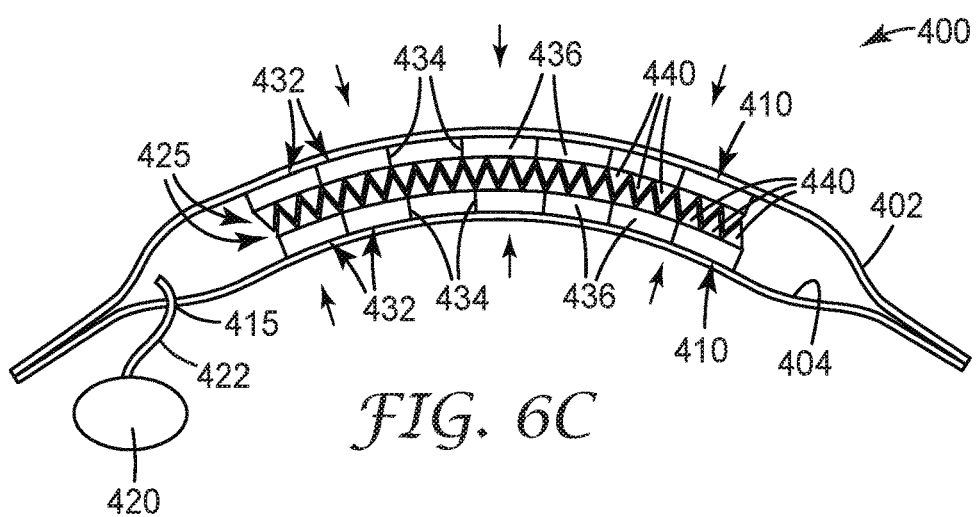

FIGS. 6A-6C illustrate a shape-formable apparatus 400 according to another embodiment of the present disclosure, employing continuous locking sheets 410 comprising continuous solid regions 432, open regions 434, and surfaces 425 configured to face an adjacent locking sheet 410. The apparatus 400 is generally sheet-like or plate-like, or has a sheet-like or plate-like configuration, as opposed to a three-dimensionally bulky configuration. FIGS. 6A-6C also illustrate a method according to one embodiment of the present disclosure of using the shape-formable apparatus 400.

The apparatus 400 includes an envelope 402 that defines a chamber 404, locking sheets 410, a port 415, a connector 422, and a vacuum source 420 that are each shown schematically merely for purposes of illustration. While the solid regions 432 and the open regions 434 of the locking sheets 410 are shown schematically for illustration purposes, it should be understood that the locking sheets 410 are patterned just like any other locking sheet of the present disclosure and are intended to represent continuous locking sheets of the present disclosure (i.e., employing continuous solid regions 432, such as any of those described above or below). As shown, the solid regions 432 can include islands 436. As with any other continuous locking sheet patterns of the present disclosure, the islands 436 can be connected to adjacent islands by bridges that extend through the open regions 434; however, for simplicity, the bridges are not shown in FIGS. 6A-6C. Furthermore, seven islands 436 are illustrated by way of example only merely for illustration purposes.

The surface 425 of each locking sheet 410 includes a high friction surface, and particularly, includes a plurality of engagement features 440. The top locking sheet 410 can be referred to as a first locking sheet 410 having a plurality of first engagement features 440, and the bottom locking sheet 410 can be referred to as a second locking sheet 410 having a plurality of second engagement features 440 configured to engage the plurality of first engagement features 440. The surfaces 425 are shown by way of example as including the high friction surface, i.e., the engagement features 440, across the entire surface 425; however, as described above, this need not be the case. The engagement features 440 are shown schematically as having triangular cross-sectional shapes, such that engagement features 440 in one locking sheet 410 can inter-engage with engagement features 440 in the other locking sheet 410. Specifically, the engagement features 440 schematically represent engagement features 440 that protrude in the Z direction toward an adjacent locking sheet 410, such that when the locking sheets 410 are brought into contact, the engagement features 440 from one locking sheet 410 will be moved into the openings or spaces between adjacent engagement features 440 in the other locking sheet 410.

While two locking sheets 410 are shown in FIGS. 6A-6C for simplicity, it should be understood that as many locking sheets 410 as structurally possible or necessary can be employed in the apparatus 400. In embodiments employing more than two locking sheets 410, two or more locking sheets 410 can each include one or more high friction surfaces (e.g., with engagement features 440) on a surface 425 that is oriented to face another locking sheet 410. In some embodiments, each locking sheet 410 (or at least intermediate locking sheets 410 that are positioned between two adjacent locking sheets 410) can include two surfaces 425 that are each oriented to face an adjacent locking sheet 410, and each surface 425 (e.g., a top surface and a bottom surface) can include one or more high friction surfaces (e.g., with engagement features 440).

The apparatus 400 is shown in FIG. 6A in a first state. In the first state, the pressure within the chamber 404 can be substantially the same as the pressure outside the chamber 404, i.e., ambient pressure. As shown in FIG. 6B, in the first state, the apparatus 400 can be formed into any desired shape, and the locking sheets 410 (e.g., the solid regions 432) can be slidable relative to one another and/or movable toward and away from one another (i.e., in a Z direction that is orthogonal with respect to, or normal to, the locking sheets 410). As also shown in FIG. 6B, the locking sheets 410, in addition to the envelope 402, are extensible and formable, due to relative motion between adjacent locking sheets 410, as well as relative motion between solid regions 432 that can occur within the major surface of each locking sheet 410.

After the desired shape has been achieved, the vacuum source 420 can be activated to evacuate the chamber 404, thereby reducing the pressure in the chamber 404 to below ambient pressure. As the chamber 404 is evacuated, the locking sheets 410 are forced into contact with one another, and the desired shape of the apparatus 400 is essentially locked. As shown in FIG. 6C, in embodiments in which the locking sheets 410 include high friction surfaces, and particularly, engagement features 440, the engagement features 440 of one locking sheet 410 can inter-engage with the engagement features 440 on the other locking sheet 410, as described above. Such inter-engagement between adjacent locking sheets 410 can enhance the stiffness or rigidity of the apparatus 400 in the second state.

As mentioned above, the apparatus 400 can be maintained in the second state, as shown in FIG. 6C, for as long as desired by either maintaining the vacuum pressure via the vacuum source 420, or by sealing the port 415 or the connector 422 after the pressure in the chamber 404 has been reduced.

A method according to one embodiment of the present disclosure will now be described with respect to the apparatus 400 of FIGS. 6A-6C. Such a method can include providing the apparatus 400 in a first state, as shown in FIG. 6A, in which the apparatus 400 is formable and the locking sheets 410 are slidable relative to one another, and the solid regions 432 of each locking sheet 410, including the islands 436, are movable within the major surface of the locking sheet 410 relative to one another. In addition, in the first state, any high friction surfaces on surfaces 425 (e.g., including engagement features 440) of the locking sheets 410 that are oriented to face another locking sheet 410 may move past another high friction surface (e.g., including engagement features 440) on an adjacent locking sheet 410 without inter-engaging or only intermittently engaging.

The method can further include forming the apparatus 400 into a desired shape (i.e., a three-dimensional shape), as shown in FIG. 6B, wherein the formability of the apparatus 400 is at least partly facilitated by the relative motion of the solid regions 432 (e.g., the islands 436) in the locking sheets 410.

As shown in FIG. 6C, the method can further include changing the apparatus 400 from the first, unlocked, state to the second, locked, state by evacuating the chamber 404, for example, by activating the vacuum source 420 to remove gas (e.g., substantially all gas) from the chamber 404 via the port 415 and, optionally, the connector 422. Evacuating the chamber 404 causes the locking sheets 410 to be drawn into direct and intimate contact with one another, thereby increasing the overall stiffness or rigidity of the apparatus 400 to essentially lock the apparatus 400 in the desired shape. The direct and intimate contact of the locking sheets 410 can also include inter-engagement of engagement features 440 on adjacent locking sheets 410, such that the engagement features 440 of adjacent locking sheets 410 are locked with respect to one another. As mentioned above, however, such locking can be reversible, such that the apparatus 400 can be changed from the second state back to the formable first state by releasing the vacuum from the chamber 404 (i.e., allowing the chamber 404 to return to ambient pressure).

Figure 7:
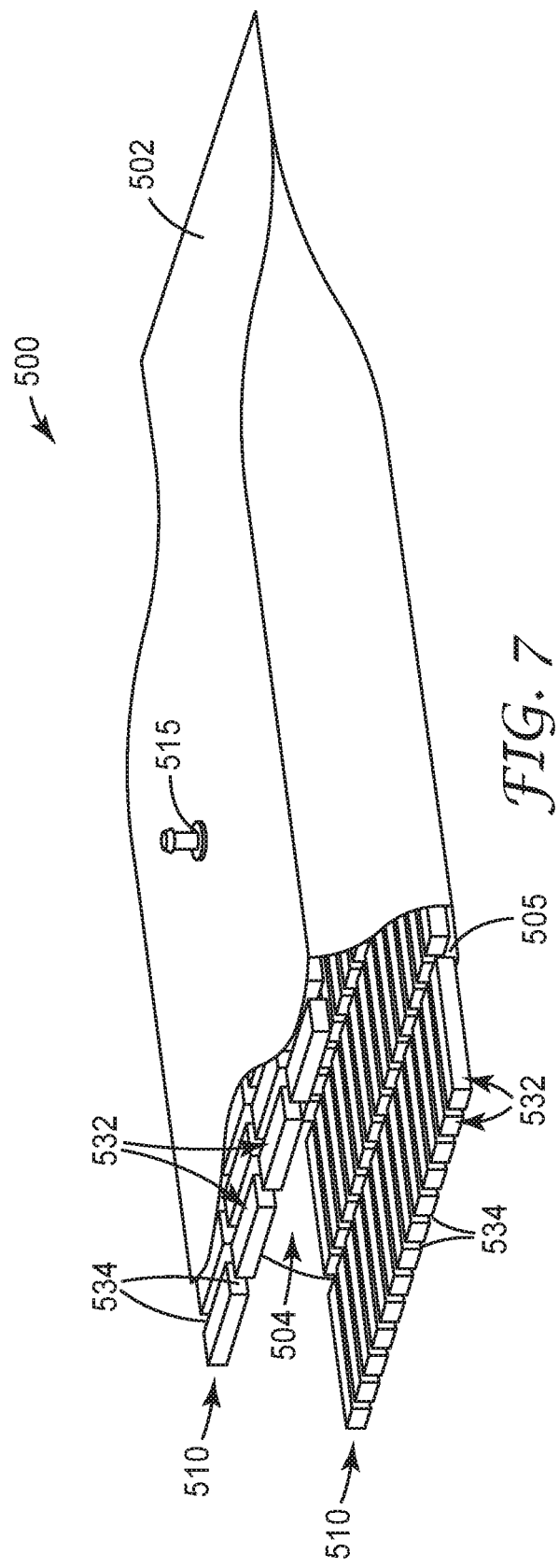
FIG. 7 is a cutaway perspective view of a shape-formable apparatus according to another embodiment of the present disclosure, employing locking sheets comprising discrete solid regions.

FIG. 7 illustrates a shape-formable apparatus 500 according to another embodiment of the present disclosure. The apparatus 500 is generally sheet-like or plate-like, or has a sheet-like or plate-like configuration. The shape-formable apparatus 500 includes an envelope 502 that defines a chamber 504; a plurality of locking sheets 510 comprising solid regions 532 and open regions 534; and a port (or opening) 515 positioned to fluidly couple the chamber 504 with ambience, such that a vacuum source (not shown) can be coupled to the port 515 for evacuating the chamber 504. The difference between the apparatus 500 of FIG. 7 and the apparatus 100 of FIG. 1 is that the apparatus 500 includes discontinuous locking sheets 510, i.e., including discrete or separate solid regions 532.

As shown in FIG. 7, in some embodiments, the discrete solid regions 532 can form "floating" islands that are not connected to one another, and can be referred to interchangeably as discrete solid regions or floating islands. In such embodiments, the islands can be coupled to a substrate (or backing) and particularly, an extensible substrate, so that the locking sheets 510 have significant conformability. In some embodiments, at least a portion of the envelope 502 (e.g., a top or bottom portion or layer thereof) can provide at least a portion of the substrate for a locking sheet 510. Alternatively, or additionally, the apparatus 500 can include an additional material or layer that forms at least a portion of the substrate for a locking sheet 510, and such additional material or layer can be sheet-like or plate-like, and can be positioned in the chamber 504. Such additional substrate materials or layers can be formed of any of the variety of materials described above with respect to the envelope 102 of FIG. 1. In this case, however, the gas permeability of the substrate can be high, since it may not comprise the gas impermeable envelope 502 of the apparatus. In addition, in some embodiments, a continuous locking sheet of the present disclosure can serve as the substrate to which a discontinuous locking sheet is coupled.

Similar to FIG. 1, FIG. 7 is illustrated for clarity purposes with the top and bottom sides of the envelope 502 being substantially spaced apart (i.e., with a sidewall joining them), and with the locking sheets 510 being substantially spaced apart from one another. However, it should be understood that this illustration is used merely to better and more clearly show how the locking sheets 510 can overlap one another and can be positioned in the chamber 504. In reality, the apparatus 500 can appear much flatter, having a sheet-like or plate-like configuration.

The apparatus 500 of FIG. 7 is shown by way of example only as including two locking sheets 510, each of which includes discrete solid regions 532 that are directly coupled to the envelope 502, i.e., an inner surface 505 thereof. Particularly, as shown, the solid regions 532 of the locking sheets 510 can be coupled to a top inner surface of the envelope 502 to form one locking sheet 510 and a bottom inner surface of the envelop 502 to form the other locking sheet 510, such that the resulting locking sheets 510 can have an at least partially overlapping and substantially parallel configuration. In some embodiments, the top inner surface and the bottom inner surface of the envelope 502 can be provided by sheets or sheet-like layers that can be sealed on all sides to provide the sheet-like apparatus 500; however other means of forming the sheet-like apparatus 500 are possible.

The solid regions 532 can be coupled to the envelope 502 (and/or substrate, if employed) by a variety of coupling means, including, but not limited to, hook-and-loop fasteners (e.g., irreversible engagement features, such as those employed in interlocking materials available under the trade designation 3M™ DUAL LOCK™, 3M Company, St. Paul, Minn.), adhesives, cohesives, clamps, crimps, heat sealing, stitches, pins, staples, screws, nails, rivets, brads, welding (e.g., sonic (e.g., ultrasonic) welding), any thermal bonding technique (e.g., heat and/or pressure applied to one or both of the components to be coupled), other suitable coupling means, or combinations thereof.

By way of further example, the top locking sheet 510 shown in FIG. 7 includes a plurality of rectangular-shaped islands 532 arranged in horizontal and vertical rows, with the long side of each rectangular island 532 oriented in an X direction, and the bottom locking sheet 510 includes the same rectangular islands 532 arranged in horizontal and vertical rows, but rotated 90 degrees with respect to the islands 532 of the top locking sheet 510, such that the long side of the rectangular islands 532 of the bottom locking sheet 510 have the long side oriented in a Y direction, or a direction that is oriented substantially perpendicularly with respect to the long-side direction (X direction) of the top locking sheet 510. That is, the apparatus 500 of FIG. 7 illustrates one example of adjacent locking sheets 510 (and particularly, discontinuous locking sheets 510) having patterns that are rotated with respect to one another. In embodiments in which one or both of the top and bottom locking sheets 510 include high friction surfaces, the rotated patterns can ensure, for example, that one island 532 of the bottom locking sheet 510 will overlap and inter-engage with more than one island 532 of the top locking sheet 510 when the apparatus 500 is in the second state, creating one rigid sheet having a thickness equal to the sum of the thicknesses of the individual locking sheets 510.

The regularly-arranged and rectangular-box-shaped islands 532 in each locking sheet 510 (i.e., in rows of uniformly-spaced islands) are shown by way of example only. However, it should be understood that not only are other shapes of islands 532 possible, but other arrangements are possible as well. For example, in some embodiments, the islands 532 can be disc-shaped, or have another useful shape. Additionally, or alternatively, the islands 532 can be arranged in a different pattern (e.g., a more densely packed pattern), or in a random arrangement, as long as each island 532 overlaps at least a portion of an island 532 in an adjacent locking sheet 510. In addition, each locking sheet 510 need not include the same sized and shaped islands 532 as in the adjacent locking sheet 510, or have the same or a similar pattern or arrangement. Rather, in some embodiments, two adjacent locking sheets 510 can have differently shaped, sized and/or arranged islands 532.

In some embodiments, as shown in FIG. 7, each locking sheet 510 can be coupled to the envelope 502, or in other embodiments, each locking sheet 510 can be coupled to an additional substrate. Still, in other embodiments, the apparatus 500 can include a combination of discontinuous locking sheets 510 that are coupled to the envelope 502 and discontinuous locking sheets 510 that are coupled to an additional substrate (e.g., that are located, e.g., stacked, in the space between the two locking sheets 510 shown in FIG. 7).

Furthermore, as mentioned above, in some embodiments, the apparatus 500 can include a combination of discontinuous locking sheets 510 and continuous locking sheets. For example, one or more continuous locking sheets can be positioned in the chamber 504 in the space between the two illustrated discontinuous locking sheets 510, i.e., in an at least partially overlapping relationship and substantially parallel configuration with one or both of the discontinuous locking sheets 510. In such embodiments, the one or more continuous locking sheets can include two surfaces (i.e., a top surface and a bottom surface) that are each configured to face an adjacent locking sheet 510. One or both of these surfaces can include a high friction surface that is configured to inter-engage with one of the discontinuous locking sheets 510. That is, high friction surfaces can be employed in any embodiment of the present disclosure on any surface of a locking sheet that is oriented to face another locking sheet.

Figure 8A:
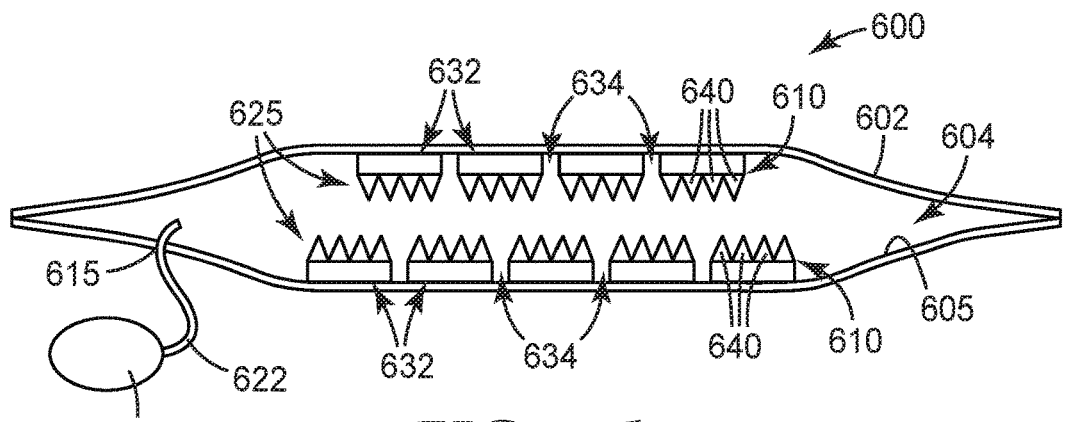
FIGS. 8A-8C are schematic cross-sectional views of a shape-formable apparatus according to another embodiment of the present disclosure, employing locking sheets comprising discrete solid regions and high friction surfaces, illustrating a method according to one embodiment of the present disclosure of using the shape-formable apparatus.
Figure 8B:
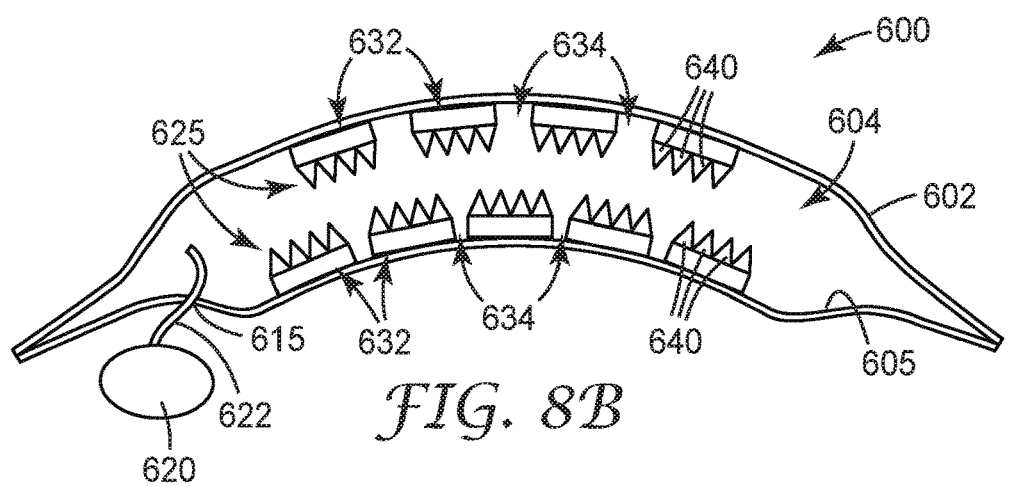
Figure 8C:
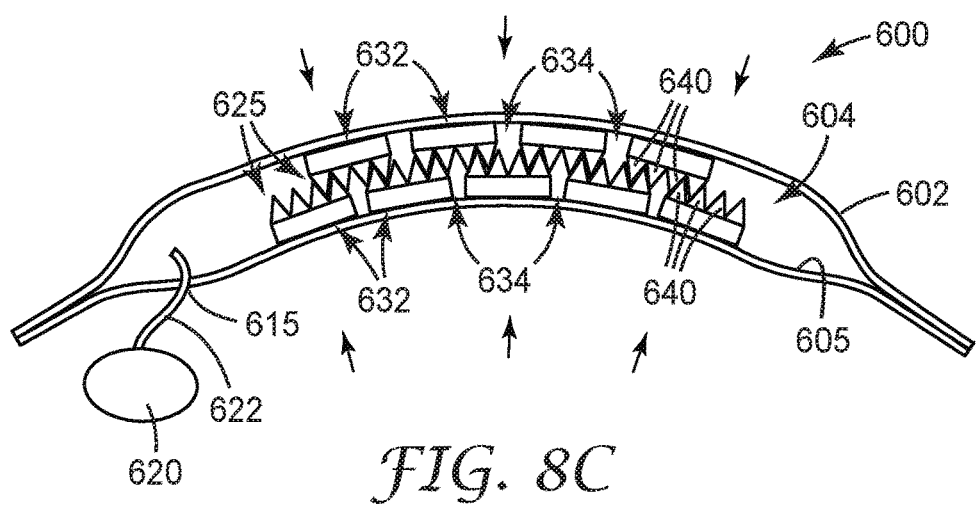

FIGS. 8A-8C illustrate a shape-formable apparatus 600 according to another embodiment of the present disclosure, employing discontinuous locking sheets 610 comprising discrete solid regions 632, open regions 634, and surfaces 625 configured to face an adjacent locking sheet 610. The apparatus 600 is generally sheet-like or plate-like, or has a sheet-like or plate-like configuration. FIGS. 8A-8C also illustrate a method according to one embodiment of the present disclosure of using the shape-formable apparatus 600.

The apparatus 600 includes an envelope 602 that defines a chamber 604, locking sheets 610, a port 615, a connector 622, and a vacuum source 620 that are each shown schematically merely for purposes of illustration. For simplicity, only two locking sheets 610 are shown, the top locking sheet 610 including four discrete solid regions, or "islands," 632, and the bottom locking sheet 610 including five islands that are staggered with respect to the islands 632 in the top locking sheets 610, such that when the top and bottom locking sheets 610 are brought into direct and intimate contact, the two locking sheets 610 inter-engage to essentially form one rigid sheet.

By way of example, each locking sheet 610 is illustrated as being directly coupled to the envelope 602, and particularly, an inner surface 605 thereof. Specifically, the top locking sheet 610 is illustrated as being coupled to an upper portion or upper inner surface of the envelope 602, and the bottom locking sheet 610 is illustrated as being coupled to a bottom portion or lower inner surface of the envelope 602.

The surface 625 of each locking sheet 610 includes a high friction surface, and particularly, includes a plurality of engagement features 640. The discrete islands 632 of each locking sheet 610 can collectively define the surface 625, and at least a portion of the surface 625 (e.g., at least a portion of at least some of the islands 632) of each locking sheet 610 can include the high friction surface. Specifically, each surface 625 of the locking sheets 610 includes engagement features 640.

The top locking sheet 610 can be referred to as a first locking sheet 610 having a plurality of first engagement features 640, and the bottom locking sheet 610 can be referred to as a second locking sheet 610 having a plurality of second engagement features 640 configured to engage the plurality of first engagement features 640. The surfaces 625 are shown by way of example as including the high friction surface, i.e., the engagement features 640, across the entire surface 625; however, as described above, this need not be the case. The engagement features 640 are shown schematically as having triangular cross-sectional shapes, such that engagement features 640 in one locking sheet 610 can inter-engage with engagement features 640 in the other locking sheet 610. Specifically, the engagement features 640 schematically represent engagement features 640 that protrude in the Z direction toward an adjacent locking sheet 610, such that when the locking sheets 610 are brought into contact, the engagement features 640 from one locking sheet 610 will be moved into the openings or spaces between adjacent engagement features 640 in the other locking sheet 610.

While two locking sheets 610 are shown in FIGS. 8A-8C for simplicity, it should be understood that as many locking sheets 610 as structurally possible or necessary can be employed in the apparatus 600. In embodiments employing more than two locking sheets 610, for example, one or more continuous locking sheets can be positioned between the two illustrated discontinuous locking sheets 610. In addition, or alternatively, one or more discontinuous locking sheets having islands coupled to an additional substrate can be positioned between the two illustrated discontinuous locking sheets 610.

In addition, in some embodiments employing more than the two illustrated locking sheets 610, the locking sheets 610 can each include one or more high friction surfaces (e.g., with engagement features 640) on a surface 625 that is oriented to face another locking sheet 610. In some embodiments, each locking sheet 610 (or at least intermediate locking sheets 610 that are positioned between two adjacent locking sheets 610) can include two surfaces 625 that are each oriented to face an adjacent locking sheet 610, and each surface 625 (e.g., a top surface and a bottom surface) can include one or more high friction surfaces (e.g., with engagement features 640).

The apparatus 600 is shown in FIG. 8A in a first state. In the first state, the pressure within the chamber 604 can be the same as the pressure outside the chamber 604, i.e., ambient pressure. As shown in FIG. 8B, in the first state, the apparatus 600 can be formed into any desired shape, and the locking sheets 610 (e.g., the solid regions 632) can be slidable relative to one another and/or movable toward and away from one another (i.e., in a Z direction that is orthogonal with respect to, or normal to, the locking sheets 610) by virtue of the extensibility and conformability of the envelope 602. As also shown in FIG. 8B, the locking sheets 610 are extensible and formable, due to the envelope material properties, as well as the relative motion between solid regions 632 that can occur within a major surface of each locking sheet 610.

After the desired shape has been achieved, the vacuum source 620 can be activated to evacuate the chamber 604, thereby reducing the pressure in the chamber 604 to below ambient pressure. As the chamber 604 is evacuated, the locking sheets 610 are forced into contact with one another, and the desired shape of the apparatus 600 is essentially locked. As shown in FIG. 8C, in embodiments in which the locking sheets 610 include high friction surfaces, and particularly, engagement features 640, the engagement features 640 of one locking sheet 610 can inter-engage with the engagement features 640 on the other locking sheet 610, as described above. Such inter-engagement between adjacent locking sheets 610 can enhance the stiffness or rigidity of the apparatus 600 in the second state.

In addition, as mentioned above, the islands 632 of the top locking sheet 610 are staggered with respect to the islands 632 of the bottom locking sheet 610, such that one island 632 of the top locking sheet 610 can engage (e.g., inter-engage via mating engagement features 640) two islands 632 of the bottom locking sheet 610, thereby forming one rigid sheet, and enhancing the resulting stiffness of the apparatus 600 in the second state.

As mentioned above, the apparatus 600 can be maintained in the second state, as shown in FIG. 8C, for as long as desired by either maintaining the vacuum pressure via the vacuum source 620, or by sealing the port 615 or the connector 622 after the pressure in the chamber 604 has been reduced.

A method according to one embodiment of the present disclosure will now be described with respect to the apparatus 600 of FIGS. 8A-8C. Such a method can include providing the apparatus 600 in a first state, as shown in FIG. 8A, in which the apparatus 600 is formable and the locking sheets 610 are slidable relative to one another, and the solid regions, or islands, 632 of each locking sheet 610 are movable relative to one another (i.e., within a major surface of the respective locking sheet 610). In addition, in the first state, any high friction surfaces on surfaces 625 of the locking sheets 610 that are oriented to face another locking sheet 610 may move past another high friction surface on an adjacent locking sheet 610 without inter-engaging or only intermittently engaging.

The method can further include forming the apparatus 600 into a desired shape (i.e., a three-dimensional shape), as shown in FIG. 8B, where the formability of the apparatus 600 is at least partly facilitated by the relative motion of the islands 632 in the locking sheets 610 and the material makeup of the envelope 602 (or any substrate to which islands are coupled, if not coupled directly to the envelope 602).

As shown in FIG. 8C, the method can further include changing the apparatus 600 from the first, unlocked, state to the second, locked, state by evacuating the chamber 604, for example, by activating the vacuum source 620 to remove gas (e.g., substantially all gas) from the chamber 604 via the port 615 and, optionally, the connector 622. Evacuating the chamber 604 causes the locking sheets 610 to be drawn into direct and intimate contact with one another, thereby increasing the overall stiffness or rigidity of the apparatus 600 to essentially lock the apparatus 600 in the desired shape. The direct and intimate contact of the locking sheets 610 can also include inter-engagement of engagement features 640 on adjacent locking sheets 610, such that the engagement features 640 of adjacent locking sheets 640 are locked with respect to one another. As mentioned above, however, such locking can be reversible, such that the apparatus 600 can be changed from the second state back to the formable first state by releasing the vacuum from the chamber 604 (i.e., allowing the chamber 604 to return to ambient pressure).

FIGS. 9A and 9B illustrate close-up partial views of an apparatus 700 according to another embodiment of the present disclosure. The apparatus 700 is generally sheet-like or plate-like and includes two discontinuous locking sheets 710.

The apparatus 700 includes an envelope 702 that defines a chamber 704; a plurality of locking sheets 710 comprising discrete solid regions (or "islands") 732 and open regions 734; and a port (or opening) 715 positioned to fluidly couple the chamber 704 with ambience, such that a vacuum source (not shown) can be coupled to the port 715 for evacuating the chamber 704.

The apparatus 700 includes many of the same elements, features and functions as the embodiments of FIGS. 7 and 8A-8C, which also employ discontinuous locking sheets. Reference is made to the description above accompanying FIGS. 7 and 8A-8C for a more complete description of the features (and alternatives to such elements and features) of the embodiments of FIGS. 9A and 9B.

The difference between the apparatus 700 of FIGS. 9A and 9B and the apparatus 500 of FIG. 7 is that the discontinuous locking sheets 710 of FIGS. 9A and 9B include discrete islands 732 that each have a fixed end 742 that is directly coupled to an inner surface 705 of the envelope 702 (or a substrate), and a free end 744 that extends at least partially in a Z direction toward an adjacent locking sheet 710 and is not directly coupled to the envelope 702 (or substrate). The fixed ends 742 of the islands 732 can be coupled to the envelope 702 (and/or substrate, if employed) by any of the coupling means described above with respect to FIG. 7.

In addition, the free ends 744 of the islands 732 of adjacent locking sheets 710 are configured to overlap one another (similar to a deck of cards being shuffled). As a result, each locking sheet 710 still includes islands 732 that are movable relative to one another within a major surface of the locking sheet 710, such that the apparatus 700 can be formable in a first state. However, the overlapping free ends 744 of adjacent locking sheets 710 can enhance the intimate contact between adjacent locking sheets 710 and the resulting stiffness of the apparatus 700, when the apparatus is in the second state.

In some embodiments, the islands 732 (or at least the free ends 744 thereof) can include a surface 725 oriented to face at least one adjacent locking sheet 710, e.g., one or more free ends 744 of islands 732 in an adjacent locking sheet 710. Such surfaces 725 can include high friction surfaces, and can include any of the high friction surface features or alternatives described in embodiments above.

In addition, while the locking sheets 710 are shown as being directly coupled to the envelope 702, it should be understood that the locking sheets 710 can instead be coupled to an additional substrate as described above, and/or additional locking sheets 710 can be employed, e.g., intermediately of the two locking sheets 710 shown in FIGS. 9A and 9B. For example, in some embodiments, a discontinuous locking sheet can be employed between the two illustrated locking sheets 710 that includes floating islands coupled to a top and bottom surface of a substrate. Such islands can include only fixed ends (similar to the locking sheets 510 of FIG. 7), and/or can include free ends that are configured to overlap free ends of the islands of one or both of the illustrated locking sheets 710.

Furthermore, while only two locking sheets 710 are shown for simplicity, it should be understood that as many locking sheets 710 as structurally possible or necessary can be employed in the apparatus 700, and the two locking sheets 710 are merely shown to illustrate the concept of islands 732 comprising overlapping free ends 744 that are not directly coupled to the envelope 702 (or other substrate).

For clarity purposes only, the islands 732 having overlapping free ends 744 are illustrated in FIGS. 9A-9B as angling away from the fixed ends 742, and the top and bottom sides of the of the envelope 702 are illustrated as being substantially spaced apart. However, it should be understood that this illustration is used merely to better and more clearly show how the free ends 744 of the islands 732 can overlap one another, and that, in reality, the apparatus 700 can still be sheet-like or plate-like, and the locking sheets 710 can be considered to be oriented substantially parallel to one another.

While each locking sheet 710 of FIGS. 9A-9B is shown as including only one row of islands 732, it should be understood that the locking sheets 710 can include as few as one row of islands 732, and as many as possible or necessary. The envelope 702 can be sized to accommodate more than one row. In addition, the free ends 744 of the islands 732 are shown as overlapping along one axis or direction (e.g., an X direction). If more than one row is employed, each row can include islands 732 with free ends 744 that overlap in one axis, and the rows (and the axis of each row) can be oriented substantially parallel with respect to one another. However, in some embodiments employing more than one row of islands 732, the islands 732 can be sized and shaped, and coupled to the envelope 702 (or substrate) accordingly, to allow for the islands to have free ends 744 that overlap along more than one axis or direction (e.g., in an X direction and a Y direction). Such an embodiment is illustrated in FIGS. 10A-10D and described below.

The islands 732 are shown as having a generally rectangular shape for example and illustration purposes only. However, it should be understood that the same configuration can be employed with any shape of islands 732, e.g., including, but not limited to, circles, triangles, squares, trapezoids, any other polygonal shape, irregular or random shapes, other suitable shapes, or combinations thereof. The islands 732 of one locking sheet 710 need not all be the same, and rather, in some embodiments, one locking sheet 710 can include islands 732 of a variety of shapes, sizes and/or materials. In addition, the islands 732 in each locking sheet 710 are shown as having the same shape, size, and orientation as in the adjacent locking sheet 710. However, it should be understood that adjacent locking sheets 710 need not include the islands 732 of the same shape, size or orientation. For example, in some embodiments, one of the locking sheets 710 can include square- or circular-shaped islands 732 such that only a portion of the free ends 744 of such islands 732 overlaps the free ends 744 of the islands 732 in the adjacent locking sheet 710.

In some embodiments, the apparatus 700 can include a combination of the discontinuous locking sheets 710, other discontinuous sheets (such as the discontinuous sheets 510 of FIG. 7), and/or continuous locking sheets. In such embodiments, for example, the discontinuous locking sheets can include discrete islands (i.e., with only fixed ends and/or with fixed and free overlapping ends) coupled to a substrate. The plurality of locking sheets employed in such embodiments can be arranged (e.g., at least partially stacked) in an at least partially overlapping relationship and substantially parallel configuration. In addition, in such embodiments, if a discontinuous locking sheet is employed as an intermediate locking sheet (i.e., having two adjacent locking sheets), the discontinuous locking sheet can include discrete islands coupled to a top surface and a bottom surface of the substrate. In such embodiments, the islands on either side of the substrate need not be similarly sized, shaped, and/or arranged. In addition, any intermediately positioned locking sheet can include two surfaces (e.g., a top surface and a bottom surface) oriented to face another locking sheets, and one or both of these surfaces can include a high friction surface. That is, high friction surfaces can be employed in any embodiment of the present disclosure on any surface of a locking sheet that is oriented to face another locking sheet.

Figure 10A:
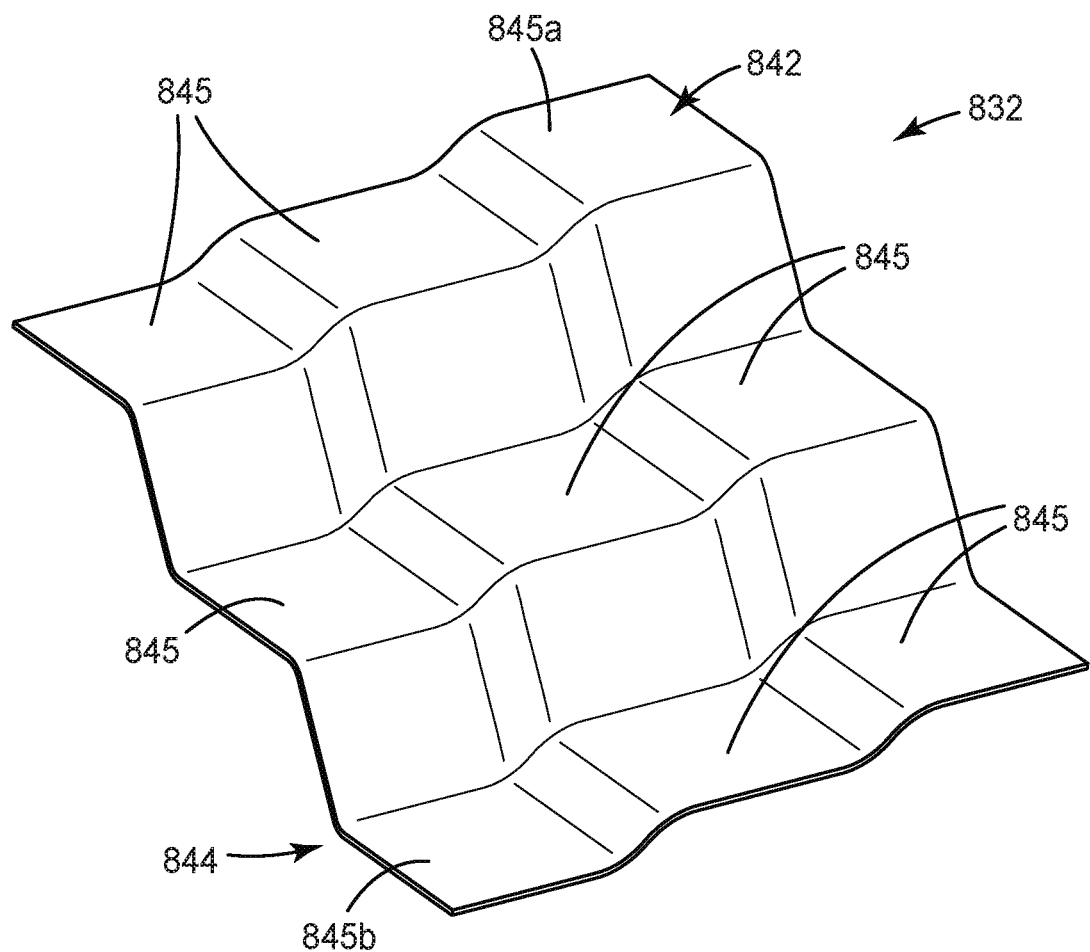
FIG. 10A is a perspective view of a discrete solid region of a locking sheet according to one embodiment of the present disclosure.
Figure 10C:
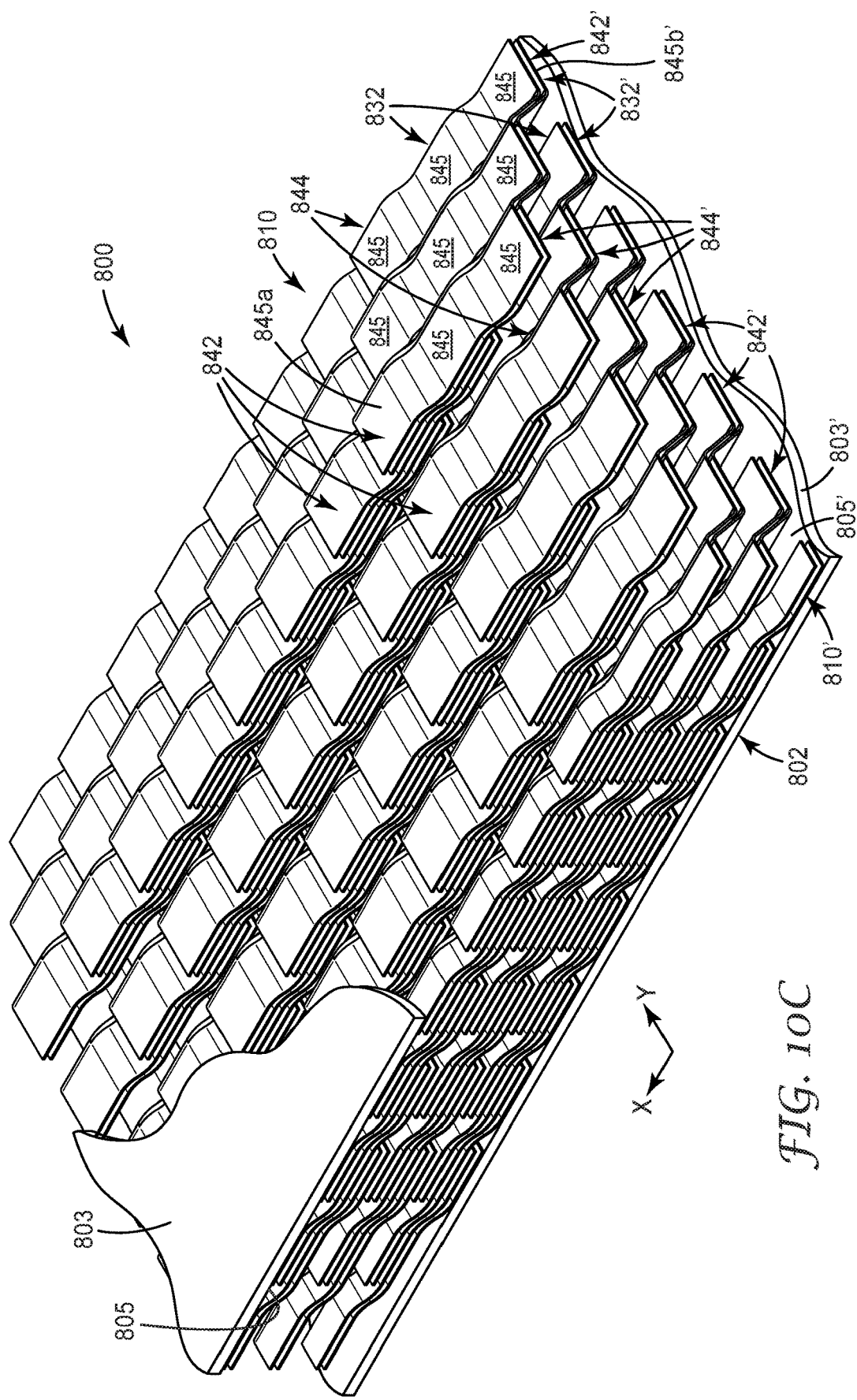
FIG. 10C is a partial cross-sectional perspective view of the shape-formable apparatus of FIG. 10B, taken along line 10C-10C.
Figure 10D:
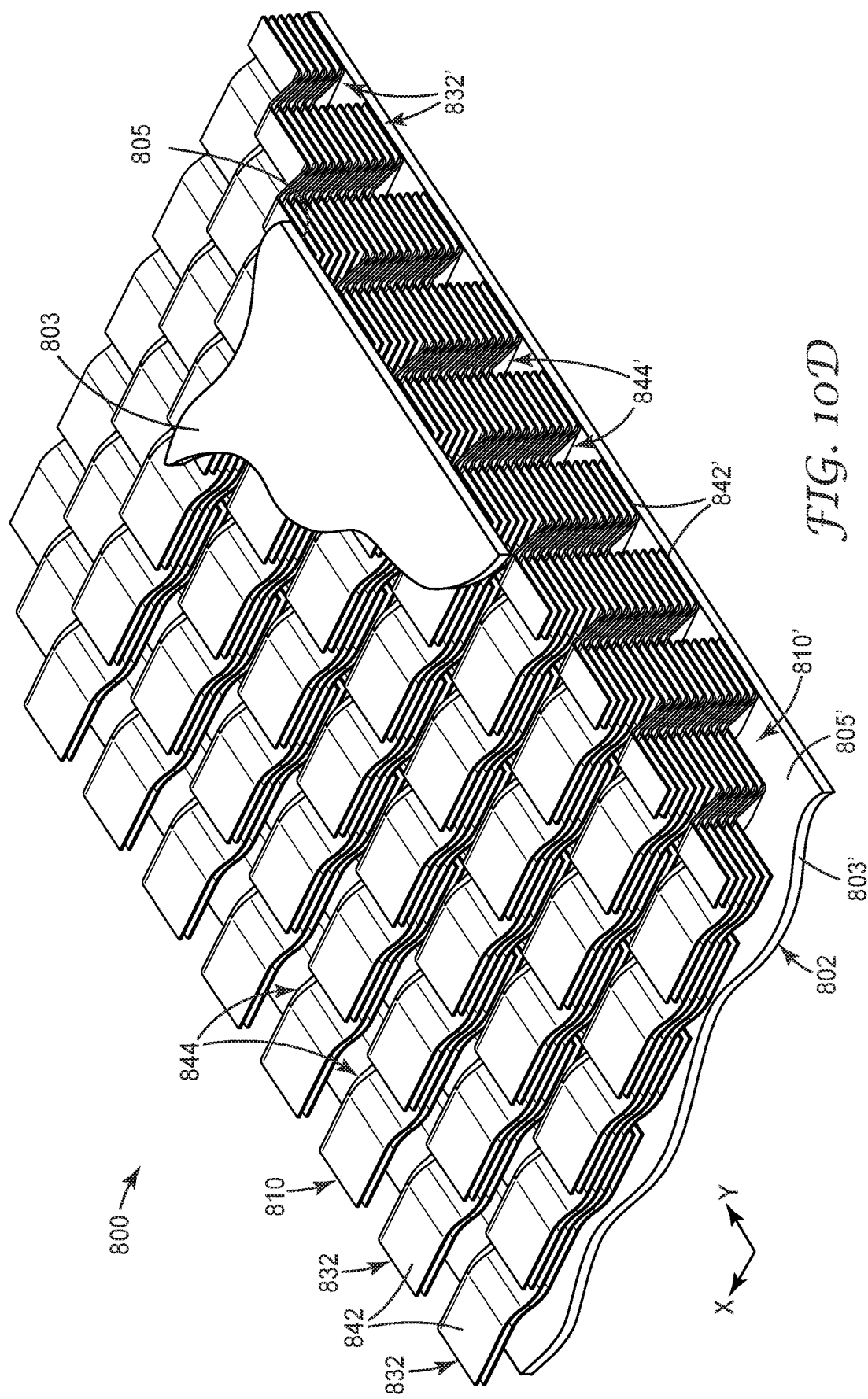
FIG. 10D is a partial cross-sectional perspective view of the shape-formable apparatus of FIG. 10B, taken along line 10D-10D.

FIGS. 10A-10D illustrate an apparatus 800 according to another embodiment of the present disclosure. FIG. 10A shows a perspective view of one island 832 according to one embodiment of the present disclosure. FIGS. 10B-10D illustrate close-up partial views of an apparatus 800 according to another embodiment of the present disclosure that employs a plurality of the islands 832 of FIG. 10A.

The apparatus 800 includes an envelope 802 that defines a chamber 804; a plurality of locking sheets 810 comprising discrete solid regions (or "islands") 832 and open regions 834; and a port (not shown, removed for clarity) positioned to fluidly couple the chamber 804 with ambience, such that a vacuum source (not shown) can be coupled to the port for evacuating the chamber 804. The apparatus 800 is generally sheet-like or plate-like and includes two discontinuous locking sheets 810 comprising islands 832 that overlap islands of an adjacent locking sheet 810 along two axes or directions.

With reference to FIG. 10A, the island 832 includes a fixed end 842 and a free end 844 and is configured to overlap islands 832 of an adjacent locking sheet 810 in two axes or directions, as shown in FIGS. 10B-10D and described below. By way of example only and for purposes of illustration, the islands 832 are shown as being formed into the three-dimensional shape shown in FIG. 10A, having nine connected platforms 845 that are all at different levels, or Z axis positions. By way of further example, the top-most platform 845a of the island 832 is shown in FIG. 10A as forming the fixed end 842 (i.e., configured to be coupled to an upper inner surface of the envelope 802, or another substrate), while the remaining platforms are included in the free end 844. However, it should be understood that the bottom-most platform 845b (i.e., an underside thereof) could instead form the fixed end 842 of the island (i.e., by being coupled to a bottom inner surface of the envelope 802, or another substrate), with the remaining platforms 845 included in the free end 844. This would be the case, for example, for islands of a lower or bottom locking sheet 810, as will be described in greater detail with respect to FIGS. 10B-10D. It should be understood that the nine-platform-shaped islands 832 are shown by way of example only for more clearly illustrating how one portion or corner (e.g., the top-most or bottom-most platform 845) of an island 832 can be coupled to the envelope 802 (or another substrate), in such a way that the rest of the island 832 can form the free end 844 that is configured to extend from the fixed end 842 to overlap one or more other islands 832 in two directions.

The apparatus 800 of FIGS. 10B-10D includes many of the same elements, features and functions as the embodiments of FIGS. 9A-9B, which also employs discontinuous locking sheets 710 that include islands 732 with free ends 744 that overlap free ends 744 of islands 732 in an adjacent locking sheet 710. Reference is made to the description above accompanying FIGS. 9A-9B for a more complete description of the features (and alternatives to such elements and features) of the embodiments of FIGS. 10A-10D.

The difference between the apparatus 800 of FIGS. 10B-10D and the apparatus 700 of FIGS. 9A-9B is that the discrete islands 832 of FIGS. 10B-10D have free ends 842 that overlap free ends 844 of islands 832 in an adjacent locking sheet 810 in more than one direction, and particularly, along two axes (e.g., an X and a Y axis, or direction). Particularly, the apparatus 800 of FIGS. 10B-10D can be understood by imagining that each of the islands 732 of the apparatus 700 of FIGS. 9A-9B has been sectioned along its width, and that the free end 744 of each island 732 not only overlaps an adjacent free end 744 of an opposing locking sheet 710 along two axes, but also overlaps the free end 744 of an adjacent island 732 on the same locking sheet 710 along two axes.

With continued reference to FIGS. 10A-10D, the fixed ends 842 of the islands 832 can be directly coupled to an inner surface 805 of the envelope 802 (or a substrate), and the free ends 844 can extend at least partially in a Z direction toward an adjacent locking sheet 810. Such free ends 844 are not directly coupled to the envelope 802 (or substrate). The fixed ends 842 of the islands 832 can be coupled to the envelope 802 (and/or substrate, if employed) by any of the coupling means described above with respect to FIG. 7.

In FIGS. 10B-10D, cutaway views of a top portion 803 and a bottom portion 803' of the envelope 802 are shown for clarity, and the top portion 803 of the envelope 802 is cutaway to better illustrate the two locking sheets 810 and the islands 832. By way of example, the apparatus 800 is shown as including a first locking sheet 810 comprising first islands 832, each first island 832 having a fixed end 842 coupled to the top portion 803 of the envelope 802 (i.e., an inner surface 805 thereof); and a second locking sheet 810' comprising second islands 832', each second island 832' having a fixed end 842' coupled to the bottom portion 803' of the envelope 802' (i.e., an inner surface 805' thereof).

All nine platforms 845 of the far right, top first island 832 of the first locking sheet 810 are visible in FIGS. 10B and 10C. Particularly, the top-most platform 845a forms the fixed end 842 that is coupled to the top portion 803 of the envelope 802, and the remaining platforms form the free end 844 of the island 832. A second island 832' of the second locking sheet 810' that is overlapped by the first island 832 of the first locking sheet 810 includes a bottom-most platform 845b' (i.e., an underside thereof) that forms the fixed end 842' of the second island 832' that is coupled to the bottom portion 803' of the envelope 802. This pattern of overlapping first and second islands 832, 832' is then continued in the X and Y directions, so that each first island 832 of the first locking sheet 810 directly overlaps a second island 832' of the second locking sheet 810', and the respective free ends 844, 844' of the pair of first and second islands 832, 832' overlaps a similar pair of islands 832, 832' in the X direction and the Y direction, and so on, as further shown in FIGS. 10C and 10D. FIGS. 10C and 10D show cross-sectional perspective views to further illustrate how pairs of the first and second islands 832, 832' of the first and second locking sheets 810, 810' overlap along two axes.

As with other embodiments discussed above, other shapes, sizes and arrangements of the islands 832 can be employed in the apparatus 800 without departing from the present disclosure. In addition, while the islands 832 of the apparatus 800 are shown as all having the same shape and size, it should be understood that these need not be the case. Furthermore, in some embodiments, the apparatus 800 can include a combination of the discontinuous locking sheets 810 of FIGS. 10B-10D and one or more of (i) fixed-end only discontinuous locking sheets (see, e.g., the islands 532 of FIG. 7); and (ii) continuous locking sheets. Furthermore, in some embodiments, the islands 832 (e.g., the free ends 844 thereof) can include one or more surfaces oriented to face an adjacent locking sheet 810, and such surfaces can include high friction surfaces, as described above.

FIGS. 11-25 illustrate various embodiments of continuous locking sheet patterns (i.e., employing continuous solid regions) of the present disclosure, wherein like numerals represent like elements. Such locking sheets can be employed in any of the apparatuses of the present disclosure.

Figure 11:
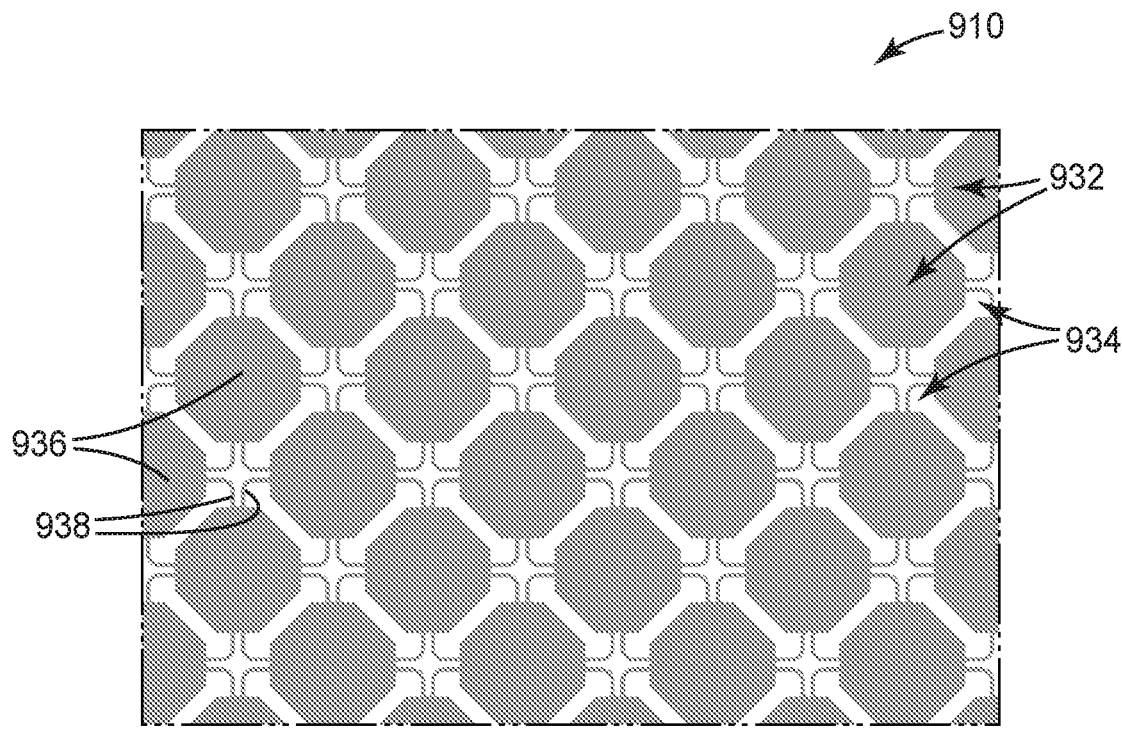
FIGS. 11-25 are each a top plan view of a locking sheet comprising continuous solid regions according to another embodiment of the present disclosure.

FIG. 11 illustrates a locking sheet 910 according to one embodiment of the present disclosure. The locking sheet 910 includes solid regions 932 and open regions 934. The solid regions 932 include islands 936 having an octagonal shape, and each island 936 is connected to each adjacent island 936 by two bridges 938, as described in greater detail below. The pattern of the locking sheet 910 is similar to the locking sheets 110 of FIGS. 1 and 4, except that in the locking sheet 910, each island includes four sides or edges that are each connected to two bridges 938 instead of only one.

As shown in FIG. 11, the islands 936 are arranged in a square-packed arrangement, such that the pattern of the locking sheet 910 includes a repeat unit, or unit cell, that can be propagated in any direction (i.e., left, right, up, down), comprising one central octagonal island 936 that is connected to four adjacent islands 936 by eight bridges 938, i.e., two bridges 938 per adjacent island 936. The bridges 938 are equally-spaced about the central island 936, such that every other octagonal edge of the central island 936 is connected to two bridges 938. By way of example, each bridge 938 includes a 90-degree bend, and each pair of bridges 938 coming from the same edge of an island 936 bend in opposite directions from one another, i.e., clockwise and counter-clockwise, such that the open regions 934 include a repeat unit comprising a substantially square space between four adjacent islands 936 that includes four bridges 938 bending toward a center of the square space, and such that the pattern of the first locking sheet 910 includes 4-fold rotational symmetry about the center of each island 936, in addition to 4 axes of symmetry.

Figure 12:
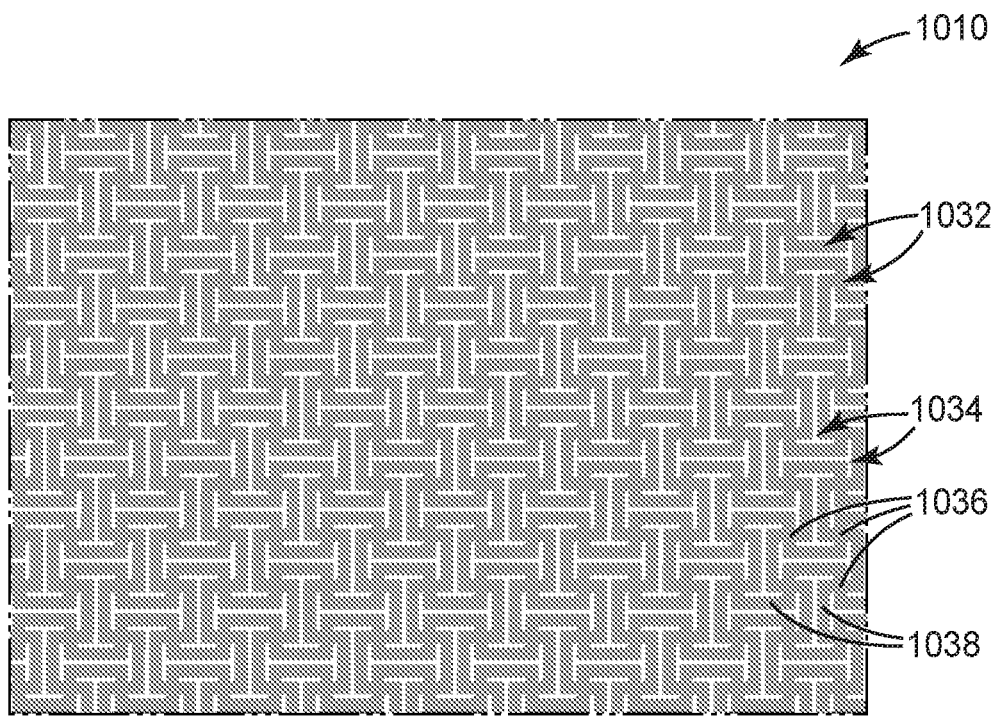

FIG. 12 illustrates a locking sheet 1010 according to another embodiment of the present disclosure. The locking sheet 1010 includes solid regions 1032 and open regions 1034. The solid regions 1032 include islands 1036 having a substantially square shape, and each island 1036 is connected to each adjacent island 1036 by one bridge 1038, respectively. As shown in FIG. 12, the islands 1036 are arranged in a square-packed arrangement, such that the pattern of the locking sheet 1010 includes a repeat unit, or unit cell, comprising four adjacent and connected islands 1036 arranged in a square. Each island 1036 in FIG. 12 is connected to four adjacent islands 1036 by four bridges 1038, respectively. For example, a first island 1036 is connected to one island 1036 above and one island 1036 below on the same vertical line as the first island 1036; and the first island 1036 is connected to one island 1036 on the left and one island 1036 on the right on the same horizontal line as the first island 1036. Each bridge 1038 extends from one edge of the first square island 1036 and has the same width as the edge of the first square island 1036.

By way of example, each bridge 1038 includes two 90-degree bends that are spaced a greater distance apart than the bends are spaced from an island 1036, such that the open regions 1034 in the pattern include alternating horizontal and vertical "I" shapes. The pattern of the locking sheet 1010 includes lines of symmetry along the lengths of the "I"-shaped open regions 1034 oriented horizontally and vertically. In addition, the angles of the two 90-degree bends sum to 180 degrees, such that a first bend in a bridge 1038 as it extends from an island 1036 bends clockwise or counter-clockwise (left or right), and a second bend in the same bridge 1038 bends again in the same direction, i.e., clockwise or counter-clockwise (left or right), before connecting to the adjacent island 1036.

Each island 1036 has four bridges 1038 extending from it that all bend in the same direction (i.e., clockwise or counter-clockwise). However, each island 1036 has bridges 1038 bending in the opposite direction (i.e., counter-clockwise or clockwise) as that of the bridges 1038 extending from one of its connected, adjacent islands 1036.

Figure 13:
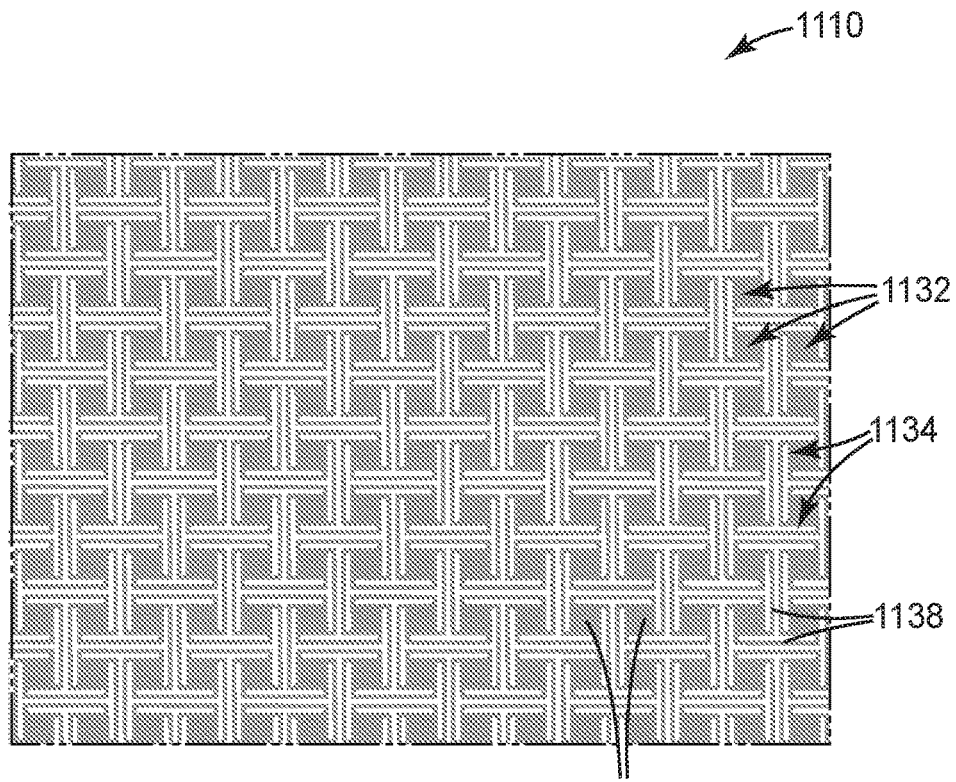

FIG. 13 illustrates a locking sheet 1110 according to another embodiment of the present disclosure. The locking sheet 1110 includes solid regions 1132 and open regions 1134. The solid regions 1132 include islands 1136 having a substantially square shape, and each island 1136 is connected to each adjacent island 1136 by one bridge 1138, respectively. The pattern shown in FIG. 13 is substantially the same as that of FIG. 12, except that the relative sizing of islands 1136 to bridges 1138 has been changed. Particularly, the width of each bridge 1138 of the locking sheets 1110 of FIG. 13 is substantially less than an edge of each island 1136. In addition, each bridge 1138 is positioned to extend from an edge of an island 1136, directly adjacent one of the corners of the square island 1136. As a result, the tops and bottoms of the vertically-oriented "I"-shaped open regions 1134 are positioned closer to the long middle segments of the horizontally-oriented "I"-shaped open regions 1134, and the tops and bottoms of the horizontally-oriented "I"-shaped open regions 1134 are positioned closer to the long middle segments of the vertically-oriented "I"-shaped open regions 1134.

Figure 14:
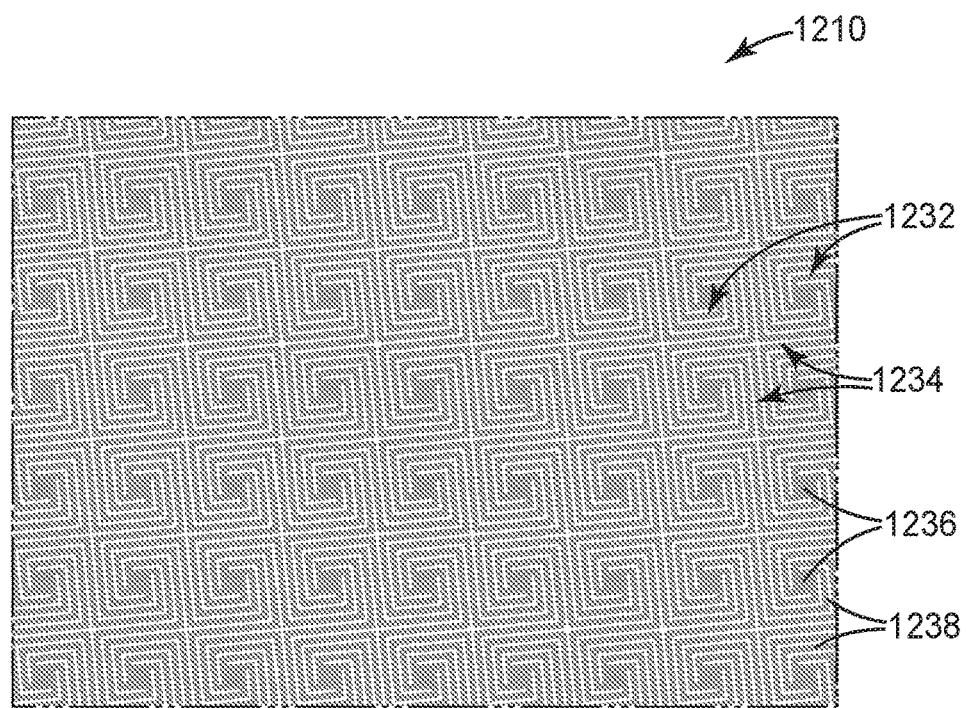

FIG. 14 illustrates a locking sheet 1210 according to another embodiment of the present disclosure. The locking sheet 1210 includes solid regions 1232 and open regions 1234. The solid regions 1232 include islands 1236 having a substantially square shape, and each island 1236 is connected to each adjacent island 1236 by one bridge 1238, respectively. As shown in FIG. 14, the islands 1236 are arranged in a square-packed arrangement, such that the pattern of the locking sheet 1210 includes a repeat unit, or unit cell, comprising one island 1236 and a portion of its four bridges 1238 extending therefrom to adjacent islands 1236. Each island 1236 in FIG. 14 is connected to four adjacent islands 1236 by four bridges 1238, respectively. For example, a first island 1236 is connected to one island 1236 above and one island 1236 below; and the first island 1236 is further connected to one island 1236 on its left and one island 1236 on its right. Each bridge 1238 has a width that is substantially less than the width of one side or edge of the island 1236 and extends from a side of the island 1236 directly adjacent a corner of the square island 1236.

By way of example, each bridge 1238 includes eight 90-degree bends, the first four bends all going in the same direction (i.e., clockwise) to spiral outwardly around the island 1236 from which it extends, the second four bends all going in the opposite direction (i.e., counter-clockwise) to spiral inwardly around and to an adjacent island 1236. As a result, the lengths of a bridge 1238 between its adjacent bends progressively increase around the island 1236 from which it extends, while the lengths of the bridge 1238 between its adjacent bends progressively decrease around the adjacent islands 1236 to which it extends and connects.

Figure 15:
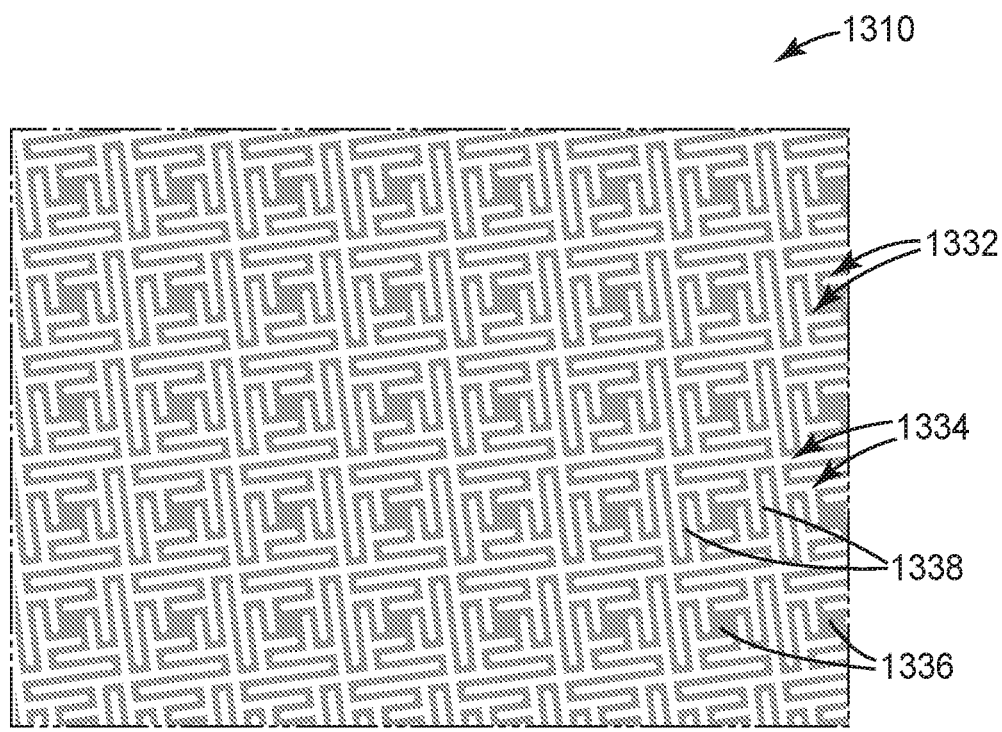

FIG. 15 illustrates a locking sheet 1310 according to another embodiment of the present disclosure. The locking sheet 1310 includes solid regions 1332 and open regions 1334. The solid regions 1332 include islands 1336 having a substantially square shape, and each island 1336 is connected to each adjacent island 1336 by one bridge 1338, respectively. As shown in FIG. 15, the islands 1336 are arranged in a square-packed arrangement, such that the pattern of the locking sheet 1310 includes a repeat unit, or unit cell, comprising one island 1336 and a portion of its four bridges 1338 extending therefrom to adjacent islands 1336. Each island 1336 in FIG. 15 is connected to four adjacent islands 1336 by four bridges 1338, respectively. For example, a first island 1336 is connected to one island 1336 above and one island 1336 below; and the first island 1336 is further connected to one island 1336 on its left and one island 1336 on its right. Each bridge 1338 has a width that is substantially less than the width of one side or edge of the island 1336 and extends from a side of the island 1336 directly adjacent a corner of the square island 1336.

By way of example, each bridge 1338 includes ten 90-degree bends; or a first 90-degree bend, followed by four 180-degree bends to essentially zig-zag outwardly from a side of one island 1336 toward a side of an adjacent island 1336, followed by a final 90-degree bend to connect to the adjacent island 1336. The first 90-degree bend coming from each side of a given island 1336 turns in the same direction (i.e., clockwise, or right), and the final 90-degree bend into an adjacent island 1336 turns in the opposite direction (i.e., counter-clockwise, or left). The lengths between adjacent bends of a bridge 1338 progressively increase, as the bridge 1338 zig-zags to a position that is about midway between two adjacent islands 1336, and then progressively decrease toward the adjacent island 1336.

Figure 16:
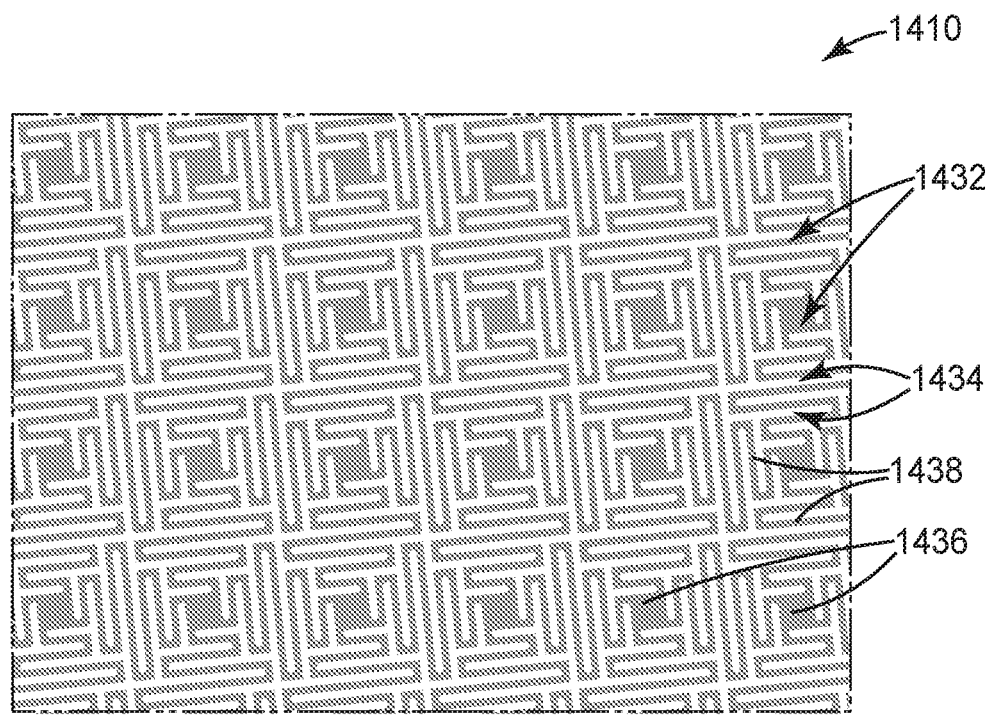

FIG. 16 illustrates a locking sheet 1410 according to another embodiment of the present disclosure. The locking sheet 1410 includes solid regions 1432 and open regions 1434. The solid regions 1432 include islands 1436 having a substantially square shape, and each island 1436 is connected to each adjacent island 1436 by one bridge 1438, respectively. The pattern shown in FIG. 16 is substantially the same as that of FIG. 15, except for the following: (i) the scale of FIG. 16 is different from FIG. 15; the islands 1436 and bridges 1438 of FIG. 16 are larger, such that the locking sheet 1410 of FIG. 16 includes fewer islands 1436 per area; (ii) each bridge 1438 includes fourteen 90-degree bends; or a first 90-degree bend, followed by six 180-degree bends to essentially zig-zag outwardly from a side of one island 1436 toward a side of an adjacent island 1436, followed by a final 90-degree bend to connect to the adjacent island 1436; and (iii) the first 90-degree bend coming from each side of a given island 1436 turns counter-clockwise (or left), and the final 90-degree bend into an adjacent island 1436 turns in the opposite direction, i.e., clockwise, or right).

Figure 17:
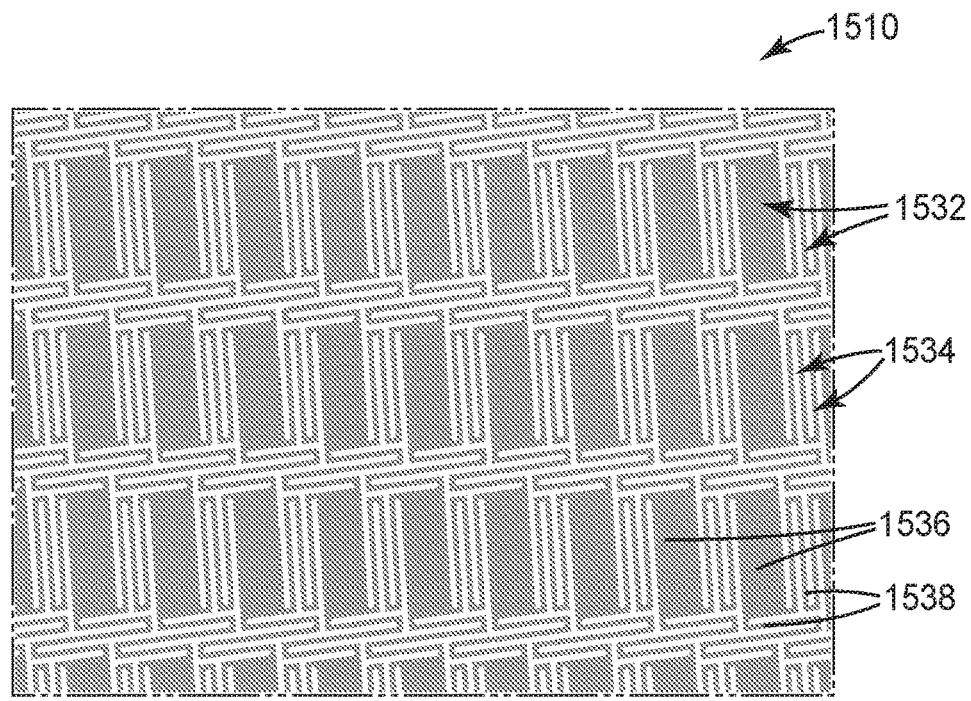

FIG. 17 illustrates a locking sheet 1510 according to another embodiment of the present disclosure. The locking sheet 1510 includes solid regions 1532 and open regions 1534. The solid regions 1532 include islands 1536, and each island 1536 is connected to each adjacent island 1536 by one bridge 1538, respectively. The pattern shown in FIG. 17 is substantially the same as that of FIG. 16, except for the following: (i) the islands 1536 have a substantially rectangular (or elongated parallelogram) shape; (ii) each bridge 1538 includes six 90-degree bends; or a first 90-degree bend, followed by two 180-degree bends to zig-zag outwardly from a side of one island 1536 toward a side of an adjacent island 1536, followed by a final 90-degree bend to connect to the adjacent island 1536; (iii) the lengths between adjacent bends of a bridge 1538 extending from a long side of an island 1536 are all approximately the same as one another and do not progressively increase and then decrease like they do on the short side of the island 1536; and (iv) the spacing (i.e., the open regions 1534) between the islands 1536 and bridges 1538 of FIG. 17 is narrower.

Figure 18:
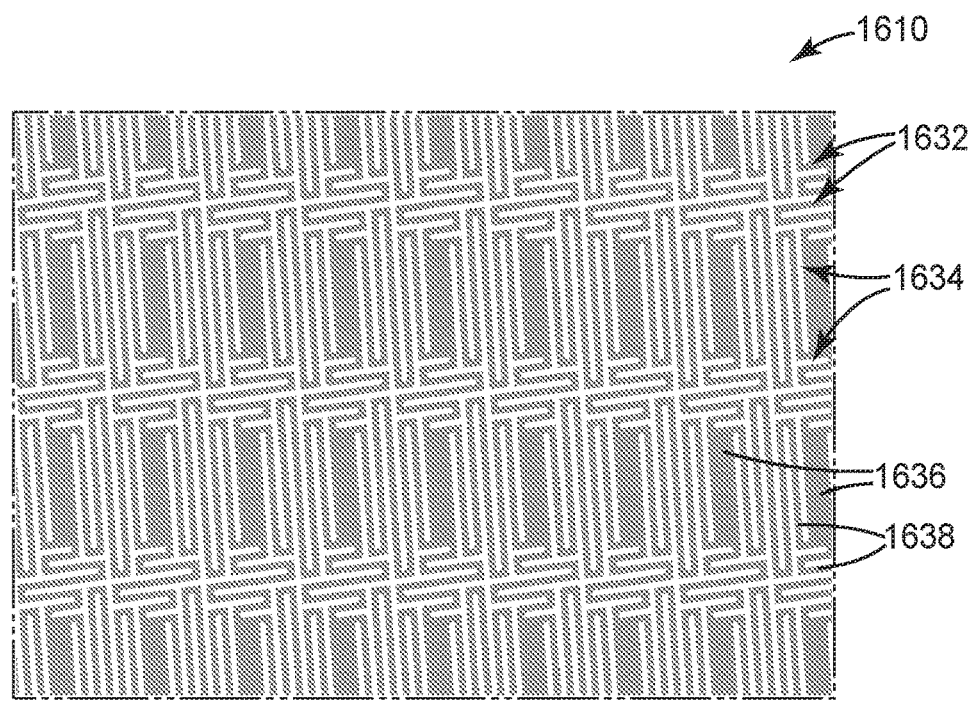

FIG. 18 illustrates a locking sheet 1610 according to another embodiment of the present disclosure. The locking sheet 1610 includes solid regions 1632 and open regions 1634. The solid regions 1632 include islands 1636 having a substantially rectangular (or elongated parallelogram) shape, and each island 1636 is connected to each adjacent island 1636 by one bridge 1638, respectively. The pattern shown in FIG. 18 is substantially the same as that of FIG. 15, except for the following: (i) the islands 1536 have a substantially rectangular (or elongated parallelogram) shape; and (ii) the spacing (i.e., the open regions 1634) between the islands 1636 and bridges 1638 of FIG. 18 is narrower.

Figure 19:
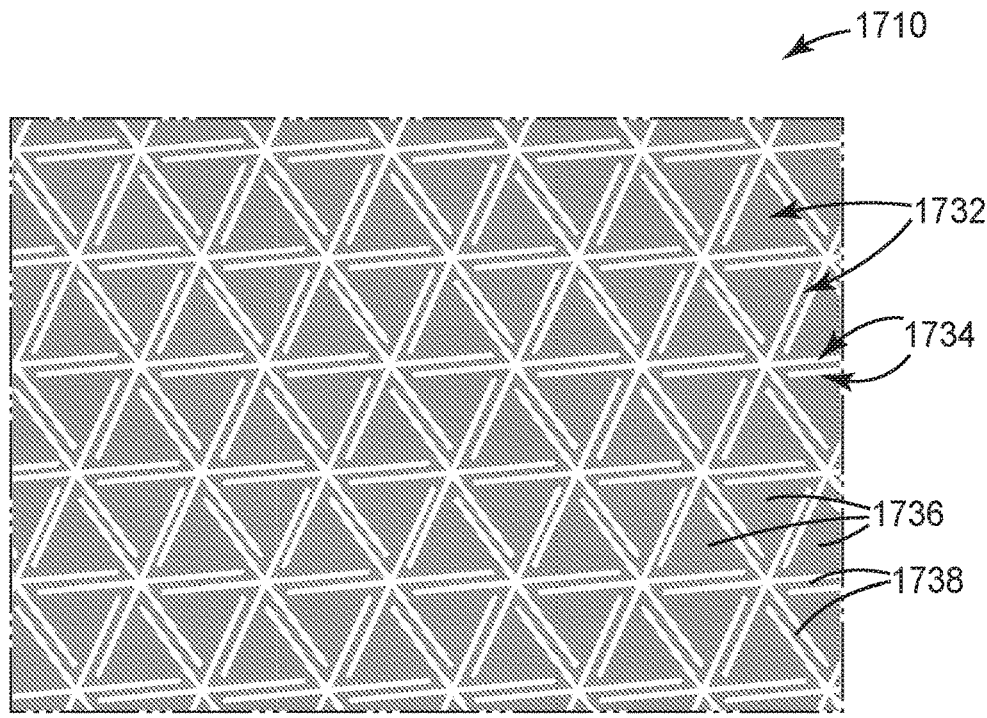

FIG. 19 illustrates a locking sheet 1710 according to another embodiment of the present disclosure. The locking sheet 1710 includes solid regions 1732 and open regions 1734. The solid regions 1732 include islands 1736 having the shape of an equilateral triangle, and each island 1736 is connected to each adjacent island 1736 by one bridge 1738, respectively. The open regions 1734 include six-legged asterisk- or star-shaped cutouts that are densely packed, such that each leg of one asterisk-shaped open region 1734 substantially overlaps a leg of an adjacent asterisk-shaped open region 1734.

As shown in FIG. 19, the islands 1736 are arranged in a hexagonally-packed arrangement, such that the pattern of the locking sheet 1710 includes a repeat unit, or unit cell, comprising six triangular islands 1736 arranged into a hexagon and a portion of the bridges 1738 extending therefrom to adjacent islands 1736. Each island 1736 in FIG. 19 is connected to three adjacent islands 1736 by three bridges 1738, respectively. For example, a first island 1736 is connected to one island 1736 above or below, one island 1736 on one side, and another island 1736 on the other side. Each bridge 1738 has a width that is substantially less than the width of one side or edge of the island 1736 and extends from a side of the island 1736 directly adjacent a corner of the triangular island 1736.

By way of example, each bridge 1738 includes an immediate first 60-degree bend and a second 60-degree bend to connect to another island 1736, and the length of the bridge 1738 between the two 60-degree bends is about equal to one side of a triangular island 1736, such that each bridge 1738, between the two 60-degree bends, runs along and between a side of a first island 1736 and a side of a second, adjacent, island 1736. The first 60-degree bend in each bridge 1738 coming from an island 1736 turns in the same direction (i.e., clockwise, or right), and the second 60-degree bend into an adjacent island 1736 turns in the opposite direction (i.e., counter-clockwise, or left).

Figure 20:
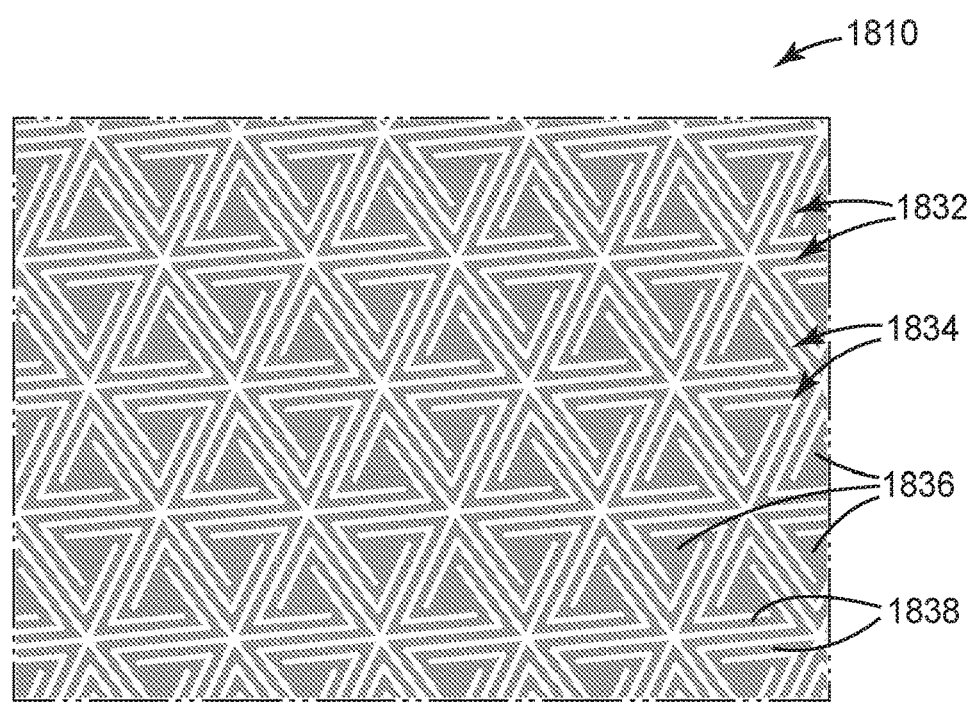

FIG. 20 illustrates a locking sheet 1810 according to another embodiment of the present disclosure. The locking sheet 1810 includes solid regions 1832 and open regions 1834. The solid regions 1832 include islands 1836, and each island 1836 is connected to each adjacent island 1836 by one bridge 1838, respectively. The pattern shown in FIG. 20 is substantially the same as that of FIG. 19, except that each bridge 1838 includes four 60-degree bends, such that each side of an island 1836 is separated from a side of an adjacent island 1836 by three bridges 1838, and the lengths of a bridge 1838 between adjacent bends increase as the bridge 1838 extends around an island 1836 to a position where the bridge 1838 runs between the two adjacent islands 1836 it connects, and then decrease as the bridge 1838 extends around and connects to a side of the adjacent island 1836. In addition, each leg of the six-legged asterisk-shaped open regions 1834 includes a pronged end that is bent at 60 degrees with respect to the leg from which it extends.

Figure 21:
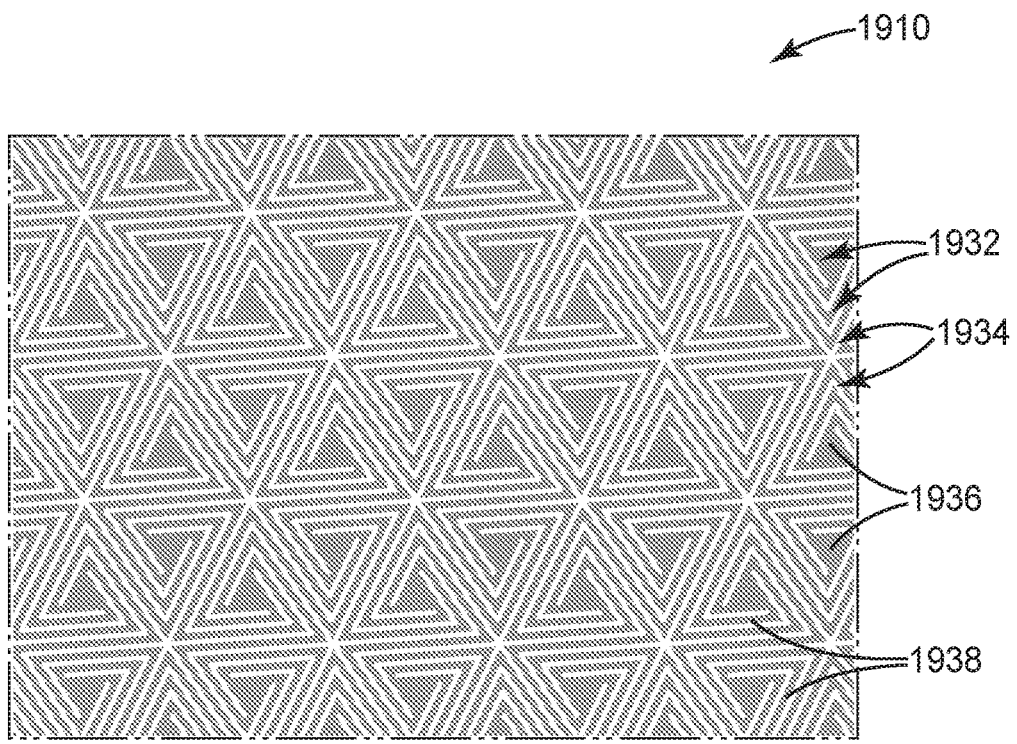

FIG. 21 illustrates a locking sheet 1910 according to another embodiment of the present disclosure. The locking sheet 1910 includes solid regions 1932 and open regions 1934. The solid regions 1932 include islands 1936, and each island 1936 is connected to each adjacent island 1936 by one bridge 1938, respectively. The pattern shown in FIG. 21 is substantially the same as that of FIGS. 19 and 20, except that each bridge 1938 includes six 60-degree bends, with the first three bends bending in the same direction (i.e., clockwise) around the island 1936 from which the bridge 1938 extends, and the second three bends bending in the opposite direction (i.e., counter-clockwise) around an adjacent island 1936.

Each side of an island 1936 is separated from a side of an adjacent island 1936 by five bends (or portions of a bridge 1938), and the lengths of a bridge 1938 between adjacent bends increase as the bridge 1938 extends around an island 1936 to a position where the bridge 1938 runs between the two adjacent islands 1936 it connects, and then decrease as the bridge 1938 extends around and connects to a side of the adjacent island 1936.

Figure 22:
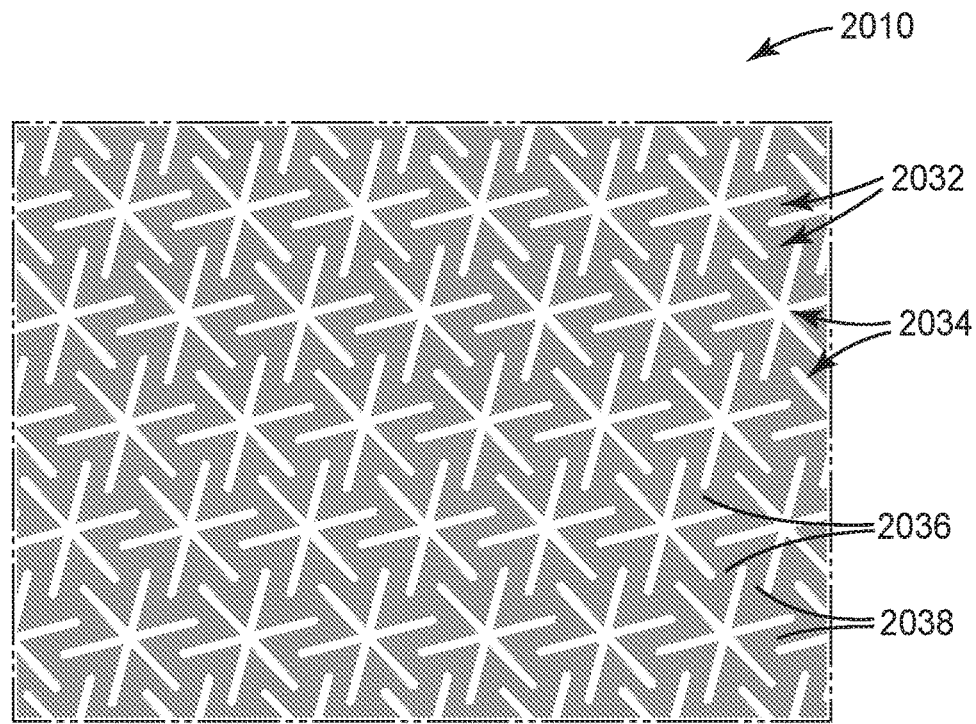

FIG. 22 illustrates a locking sheet 2010 according to another embodiment of the present disclosure. The locking sheet 2010 includes solid regions 2032 and open regions 2034. The solid regions 2032 include islands 2036, and each island 2036 is connected to each adjacent island 2036 by one bridge 2038, respectively. The pattern shown in FIG. 22 is substantially the same as that of FIG. 20, except that the width of each bridge is the same as the width of each side of the triangular island 2036 (and the islands 2036 are less obviously triangular in shape). As a result, the asterisk-shaped open regions 2034 are smaller, the legs of the asterisk-shaped open regions 2034 are wider, the legs of one asterisk-shaped open region 2034 are spaced further from the legs of adjacent open regions 2034, and the legs only partially overlap those of adjacent open regions 2034.

Figure 23:
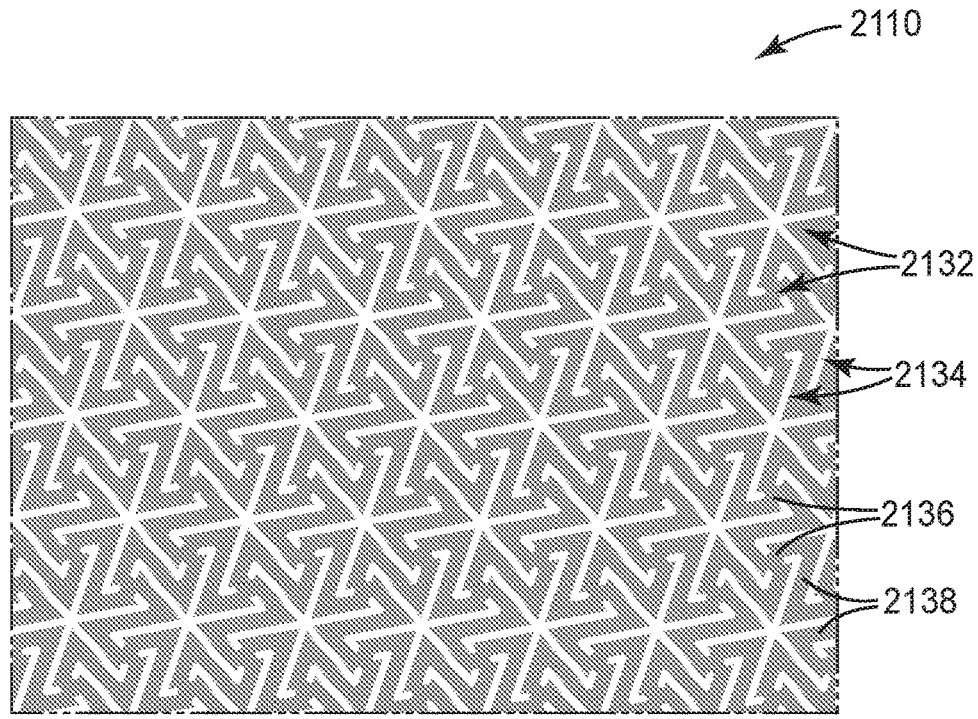

FIG. 23 illustrates a locking sheet 2110 according to another embodiment of the present disclosure. The locking sheet 2110 includes solid regions 2132 and open regions 2134. The solid regions 2132 include islands 2136, and each island 2136 is connected to each adjacent island 2136 by one bridge 2138, respectively. The pattern shown in FIG. 23 is substantially the same as that of FIG. 22, except that each bridge 2138 includes four 60-degree bends, such that each side of an island 2136 is separated from a side of an adjacent island 2136 by three bridges 2138, and the lengths of a bridge 2138 between adjacent bends increase as the bridge 2138 extends around an island 1836 to a position where the bridge 2138 runs between the two adjacent islands 2136 it connects, and then decrease as the bridge 2138 extends around and connects to a side of the adjacent island 2136. In addition, each leg of the six-legged asterisk-shaped open regions 2134 includes a pronged end that is bent at 60 degrees with respect to the leg from which it extends.

Figure 24:
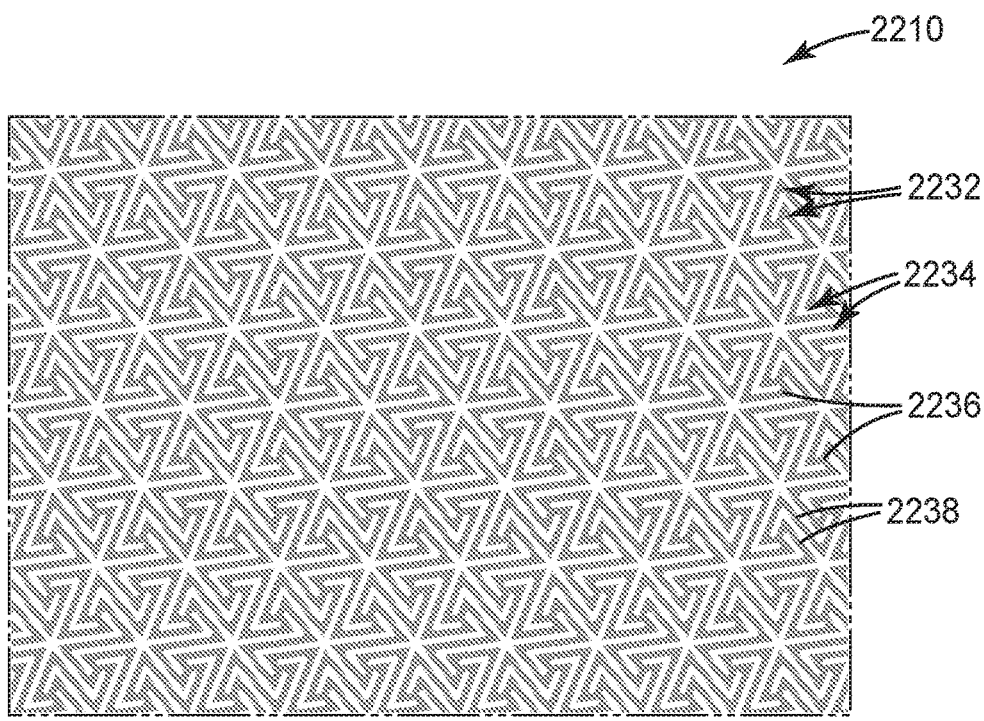

FIG. 24 illustrates a locking sheet 2210 according to another embodiment of the present disclosure. The locking sheet 2210 includes solid regions 2232 and open regions 2234. The solid regions 2232 include islands 2236, and each island 2236 is connected to each adjacent island 2236 by one bridge 2238, respectively. The pattern shown in FIG. 24 is substantially the same as that of FIG. 23, except that the asterisk-shaped open regions 2234 are more densely packed, such that each leg of one asterisk-shaped open region 2234 substantially overlaps a leg of an adjacent asterisk-shaped open region 2234. As a result, the islands 2234 of FIG. 24 are smaller than those of FIG. 23, and the bridges 2238 of FIG. 24 are narrower than those of FIG. 23.

Figure 25:
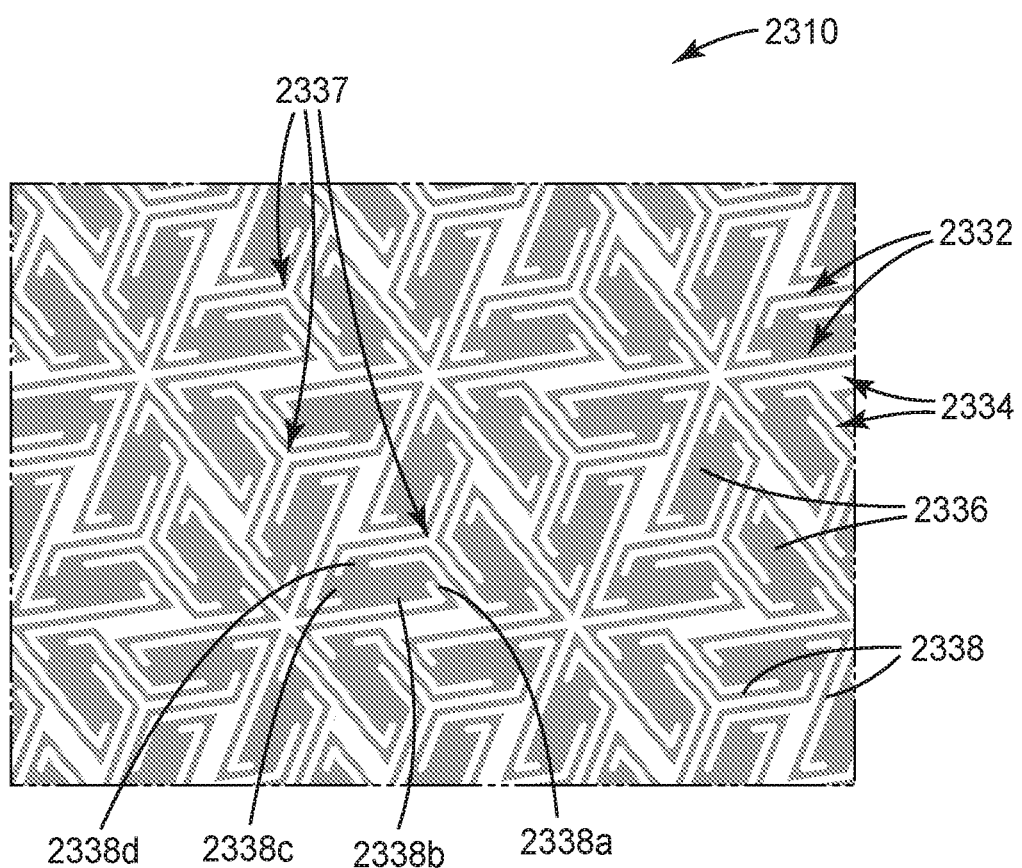

FIG. 25 illustrates a locking sheet 2310 according to another embodiment of the present disclosure. The locking sheet 2310 includes solid regions 2332 and open regions 2334. The solid regions 2332 include islands 2336, and each island 2336 is connected to each adjacent island 2336 by one bridge 2338, respectively. Each individual island 2336 has trapezoidal shape (particularly, an elongated trapezoidal shape with two longer sides and two short sides), and is connected to four adjacent islands 2336 by four bridges 2338, respectively. Particularly, one bridge 2338 extends from each side or edge of each island 2336, directly adjacent a corner of the island 2336, and immediately turning to extend alongside (while also being integral with) the side of the island 2336 from which the bridge 2338 extends. The pattern of the locking sheet 2310 further includes a plurality of island clusters or groups 2337, each cluster 2337 comprising three trapezoidal islands 2336 arranged to form a generally triangular shape, and particularly, arranged such that the shorter long side of each trapezoidal island 2336 is oriented to face a short side of an adjacent island 2336 within the same cluster 2337. Six triangular clusters 2337 of islands 2336 are arranged about a center to form a generally hexagonal repeat unit, or unit cell, for the pattern of the locking sheet 2310. As a result, the island clusters 2337 are arranged in a hexagonally-packed arrangement.

Each island 2336 has four bridges 2338, as mentioned above:
- (i) a first bridge 2338a that extends from a first short side of the trapezoidal island 2336 and includes a clockwise 120-degree bend, followed by a clockwise 60-degree bend, followed by a counter-clockwise 60-degree bend, and followed by a counter-clockwise 60-degree bend to connect to an adjacent island 2336;
- (ii) a second bridge 2338b that extends from the longest side of the island 2336 and includes a clockwise 60-degree bend, followed by a clockwise 60-degree bend, followed by a counter-clockwise 60-degree end, and followed by counter-clockwise 120 degree bend to connect to an adjacent island 2336;
- (iii) a third bridge 2338c that extends from a second short side of the island 2336 and includes a clockwise 60-degree bend, followed by a clockwise 120-degree bend, followed by a counter-clockwise 120-degree bend, and followed by counter-clockwise 120-degree bend to connect to an adjacent island 2336; and
- (iv) a fourth bridge 2338d that extends outwardly from the shorter of the long sides and includes a clockwise 120-degree bend, after which the fourth bridge 2338d is not connected to the island 2336 but extends adjacent the shorter long side, followed by a clockwise 120-degree bend, followed by a counter-clockwise 120-degree bend, and followed a counter-clockwise 60 degree bend to connect to an adjacent island 2336.

The locking sheet patterns of FIGS. 11-25 are shown by way of example only; however, it should be understood that other suitable patterns can also be employed in the locking sheets of the present disclosure. In addition, the relative sizing (i.e., aspect ratios), spacing, etc. of any of the patterns of FIGS. 11-25 can be changed from exactly what is shown without departing from the spirit and scope of the present disclosure.

Furthermore, each embodiment of the shape-formable apparatuses shown in the figures is illustrated as a separate embodiment for clarity in illustrating a variety of features of the shape-formable apparatuses of the present disclosure. However, it should be understood that any combination of elements and features of any of the embodiments illustrated in the figures and described herein can be employed in the shape-formable apparatuses of the present disclosure. For example, any of the description of the features and elements (and alternatives to such features and elements) of the shape-formable apparatus 100 of FIGS. 1, 4 and 5 (e.g., regarding material makeup of the envelope 102 or the locking sheets 110, the methods of making the envelope 102 or the locking sheets 110, various configurations or arrangements of the locking sheets 110, or any other detail) can be applied to the embodiments of FIGS. 2-3 and 6A-10D. In addition, any of the locking patterns of FIGS. 11-25 can be employed in any shape-formable apparatus embodiment of the present disclosure.

The following embodiments are intended to be illustrative of the present disclosure and not limiting.

EMBODIMENTS

1. A shape-formable apparatus comprising:
   a first state in which the apparatus is formable, such that the apparatus can be formed into a desired shape;
   a second state in which the apparatus has the desired shape and is substantially less formable than in the first state;
   an envelope defining a chamber, the envelope formed of a gas-impermeable material;
   a port positioned to fluidly couple the chamber with ambience; and
   at least two locking sheets positioned in the chamber in an at least partially overlapping configuration, wherein each locking sheet comprises a major surface, and wherein at least a portion of each locking sheet is patterned to include solid regions and open regions, the solid regions being movable with respect to one another within the major surface.

2. The apparatus of embodiment 1, wherein the solid regions are movable with respect to one another within the major surface from a first position to a second position that can be maintained, without plastic deformation, after an applied force is removed.

3. The apparatus of embodiment 1 or 2, wherein the solid regions of at least one locking sheet are formed of a material having an effective tensile modulus ($E_o$), and wherein the solid regions and open regions are arranged in the at least one locking sheet such that the at least one locking sheet has an overall effective tensile modulus ($E_l$), and wherein the ratio of $E_o/E_l$ for each locking sheet is at least 2.

4. The apparatus of embodiment 3, wherein the ratio of $E_o/E_l$ for the at least one locking sheet is at least 2 in any direction within the major surface of each locking sheet.

5. The apparatus of embodiment 3 or 4, wherein the ratio of $E_o/E_l$ for the at least one locking sheet is at least 10.

6. The apparatus of any of embodiments 3-5, wherein the ratio of $E_o/E_l$ for the at least one locking sheet is at least 100.

7. The apparatus of any of embodiments 1-6, wherein the solid regions of at least one locking sheet are formed of a material having a first effective tensile modulus ($E_o$), and wherein the apparatus has an overall effective tensile modulus ($E_a$) when the apparatus is in the first state, and wherein the ratio of $E_o/E_a$ is at least 2.

8. The apparatus of any of embodiments 1-7, wherein the at least two locking sheets are oriented substantially parallel with respect to one another.

9. The apparatus of any of embodiments 1-8, wherein the apparatus has a first stiffness in the first state and a second stiffness in the second state, and wherein the stiffness ratio of the second stiffness to the first stiffness is at least 2.

10. The apparatus of any of embodiments 1-9, wherein the apparatus has a first effective tensile modulus ($E_{UL}$) when in the first state and a second effective tensile modulus ($E_L$) when in the second state, and wherein the ratio of the second modulus to the first modulus ($E_L/E_{UL}$) is at least 2.

11. The apparatus of any of embodiments 1-10, wherein the apparatus is configured to substantially conform to a complex surface having a non-zero Gaussian curvature when the apparatus is in the first state.

12. The apparatus of any of embodiments 1-11, wherein at least one locking sheet is configured to substantially conform to a complex surface having a non-zero Gaussian curvature.

13. The apparatus of any of embodiments 1-12, wherein the solid regions of at least one locking sheet are formed of a material having a strain at yield ($\varepsilon_o$), wherein the solid regions and the open regions are arranged such that the at least one locking sheet is configured to experience a strain ($\varepsilon_t$) without yielding when the apparatus is in the first state, and wherein the strain ratio of $\varepsilon_t/\varepsilon_o$ is at least 1.

14. The apparatus of any of embodiments 1-13, wherein the chamber is evacuated in the second state, relative to the first state.

15. The apparatus of any of embodiments 1-14, wherein the at least two locking sheets are movable relative to one another in the chamber when the apparatus is in the first state but are substantially immovable relative to one another when the apparatus is in the second state.

16. The apparatus of any of embodiments 1-15, wherein each locking sheet includes a surface oriented to face another locking sheet, and wherein the surface includes a high friction surface.

17. The apparatus of any of embodiments 1-16, wherein each locking sheet includes a surface oriented to face another locking sheet, and wherein at least a portion of the surface of at least one locking sheet is structured.

18. The apparatus of any of embodiments 1-17, wherein the at least two locking sheets includes a first locking sheet comprising a first surface oriented to face a second locking sheet and a second locking sheet comprising a second surface oriented to face the first locking sheet, wherein the first surface includes a plurality of first engagement features, and wherein the second surface includes a plurality of second engagement features configured to engage the plurality of first engagement features.

19. The apparatus of any of embodiments 1-18, wherein the at least two locking sheets includes a first locking sheet and a second locking sheet that are configured to inter-engage.

20. The apparatus of any of embodiments 1-19, wherein the solid regions of the at least two locking sheets are configured to inter-engage with at least one of the solid regions and the open regions of at least one other locking sheet.

21. The apparatus of any of embodiments 1-20, wherein at least one locking sheet includes continuous solid regions.

22. The apparatus of embodiment 21, wherein the solid regions include a plurality of islands and one or more bridges positioned to connect adjacent islands, wherein each bridge includes at least one bend.

23. The apparatus of embodiment 22, wherein each bridge includes at least one 90-degree angle bend.

24. The apparatus of embodiment 22 or 23, wherein each bridge includes at least one 60-degree angle bend.

25. The apparatus of any of embodiments 22-24, wherein each bridge includes at least one 180-degree angle bend.

26. The apparatus of any of embodiments 22-25, wherein each island is connected to four adjacent islands by four bridges, respectively.

27. The apparatus of any of embodiments 22-26, wherein each island is connected to three adjacent islands by three bridges, respectively.

28. The apparatus of any of embodiments 22-27, where at least two locking sheets are arranged relative to one another such that an island in a first locking sheet overlaps a bridge of a second locking sheet.

29. The apparatus of any of embodiments 1-28, wherein at least one locking sheet includes discrete solid regions.

30. The apparatus of any of embodiments 1-28, wherein the at least one locking sheet includes discrete solid regions coupled to a substrate.

31. The apparatus of embodiment 29 or 30, wherein at least one discrete solid region includes a fixed end coupled to a substrate and a free end that is not coupled to the substrate.

32. The apparatus of embodiment 31, wherein the free end of a discrete solid region in a first locking sheet overlaps at least a portion of a discrete solid region in a second locking sheet.

33. The apparatus of embodiment 32, wherein the free end of a discrete solid region in the first locking sheet overlaps at least a portion of a discrete solid region in the second locking sheet in two directions.

34. The apparatus of embodiment 33, wherein the free end of a discrete solid region in the first locking sheet further overlaps at least a portion of an adjacent discrete solid region in the first locking sheet.

35. The apparatus of embodiment 34, wherein the free end of a discrete solid region in the first locking sheet overlaps at least a portion of an adjacent discrete solid region in the first locking sheet in two directions.

36. The apparatus of any of embodiments 30-35, wherein the envelope provides the substrate, such that the solid regions are coupled directly to the envelope.

37. The apparatus of any of embodiments 29-36, wherein the at least one locking sheet including discrete solid regions is coupled to an inner surface of the envelope.

38. The apparatus of any of embodiments 1-37, wherein at least one locking sheet includes continuous solid regions and at least one locking sheet includes discrete solid regions.

39. The apparatus of any of embodiments 1-38, wherein the solid regions and the open regions in each locking sheet form a hexagonally-packed pattern.

40. The apparatus of any of embodiments 1-39, wherein the solid regions and the open regions in each locking sheet form a square-packed pattern.

41. The apparatus of any of embodiments 1-40, wherein the at least two locking sheets include locking sheets formed of different materials.

42. The apparatus of any of embodiments 1-41, wherein the at least two locking sheets include locking sheets having different patterns.

43. The apparatus of any of embodiments 1-42, wherein the at least two locking sheets include one or more locking sheets rotated with respect to one another about a z-axis that is substantially normal to each locking sheet.

44. The apparatus of any of embodiments 1-43, wherein at least one locking sheet includes a varying pattern of solid regions and open regions.

45. The apparatus of embodiment 44, wherein the varying pattern varies from a center out toward an edge of the at least one locking sheet.

46. The apparatus of any of embodiments 1-45, wherein at least one locking sheet includes more than one pattern of solid regions and open regions.

47. The apparatus of any of embodiments 1-46, wherein at least two of the at least two locking sheets have different thicknesses.

48. The apparatus of any of embodiments 1-47, wherein at least one locking sheet has a thickness that varies.

49. The apparatus of any of embodiments 1-48, wherein at least one locking sheet is formed of an annealed metal.

50. The apparatus of any of embodiments 1-49, wherein at least one locking sheet is fixed in at least one location relative to at least one of (i) another locking sheet, and (ii) the envelope.

51. The apparatus of any of embodiments 1-50, wherein the apparatus is sheet-like.

52. The apparatus of any of embodiments 1-51, wherein the apparatus has a first ratio of thickness to a first surface dimension and a second ratio of thickness to a second surface dimension, and wherein the first ratio and the second ratio are each less than 0.1.

53. The apparatus of any of embodiments 1-52, wherein the envelope includes a low friction outer surface.

54. The apparatus of any of embodiments 1-53, wherein the envelope is formed of at least one of polydimethylsiloxane, liquid silicone rubber, poly(styrene-butadiene-styrene), and a combination thereof.

55. The apparatus of any of embodiments 1-54, wherein the port is configured to be coupled to a vacuum source.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The following working examples are intended to be illustrative of the present disclosure and not limiting.

EXAMPLES

Example 1

Shape-Formable Apparatus—Assembly

With reference to FIG. 1, three shape-formable apparatuses 100 were assembled in the following manner. Twenty locking sheets 110 of 11.43 cm (4.5 in)×11.43 cm (4.5 in)×9.7E-2 cm (3.8E-3 in) 20 lb. paper obtained from Staples, Inc. of Framingham, Mass. were placed on top of one another in an overlapping stack where the solid regions 132 and open regions 134 of the locking sheets 110 were aligned with one another. Each of the twenty sheets was patterned to match the design represented and described in FIG. 15. The stack of twenty locking sheets 110 was then placed into a 1.27E-2 cm (5.0E-3 in) thick polyurethane envelope 102 obtained from Lubrizol Corp. of Wickliffe, Ohio and sealed with an AIE-100T Impulse Hand Sealer obtained from American International Electric of City of Industry, CA. A port 115 was inserted through the polyurethane envelope 102 prior to sealing.

Three additional shape-formable apparatuses 100 were assembled identically to the procedure defined above with the exception that the twenty sheets were not patterned.

To change the state of the shape-formable apparatuses 100 from unlocked (formable) to locked (rigid), a DOA-P704-AA oilless diaphragm vacuum pump obtained from Gast of Benton Harbor, Mich. was connected to the port 115 through a connector 122 obtained from McMaster-Carr of Elmhurst, Ill. The vacuum source 120 was activated and the pressure within the envelope 102 was reduced to approximately −78 kPa to change the state of the shape-formable apparatuses 100 from formable to rigid. The vacuum source 120 was maintained to keep the apparatuses in the locked condition (i.e., second state).

Example 2

Shape-Formable Apparatus—Performance

The six shape-formable apparatuses 100 assembled in Example 1 were subjected to three tests to determine their effective tensile, bending, and indentation moduli while in the formable (unlocked) and rigid (locked) states. The shape-formable apparatuses 100 were characterized via the following test procedures.

Test Procedures

Effective Tensile Modulus

Effective Tensile Modulus was measured by placing the shape-formable apparatus 100 into a LF Plus Digital Material Tester obtained from Ametek Measurement & Calibration Technologies (formerly Lloyd Instruments) of Largo, Fla. Two opposite ends of the shape-formable apparatuses 100 were clamped into the LF Plus Digital Material Tester with rubber faced manual operated vice grips also obtained from Ametek Measurement & Calibration Technologies (formerly Lloyd Instruments) of Largo, Fla. Each of the three formable (unlocked) shape-formable apparatuses 100 were tested three times and the average values of the force exerted per distance (N/mm) extended were recorded. Each of the three rigid (locked) shape-formable apparatuses 100 were tested three times and the average values of the force exerted per distance (N/mm) extended were recorded as measured tension, $T_{measured}$.

The Effective Tensile Modulus (i.e., for rectangular specimens) is defined as the Force per unit width divided by strain:

$$ETM = \frac{\text{Force per unit width}}{\text{strain}} = \frac{F/W}{\Delta L/L} = \left(\frac{F}{\Delta L}\right)\left(\frac{L}{W}\right).$$

The procedure described above measures the force divided by extension $$T_{measured} = \frac{F}{\Delta L}.$$

The Effective Tensile Modulus was calculated from the measured tension, $T_{measured}$, by multiplying by the length and dividing by the width of the sample, $$ETM = T_{measured}\left(\frac{L}{W}\right).$$

Effective Bending Modulus

Measurement of the Effective Bending Modulus was performed by clamping one end of the shape-formable apparatus 100 with a rubber faced manual operated vice grip obtained from Ametek Measurement & Calibration Technologies (formerly Lloyd Instruments) of Largo, Fla. The other end of the shape-formable apparatus 100 was oriented straight down (aligned with gravity) and clamped with a binder clip. The binder clip was attached to a cable composed of fishing line obtained from Shimano Corp. of Irvine, Calif. through a pulley, such that the binder clip was pulled orthogonal to gravity, and attached to the LF Plus Digital Material Tester obtained from Ametek Measurement & Calibration Technologies (formerly Lloyd Instruments) of Largo, Fla., to measure the deflection distance, x. Each of the three formable (unlocked) shape-formable apparatuses 100 were tested three times and the average values of the bending force per distance bent (or deflected) (N/mm) were recorded. Each of the three rigid (locked) shape-formable apparatuses 100 were tested three times and the average values of the force exerted per distance bent (or deflected) (N/mm) were recorded as measured bending, $B_{measured}$.

The Effective Bending Modulus is defined as the Force per unit width divided by the angle of deflection:

$$EBM = \frac{\text{Force per unit width}}{\text{theta}} = \frac{F/w}{\theta}.$$

The angle of deflection can be approximated (small angle approximation) as $$\theta \sim \frac{x}{L},$$

which implies that $$EBM = \frac{F/w}{x/L} = \left(\frac{F}{x}\right)\left(\frac{L}{w}\right),$$

were x is the deflection distance. The procedure described above measures the force divided by the deflection distance, $$B_{measured} = \frac{F}{x}.$$

The Effective Bending Modulus was calculated from the measured Bending, $B_{measured}$, by multiplying by the length and dividing by the width of the sample, $$EBM = B_{measured}\left(\frac{L}{W}\right).$$

Effective Indentation Modulus

Indentation stiffness was performed by placing the shape-formable apparatus 100 on a ring support structure. The shape-formable apparatus 100 was free to slide across the surface of the ring support structure. The inner diameter of the ring support structure was 2.40 in (6.10 cm). The center of the shape-formable apparatus 100 was pushed or indented with a LF Plus Digital Material Tester obtained from Ametek Measurement & Calibration Technologies (formerly Lloyd Instruments) of Largo, Fla. The diameter of the tip that pushed on the apparatus was 0.63 in (1.60 cm). Each of the three formable (unlocked) shape-formable apparatuses 100 were tested three times and the average values of the indentation force per distance indented (N/mm) were recorded. Each of the three rigid (locked) shape-formable apparatuses 100 were tested three times and the average values of the force exerted per distance (N/mm) extended were recorded.

The Effective Indentation Modulus is defined as the force applied to the sample divided by the deflection distance:

$$EIM = \frac{\text{Force applied}}{\text{deflection distance}} = \frac{F}{x}.$$

This is the direct measurement that is made by the procedure above, so no calculation was necessary.

Results of the tests are summarized in Table 1. Ratios of the average locked stiffness as compared to the average unlocked stiffness for each of the tests were also computed and are recorded in Table 1.

In addition, the polyurethane envelope 102 used in the examples was tested by itself according to the Effective Tensile Modulus method described above, and was found to have an Effective Tensile Modulus of 1.21 N/mm.

TABLE 1

ETM, EBM and EIM for locked and unlocked apparatuses including unpatterned and patterned locking sheets.

| | Paper, 20 sheets, Not Patterned | | | Paper, 20 sheets, Patterned | | |
|---|---|---|---|---|---|---|
| | Locked (L) [N/mm] | Unlocked (UL) [N/mm] | Ratio [L/UL] | Locked (L) [N/mm] | Unlocked (UL) [N/mm] | Ratio [L/UL] |
| ETM | 3738 | 3824 | 1.0 | 70.1 | 4.3 [$E_a$] | 16.1 |
| EBM | 0.056 | 0.0038 | 14.5 | 0.0067 | 0.0016 | 4.2 |
| EIM | 13.2 | 5.9 | 2.2 | 8.0 | 0.97 | 8.2 |

This data shows that the unpatterned paper cannot be easily extended, limiting its conformability, while the patterned paper is about 1000 times easier to extend. A significant ratio in the locked/unlocked extensibility with the patterned paper was observed, versus no measureable change for the unpatterned paper. The indentation ratio was also better with the patterned paper. Significant wrinkling was also seen in the indentation test of the solid (i.e., unpatterned) paper.

Example 3

ETM Performance of Patterned Vs. Unpatterned Locking Sheets

Six sets of locking sheets were assembled with the following characteristics; (1) a stack of 20 unpatterned paper sheets, (2) a stack of 20 sheets of paper cut with the pattern of FIG. 15 with a laser cutter (Model No. ILS 9.75, available from Universal Laser System, Scottsdale, Ariz.) (3) 1 sheet of unpatterned 0.005" thick annealed aluminum, (4) 1 sheet of 0.005" thick annealed aluminum patterned via water jet cutting with the pattern shown in FIG. 15, (5) 2 sheets of ⅟₁₆" thick unpatterned Delrin, and (6) 2 sheets of ⅟₁₆" Delrin cut with the pattern of FIG. 15. The Effective Tensile Modulus of all six sets of sheets was tested according to the procedure in Example 2. The results of the testing are summarized below in Table 2.

TABLE 2

ETM for patterned and unpatterned locking sheets.

| Material | Patterned ETM [$E_1$, N/mm] | Unpatterned ETM [$E_o$, N/mm] | Ratio [$E_o/E_1$] |
|---|---|---|---|
| 1 Sheet Paper (.003") | 0.0022 | 24.5 | 10,947 |
| 1 Sheet Delrin (.063") | 2.7 | 1,868 | 692 |
| 1 Sheet Aluminum (.005") | 0.87 | 2,375 | 2,448 |

In addition, the overall ETM for an unlocked apparatus ($E_a$) comprising 20 sheets of patterned paper was reported in Table 1 as 4.3 (N/mm), and the ETM for unpatterned paper ($E_o$) was reported in Table 2 as 24.5, so the ratio of $E_o/E_a$ for an apparatus comprising 20 patterned paper locking sheets is (24.5/4.3) about 6.

All references and publications cited herein are expressly incorporated herein by reference in their entirety into this disclosure.

Various features and aspects of the present disclosure are set forth in the following claims.

What is claimed is:

1. A shape-formable apparatus comprising:
   an envelope defining a chamber, the envelope formed of a gas-impermeable material;
   a port positioned to fluidly couple the chamber with ambience; and
   at least two locking sheets positioned in the chamber in an at least partially overlapping configuration, wherein each locking sheet comprises a major surface, and wherein at least a portion of each locking sheet is patterned to include solid regions and open regions, the solid regions within a single locking sheet being movable with respect to one another through the major surface, wherein the solid regions of at least one locking sheet are formed of a material having an effective tensile modulus ($E_o$), and wherein the solid regions and open regions are arranged in the at least one locking sheet such that the at least one locking sheet has an overall effective tensile modulus ($E_l$), and wherein the ratio of $E_o/E_l$ for the at least one locking sheet is at least 2,
   wherein the apparatus can be changed from a first state to a second state by at least partially evacuating the chamber, in the first state the apparatus is formable, such that the apparatus can be formed into a desired shape, and in the second state the apparatus has the desired shape and is substantially less formable than in the first state.

2. The apparatus of claim 1, wherein the solid regions are movable with respect to one another from a first position to a second position that can be maintained, without plastic deformation, after an applied force is removed.

3. The apparatus of claim 1, wherein the ratio of $E_o/E_l$ for the at least one locking sheet is at least 2 in any direction within through the major surface of each locking sheet.

4. The apparatus of claim 1, wherein the ratio of $E_o/E_l$ for the at least one locking sheet is at least 10.

5. The apparatus of claim 1, wherein the solid regions of at least one locking sheet are formed of a material having a first effective tensile modulus ($E_o$), and wherein the apparatus has an overall effective tensile modulus ($E_a$) when the apparatus is in the first state, and wherein the ratio of $E_o/E_a$ is at least 2.

6. The apparatus of claim 1, wherein the at least two locking sheets are oriented substantially parallel with respect to one another.

7. The apparatus of claim 1, wherein the apparatus has a first effective tensile modulus ($E_{UL}$) when in the first state and a second effective tensile modulus ($E_L$) when in the second state, and wherein the ratio of the second modulus to the first modulus ($E_L/E_{UL}$) is at least 2.

8. The apparatus of claim 1, wherein the apparatus is configured to substantially conform to a complex surface having a non-zero Gaussian curvature when the apparatus is in the first state.

9. The apparatus of claim 1, wherein the solid regions of at least one locking sheet are formed of a material having a strain at yield ($\varepsilon_o$), wherein the solid regions and the open regions are arranged such that the at least one locking sheet is configured to experience a strain ($\varepsilon_l$) without yielding when the apparatus is in the first state, and wherein the strain ratio of $\varepsilon_l/\varepsilon_o$ is at least 1.

10. The apparatus of claim 1, wherein the at least two locking sheets are movable relative to one another in the chamber when the apparatus is in the first state but are substantially immovable relative to one another when the apparatus is in the second state.

11. The apparatus of claim 1, wherein at least one locking sheet includes a friction surface oriented to face another locking sheet.

12. The apparatus of claim 1, wherein the at least two locking sheets includes a first locking sheet and a second locking sheet that are configured to inter-engage.

13. The apparatus of claim 1, wherein at least one locking sheet includes continuous solid regions.

14. The apparatus of claim 1, wherein at least one locking sheet includes discrete solid regions.

15. The apparatus of claim 14, wherein at least one of the discrete solid regions includes a fixed end coupled to a substrate and a free end that is not coupled to the substrate.

16. The apparatus of claim 15, wherein the free end of a discrete solid region in a first locking sheet overlaps at least a portion of a discrete solid region in a second locking sheet.

17. The apparatus of claim 1, wherein the apparatus is sheet-like.

18. A shape-formable apparatus comprising:
   an envelope defining a chamber, the envelope formed of a gas-impermeable material;
   a port positioned to fluidly couple the chamber with ambience; and
   at least two locking sheets positioned in the chamber in an at least partially overlapping configuration, wherein each locking sheet comprises a major surface, and wherein at least a portion of each locking sheet is patterned to include solid regions and open regions, the solid regions within a single locking sheet being movable with respect to one another through the major surface,
   wherein the at least two locking sheets includes a first locking sheet comprising a first surface oriented to face a second locking sheet and a second locking sheet comprising a second surface oriented to face the first locking sheet, wherein the first surface includes a plurality of first engagement features, and wherein the second surface includes a plurality of second engagement features configured to engage the plurality of first engagement features, and wherein the apparatus can be changed from a first state to a second state by at least partially evacuating the chamber, in the first state the apparatus is formable, such that the apparatus can be formed into a desired shape, and in the second state the apparatus has the desired shape and is substantially less formable than in the first state.

19. A shape-formable apparatus comprising:

an envelope defining a chamber, the envelope formed of a gas-impermeable material;

a port positioned to fluidly couple the chamber with ambience; and at least two locking sheets positioned in the chamber in an at least partially overlapping configuration, wherein each locking sheet comprises a major surface, and wherein at least a portion of each locking sheet is patterned to include solid regions and open regions, the solid regions within a single locking sheet being movable with respect to one another through the major surface, wherein at least one locking sheet includes continuous solid regions, the solid regions include a plurality of islands and one or more bridges positioned to connect adjacent islands, wherein each bridge includes at least one bend, and wherein the apparatus can be changed from a first state to a second state by at least partially evacuating the chamber, in the first state the apparatus is formable, such that the apparatus can be formed into a desired shape, and in the second state the apparatus has the desired shape and is substantially less formable than in the first state.

* * * * *

UNITED STATES PATENT AND TRADEMARK OFFICE
CERTIFICATE OF CORRECTION

PATENT NO. : 10,538,049 B2
APPLICATION NO. : 15/535297
DATED : January 21, 2020
INVENTOR(S) : Thomas Corrigan Page 1 of 1

It is certified that error appears in the above-identified patent and that said Letters Patent is hereby corrected as shown below:

In the Specification

Column 5
Line 10, Delete "www.3 m.com" and insert -- www.3m.com --, therefor.

In the Claims

Column 45
Line 49, In Claim 1, delete "$E_i$" and insert -- $E_1$ --, therefor.
Line 50, In Claim 1, delete "$E_i$" and insert -- $E_1$ --, therefor.
Line 62, In Claim 3, delete "$E_i$" and insert -- $E_1$ --, therefor.
Line 65, In Claim 3, after "direction" delete "within".
Line 66, In Claim 4, delete "$E_i$" and insert -- $E_1$ --, therefor.

Column 46
Line 25, In Claim 9, delete "$\varepsilon_l/\varepsilon_o$is" and insert -- $\varepsilon_l/\varepsilon_o$ is --, therefor.

Signed and Sealed this
Sixteenth Day of June, 2020

Andrei Iancu
*Director of the United States Patent and Trademark Office*